(12) United States Patent
Weston

(10) Patent No.: US 11,730,874 B2
(45) Date of Patent: **\*Aug. 22, 2023**

(54) REDUCED PRESSURE TREATMENT APPLIANCE

(71) Applicant: Smith & Nephew, Inc., Memphis, TN (US)

(72) Inventor: Richard Scott Weston, Encinitas, CA (US)

(73) Assignee: Smith & Nephew, Inc., Memphis, TN (US)

(\*) Notice: Subject to any disclaimer, the term of this patent is extended or adjusted under 35 U.S.C. 154(b) by 1058 days.

This patent is subject to a terminal disclaimer.

(21) Appl. No.: 16/522,083

(22) Filed: Jul. 25, 2019

(65) Prior Publication Data

US 2019/0343993 A1    Nov. 14, 2019

Related U.S. Application Data

(63) Continuation of application No. 14/949,624, filed on Nov. 23, 2015, now Pat. No. 10,363,346, which is a (Continued)

(51) Int. Cl.
*A61M 1/00* (2006.01)
*A61F 13/00* (2006.01)

(52) U.S. Cl.
CPC ......... *A61M 1/68* (2021.05); *A61F 13/00068* (2013.01); *A61M 1/60* (2021.05);
(Continued)

(58) Field of Classification Search
CPC .... A61M 1/009; A61M 1/005; A61M 1/0052; A61M 1/0001; A61M 1/0088;
(Continued)

(56) References Cited

U.S. PATENT DOCUMENTS

| 59,388 A | 11/1866 | Hadfield |
|---|---|---|
| 70,088 A | 10/1867 | Hadfield |

(Continued)

FOREIGN PATENT DOCUMENTS

| CA | 1111204 A1 | 10/1981 |
|---|---|---|
| CA | 1305586 C | 6/1988 |

(Continued)

OTHER PUBLICATIONS

US 6,216,701 B1, 04/2001, Heaton et al. (withdrawn)
(Continued)

*Primary Examiner* — Andrew J Mensh
(74) *Attorney, Agent, or Firm* — Knobbe, Martens Olson & Bear, LLP

(57) ABSTRACT

A wound treatment appliance is provided for treating all or a portion of a wound. In some embodiments, the appliance comprises an impermeable flexible overlay that covers all or a portion of the wound for purposes of applying a reduced pressure to the covered portion of the wound. In other embodiments, the impermeable flexible overlay comprises suction assistance means, such as channels, which assist in the application of reduced pressure to the area of the wound and removal of exudate from the wound. In other embodiments, the wound treatment appliance also includes a vacuum system to supply reduced pressure to the wound in the area under the flexible overlay. In yet other embodiments, the wound treatment appliance also includes wound packing means to prevent overgrowth of the wound or to encourage growth of the wound tissue into an absorbable matrix comprising the wound packing means. In still other embodiments, the appliance may include a suction drain. In other embodiments, the appliance may include a collection chamber to collect and store exudate from the wound. In yet other embodiments, a suction bulb may be used to provide (Continued)

a source of reduced pressure to an impermeable overlay that covers all or a portion of the wound. Finally, methods are provided for using various embodiments of the wound treatment appliance.

22 Claims, 8 Drawing Sheets

Related U.S. Application Data continuation of application No. 13/902,446, filed on May 24, 2013, now Pat. No. 9,198,801, which is a continuation of application No. 12/832,031, filed on Jul. 7, 2010, now Pat. No. 8,449,509, which is a continuation of application No. 11/098,265, filed on Apr. 4, 2005, now Pat. No. 7,909,805, which is a continuation-in-part of application No. 11/064,813, filed on Feb. 24, 2005, now Pat. No. 8,062,272.

(60) Provisional application No. 60/559,727, filed on Apr. 5, 2004.

(52) U.S. Cl.
CPC ............ *A61M 1/682* (2021.05); *A61M 1/782* (2021.05); *A61M 1/784* (2021.05); *A61M 1/962* (2021.05); *A61M 1/98* (2021.05); *A61M 2205/075* (2013.01)

(58) Field of Classification Search
CPC .... A61M 35/00; A61M 1/784; A61M 1/0011; A61M 2205/075; A61F 13/00068
USPC ......................................... 604/304, 313, 317
See application file for complete search history.

(56) References Cited

U.S. PATENT DOCUMENTS

| | | |
|---|---|---|
| 695,270 A | 3/1902 | Beringer |
| 765,746 A | 7/1904 | Miner |
| 774,529 A | 11/1904 | Nieschange |
| 846,674 A | 7/1907 | Funk |
| D41,984 S | 12/1911 | Marcuse |
| 1,052,274 A | 2/1913 | Purdy |
| 1,066,934 A | 7/1913 | Manney |
| 1,355,679 A | 10/1920 | McConnell |
| 1,355,846 A | 10/1920 | Rannells |
| 1,385,346 A * | 7/1921 | Taylor ............... A61F 13/00068 604/305 |
| 1,480,562 A | 1/1924 | Mock |
| 1,585,104 A | 5/1926 | Montgomery |
| 1,629,108 A | 5/1927 | Lake |
| 1,769,147 A | 12/1927 | Lennon |
| 1,732,310 A | 12/1929 | Naibert |
| 1,863,534 A | 6/1932 | Odell |
| 1,936,120 A | 11/1933 | Schmidt |
| 1,936,129 A | 11/1933 | Fisk |
| 2,054,768 A | 9/1936 | Gale, Jr. et al. |
| 2,122,121 A | 6/1938 | Tillotson |
| 2,195,771 A | 4/1940 | Estler |
| 2,232,254 A | 2/1941 | Morgan |
| 2,280,915 A | 4/1942 | Johnson |
| 2,318,888 A | 5/1943 | Sanders |
| 2,338,339 A | 1/1944 | La Mere et al. |
| 2,366,799 A | 1/1945 | Luisada |
| 2,367,690 A | 1/1945 | Purdy |
| 2,385,683 A | 9/1945 | Burton |
| 2,547,758 A | 4/1951 | Keeling |
| 2,568,933 A | 9/1951 | Robbins |
| 2,706,865 A | 12/1951 | Miller |
| 2,613,696 A | 10/1952 | MacIntyre |
| 2,632,443 A | 3/1953 | Lesher |
| 2,682,873 A | 7/1954 | Evans et al. |
| 2,910,763 A | 8/1955 | Lauterbach |
| 2,905,174 A | 9/1959 | Smith |
| 3,026,874 A | 11/1959 | Stevens |
| 2,927,577 A | 3/1960 | Nicolaie |
| 2,969,057 A | 1/1961 | Simmons |
| 3,026,526 A | 3/1962 | Montrose |
| 3,042,041 A | 7/1962 | Jascalevich |
| 3,043,301 A | 7/1962 | Plantinga et al. |
| 3,060,932 A | 10/1962 | Pereny et al. |
| 3,115,138 A | 12/1963 | McElvenny et al. |
| 3,123,074 A | 3/1964 | Turner |
| 3,217,707 A | 11/1965 | Werding |
| 3,238,056 A | 3/1966 | Pall et al. |
| 3,238,937 A | 3/1966 | Stein |
| 3,286,711 A | 11/1966 | MacLeod |
| 3,288,140 A | 11/1966 | McCarthy |
| 3,315,665 A * | 4/1967 | MacLeod ............. A61N 1/0408 601/7 |
| 3,342,183 A | 9/1967 | Martin et al. |
| 3,367,332 A | 2/1968 | Groves |
| 3,376,868 A | 4/1968 | Mondiadis |
| 3,465,748 A | 9/1969 | Kravchenko |
| 3,478,736 A | 11/1969 | Roberts et al. |
| 3,486,504 A | 12/1969 | Austin, Jr. |
| 3,520,300 A | 7/1970 | Flower, Jr. |
| 3,529,597 A | 9/1970 | Fuzak et al. |
| 3,568,675 A | 3/1971 | Harvey |
| 3,572,340 A | 3/1971 | Lloyd et al. |
| 3,610,238 A | 10/1971 | Rich, Jr. |
| 3,624,821 A | 11/1971 | Henderson |
| 3,633,567 A | 1/1972 | Sarnoff |
| 3,682,180 A | 8/1972 | McFarlane |
| 3,687,136 A | 8/1972 | Carmody |
| 3,712,298 A | 1/1973 | Snowdon et al. |
| 3,713,622 A | 1/1973 | Dinger |
| 3,727,629 A | 4/1973 | Gifford |
| 3,763,857 A | 10/1973 | Schrading et al. |
| 3,783,870 A | 1/1974 | Schachet |
| 3,794,035 A | 2/1974 | Brenner |
| 3,826,254 A | 7/1974 | Mellor |
| 3,835,564 A | 9/1974 | Gottschalk |
| 3,841,331 A | 10/1974 | Wilder et al. |
| 3,859,989 A | 1/1975 | Spielberg |
| 3,863,369 A | 2/1975 | Kinne |
| 3,871,377 A | 3/1975 | Treace et al. |
| 3,874,387 A | 4/1975 | Barbieri |
| 3,896,810 A | 7/1975 | Akiyama |
| 3,908,642 A | 9/1975 | Vinmont |
| 3,908,664 A | 9/1975 | Loseff |
| 3,938,540 A | 2/1976 | Holbrook et al. |
| 3,954,105 A | 5/1976 | Nordby et al. |
| 3,961,625 A | 6/1976 | Dillon |
| 3,972,328 A | 8/1976 | Chen |
| 3,986,606 A | 10/1976 | Davis |
| 3,988,793 A | 11/1976 | Abitbol |
| 3,993,080 A | 11/1976 | Loseff |
| 4,029,598 A | 6/1977 | Neisius et al. |
| RE29,319 E | 7/1977 | Nordby et al. |
| D246,289 S | 11/1977 | Boucher |
| 4,073,294 A | 2/1978 | Stanley et al. |
| 4,080,970 A | 3/1978 | Miller |
| 4,102,342 A | 7/1978 | Akiyama et al. |
| 4,112,947 A | 9/1978 | Nehring |
| 4,117,551 A | 9/1978 | Books et al. |
| 4,136,696 A | 1/1979 | Nehring |
| 4,149,541 A * | 4/1979 | Gammons ............... A61M 1/90 607/104 |
| 4,169,563 A | 10/1979 | Leu |
| 4,172,455 A | 10/1979 | Beaussant |
| 4,178,938 A | 12/1979 | Au |
| 4,180,074 A | 12/1979 | Murry et al. |
| 4,184,510 A | 1/1980 | Murry et al. |
| 4,212,296 A | 7/1980 | Schaar |
| 4,217,894 A | 8/1980 | Franetzki |
| 4,219,019 A | 8/1980 | Coates |
| 4,224,945 A | 9/1980 | Cohen |
| 4,228,798 A | 10/1980 | Deaton |
| 4,241,299 A | 12/1980 | Bertone |
| 4,250,882 A | 2/1981 | Adair |

(56) References Cited

U.S. PATENT DOCUMENTS

| | | |
|---|---|---|
| 4,252,119 A | 2/1981 | Coates |
| D258,577 S | 3/1981 | Bottner |
| 4,256,109 A | 3/1981 | Nichols |
| 4,261,363 A | 4/1981 | Russo |
| 4,266,545 A | 5/1981 | Moss |
| 4,275,721 A | 6/1981 | Olson |
| 4,278,089 A | 7/1981 | Huck et al. |
| 4,297,995 A | 11/1981 | Golub |
| 4,316,466 A | 2/1982 | Babb |
| 4,333,468 A | 6/1982 | Geist |
| 4,341,207 A | 7/1982 | Steer et al. |
| 4,360,015 A | 11/1982 | Mayer |
| 4,360,021 A | 11/1982 | Stima |
| D267,510 S | 1/1983 | Golub |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,392,860 A | 7/1983 | Huck et al. |
| 4,396,023 A | 8/1983 | Anderson |
| D270,485 S | 9/1983 | Cervantes |
| 4,404,924 A | 9/1983 | Goldbert et al. |
| 4,418,691 A | 12/1983 | Yannas et al. |
| 4,419,093 A | 12/1983 | Deaton |
| 4,419,097 A | 12/1983 | Rowland |
| 4,421,109 A | 12/1983 | Thornton |
| 4,432,354 A | 2/1984 | Lasley |
| 4,444,548 A | 4/1984 | Andersen et al. |
| 4,452,845 A | 6/1984 | Lloyd et al. |
| 4,459,139 A | 7/1984 | vonReis et al. |
| 4,465,485 A | 8/1984 | Kashmer et al. |
| 4,468,227 A | 8/1984 | Jensen |
| 4,469,092 A | 9/1984 | Marshall et al. |
| 4,475,909 A | 10/1984 | Eisenberg |
| 4,480,638 A | 11/1984 | Schmid |
| 4,499,896 A | 2/1985 | Heinecke |
| D278,207 S | 4/1985 | McLaughlin |
| 4,523,920 A | 6/1985 | Russo |
| 4,524,064 A | 6/1985 | Nambu |
| 4,525,166 A | 6/1985 | Leclerc |
| 4,527,064 A | 7/1985 | Anderson |
| 4,529,402 A | 7/1985 | Weilbacher et al. |
| 4,533,352 A | 8/1985 | Van Beek et al. |
| 4,534,356 A | 8/1985 | Papadakis |
| 4,538,920 A | 9/1985 | Drake et al. |
| 4,540,412 A | 9/1985 | Van Overloop |
| 4,543,100 A | 9/1985 | Brodsky |
| 4,544,590 A | 10/1985 | Egan |
| 4,551,141 A | 11/1985 | McNeil |
| D281,827 S | 12/1985 | Bakic |
| 4,561,435 A | 12/1985 | McKnight et al. |
| 4,564,010 A | 1/1986 | Coughlan et al. |
| 4,569,674 A | 2/1986 | Phillips |
| 4,573,965 A | 3/1986 | Russo |
| 4,578,060 A | 3/1986 | Huck et al. |
| 4,587,101 A | 5/1986 | Marsoner et al. |
| 4,587,146 A | 5/1986 | Anhauser et al. |
| 4,605,399 A | 8/1986 | Weston et al. |
| 4,608,041 A | 8/1986 | Nielsen |
| 4,624,656 A | 11/1986 | Clark et al. |
| 4,627,429 A | 12/1986 | Tsuk |
| 4,640,688 A | 2/1987 | Hauser |
| 4,648,870 A | 3/1987 | Goldberg et al. |
| 4,655,202 A | 4/1987 | Potter et al. |
| 4,655,754 A | 4/1987 | Richmond et al. |
| 4,655,766 A | 4/1987 | Theeuwes et al. |
| 4,661,093 A | 4/1987 | Beck et al. |
| 4,664,662 A | 5/1987 | Webster |
| 4,681,562 A | 7/1987 | Beck et al. |
| 4,691,695 A | 9/1987 | Birk et al. |
| 4,699,134 A | 10/1987 | Samuelsen |
| D292,826 S | 11/1987 | Sproles |
| 4,710,165 A | 12/1987 | McNeil et al. |
| 4,713,052 A | 12/1987 | Beck et al. |
| 4,717,382 A | 1/1988 | Clemens et al. |
| 4,726,745 A | 2/1988 | Adahan |
| 4,728,499 A | 3/1988 | Fehder |
| 4,738,249 A | 4/1988 | Linman |
| 4,740,202 A | 4/1988 | Stacey et al. |
| 4,743,232 A | 5/1988 | Kruger |
| 4,753,231 A | 6/1988 | Lang et al. |
| 4,753,536 A | 6/1988 | Spehar et al. |
| 4,759,354 A | 7/1988 | Quarfoot |
| 4,764,167 A | 8/1988 | Tu |
| 4,765,316 A | 8/1988 | Marshall |
| 4,767,026 A | 8/1988 | Keller |
| 4,768,501 A | 9/1988 | George |
| 4,771,919 A | 9/1988 | Ernst |
| 4,772,259 A | 9/1988 | Freeh et al. |
| 4,778,446 A | 10/1988 | Jensen |
| 4,778,456 A | 10/1988 | Lokken |
| 4,790,833 A | 12/1988 | Schmidt |
| 4,792,328 A | 12/1988 | Beck et al. |
| 4,795,435 A | 1/1989 | Steer |
| 4,795,448 A | 1/1989 | Stacey et al. |
| 4,798,583 A | 1/1989 | Beck et al. |
| 4,798,603 A | 1/1989 | Meyer et al. |
| 4,808,172 A | 2/1989 | Murata |
| 4,813,931 A | 3/1989 | Hauze |
| 4,813,942 A | 3/1989 | Alvarez |
| 4,817,594 A | 4/1989 | Juhasz |
| 4,820,265 A | 4/1989 | DeSatnick et al. |
| 4,820,284 A | 4/1989 | Hauri |
| 4,826,494 A | 5/1989 | Richmond et al. |
| 4,828,546 A | 5/1989 | McNeil et al. |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A | 6/1989 | Berg et al. |
| 4,847,083 A | 7/1989 | Clark |
| 4,851,545 A | 7/1989 | Song et al. |
| 4,860,737 A | 8/1989 | Lang et al. |
| 4,863,449 A | 9/1989 | Therriault et al. |
| 4,867,150 A | 9/1989 | Gilbert |
| 4,872,450 A | 10/1989 | Austad |
| 4,875,473 A | 10/1989 | Alvarez |
| 4,878,901 A | 11/1989 | Sachse |
| 4,882,213 A | 11/1989 | Gaddis et al. |
| 4,901,714 A | 2/1990 | Jensen |
| 4,902,277 A | 2/1990 | Marhies et al. |
| 4,906,233 A | 3/1990 | Moriuchi et al. |
| 4,917,112 A | 4/1990 | Kalt |
| 4,921,488 A | 5/1990 | Maitz et al. |
| 4,921,492 A | 5/1990 | Schultz |
| 4,923,444 A | 5/1990 | Daoud et al. |
| 4,925,447 A | 5/1990 | Rosenblatt |
| 4,929,477 A | 5/1990 | Will |
| 4,931,519 A | 6/1990 | Song et al. |
| 4,936,834 A | 6/1990 | Beck et al. |
| 4,941,882 A | 7/1990 | Ward et al. |
| 4,950,483 A | 8/1990 | Ksander |
| 4,953,565 A | 9/1990 | Tachibana et al. |
| 4,955,893 A | 9/1990 | Yannas et al. |
| D311,423 S | 10/1990 | DeSantis |
| 4,969,880 A | 11/1990 | Zamierowski |
| 4,969,881 A | 11/1990 | Viesturs |
| 4,972,829 A | 11/1990 | Knerr |
| 4,979,944 A | 12/1990 | Luzsicza |
| 4,981,474 A | 1/1991 | Bopp et al. |
| 4,994,022 A | 2/1991 | Steffler et al. |
| 4,997,425 A | 3/1991 | Shioya et al. |
| 5,000,164 A | 3/1991 | Cooper |
| 5,002,539 A | 3/1991 | Coble et al. |
| 5,007,578 A | 4/1991 | Simone |
| 5,009,635 A | 4/1991 | Scarberry |
| 5,018,515 A | 5/1991 | Gilman |
| 5,030,202 A | 7/1991 | Harris |
| 5,034,006 A | 7/1991 | Hosoda et al. |
| 5,035,884 A | 7/1991 | Song et al. |
| 5,052,381 A | 10/1991 | Gilbert et al. |
| 5,055,198 A | 10/1991 | Shettigar |
| 5,056,510 A | 10/1991 | Gilman |
| 5,064,653 A | 11/1991 | Sessions et al. |

(56) References Cited

U.S. PATENT DOCUMENTS

| | | |
|---|---|---|
| 5,071,409 A | 12/1991 | Rosenberg |
| 5,073,172 A | 12/1991 | Fell |
| 5,080,493 A | 1/1992 | McKown et al. |
| 5,080,661 A | 1/1992 | Lavender et al. |
| 5,086,763 A | 2/1992 | Hathman |
| 5,086,764 A | 2/1992 | Gilman |
| 5,088,483 A | 2/1992 | Heinecke |
| 5,089,606 A | 2/1992 | Cole et al. |
| 5,100,376 A | 3/1992 | Blake |
| 5,100,395 A | 3/1992 | Rosenberg |
| 5,100,396 A | 3/1992 | Zamierowski |
| 5,106,362 A | 4/1992 | Gilman |
| 5,106,629 A | 4/1992 | Cartmell et al. |
| 5,112,323 A | 5/1992 | Winkler et al. |
| 5,113,871 A | 5/1992 | Viljanto et al. |
| 5,115,472 A | 5/1992 | Park et al. |
| 5,134,994 A | 8/1992 | Say |
| 5,141,503 A | 8/1992 | Sewell, Jr. |
| 5,149,331 A | 9/1992 | Ferdman et al. |
| 5,152,757 A | 10/1992 | Eriksson |
| 5,160,315 A | 11/1992 | Heinecke et al. |
| 5,167,613 A | 12/1992 | Karami et al. |
| 5,170,781 A | 12/1992 | Loomis |
| 5,176,663 A | 1/1993 | Svedman et al. |
| 5,181,905 A | 1/1993 | Flam |
| 5,184,077 A | 2/1993 | Day et al. |
| 5,201,780 A | 4/1993 | Dinsmoor et al. |
| 5,215,519 A | 6/1993 | Shettigar |
| 5,218,973 A | 6/1993 | Weaver et al. |
| 5,228,431 A | 7/1993 | Giarretto |
| 5,234,419 A | 8/1993 | Bryant et al. |
| 5,238,720 A | 8/1993 | Volkman |
| 5,238,732 A | 8/1993 | Krishnan |
| 5,243,968 A | 9/1993 | Byun |
| 5,249,709 A | 10/1993 | Duckworth et al. |
| 5,261,893 A | 11/1993 | Zamierowski |
| 5,263,922 A | 11/1993 | Sova et al. |
| 5,264,218 A | 11/1993 | Rogozinski |
| 5,266,371 A | 11/1993 | Sugii et al. |
| 5,266,928 A | 11/1993 | Johnson |
| 5,279,608 A | 1/1994 | Cherif Cheikh |
| 5,288,431 A | 2/1994 | Huber et al. |
| 5,307,791 A | 5/1994 | Senoue et al. |
| 5,310,261 A | 5/1994 | Blue et al. |
| 5,322,695 A | 6/1994 | Shah et al. |
| 5,328,614 A | 7/1994 | Matsumura |
| 5,329,713 A | 7/1994 | Lundell |
| 5,330,448 A | 7/1994 | Chu |
| 5,333,760 A | 8/1994 | Simmen et al. |
| 5,336,209 A | 8/1994 | Porzilli |
| 5,342,093 A | 8/1994 | Weernink |
| 5,350,360 A | 9/1994 | Ensminger et al. |
| 5,358,494 A | 10/1994 | Svedman |
| D352,782 S | 11/1994 | Kirk, III |
| 5,360,398 A | 11/1994 | Grieshaber et al. |
| 5,362,543 A | 11/1994 | Nickerson |
| 5,380,280 A | 1/1995 | Peterson |
| 5,387,209 A | 2/1995 | Yamamoto et al. |
| D357,742 S | 4/1995 | Peery et al. |
| 5,419,768 A | 5/1995 | Kayser |
| 5,425,742 A | 6/1995 | Joy |
| 5,429,601 A | 7/1995 | Conley et al. |
| 5,437,651 A | 8/1995 | Todd et al. |
| 5,445,604 A | 8/1995 | Lang |
| D362,505 S | 9/1995 | Fabricant |
| 5,449,347 A | 9/1995 | Preen et al. |
| 5,462,514 A | 10/1995 | Harris |
| 5,466,229 A | 11/1995 | Elson |
| 5,478,333 A | 12/1995 | Asherman, Jr. |
| 5,479,333 A | 12/1995 | McCambridge et al. |
| 5,484,428 A | 1/1996 | Drainville et al. |
| 5,486,158 A | 1/1996 | Samuelson |
| 5,487,889 A | 1/1996 | Eckert et al. |
| 5,489,280 A | 2/1996 | Russell |
| 5,489,304 A | 2/1996 | Orgill et al. |
| 5,490,984 A | 2/1996 | Freed |
| 5,496,605 A | 3/1996 | Augst et al. |
| 5,498,338 A | 3/1996 | Kruger et al. |
| D369,907 S | 5/1996 | Sayovitz et al. |
| D370,127 S | 5/1996 | Bonaddio et al. |
| 5,514,166 A | 5/1996 | Silver et al. |
| 5,527,293 A | 6/1996 | Zamierowski |
| 5,527,923 A | 6/1996 | Klingler et al. |
| D372,098 S | 7/1996 | Lattin et al. |
| 5,531,855 A | 7/1996 | Heinecke et al. |
| 5,549,584 A | 8/1996 | Gross |
| 5,549,585 A | 8/1996 | Maher et al. |
| 5,562,107 A | 10/1996 | Lavender et al. |
| 5,563,233 A | 10/1996 | Reich et al. |
| 5,577,994 A | 11/1996 | Celik |
| 5,582,596 A | 12/1996 | Fukunaga et al. |
| 5,593,395 A | 1/1997 | Martz |
| 5,599,289 A | 2/1997 | Castellana |
| 5,609,163 A | 3/1997 | Beard |
| 5,609,271 A | 3/1997 | Keller et al. |
| 5,616,387 A | 4/1997 | Augst et al. |
| 5,618,556 A | 4/1997 | Johns et al. |
| 5,624,419 A | 4/1997 | Ersek et al. |
| 5,624,423 A | 4/1997 | Anjur et al. |
| 5,633,007 A | 5/1997 | Webb et al. |
| 5,635,201 A | 6/1997 | Fabo |
| 5,636,643 A | 6/1997 | Argenta |
| 5,637,093 A | 6/1997 | Hyman et al. |
| 5,639,529 A | 6/1997 | Gozdecki et al. |
| 5,643,189 A | 7/1997 | Masini |
| 5,645,081 A | 7/1997 | Argenta et al. |
| 5,645,981 A | 7/1997 | Romanet et al. |
| D382,343 S | 8/1997 | Wandell et al. |
| D384,745 S | 10/1997 | Lattin et al. |
| D385,038 S | 10/1997 | Shultz |
| 5,676,401 A | 10/1997 | Witkowski et al. |
| 5,676,650 A | 10/1997 | Grieshaber et al. |
| 5,678,564 A | 10/1997 | Lawrence et al. |
| 5,681,579 A | 10/1997 | Freeman |
| 5,688,225 A | 11/1997 | Walker |
| 5,688,236 A | 11/1997 | Gragg |
| 5,701,917 A | 12/1997 | Khouri |
| D389,581 S | 1/1998 | Fein |
| 5,704,648 A | 1/1998 | Brown et al. |
| 5,707,499 A | 1/1998 | Joshi et al. |
| 5,713,881 A | 2/1998 | Rezai et al. |
| 5,714,225 A | 2/1998 | Hansen et al. |
| 5,716,411 A | 2/1998 | Orgill et al. |
| 5,733,305 A | 3/1998 | Fleischmann |
| 5,733,337 A | 3/1998 | Carr et al. |
| 5,759,570 A | 6/1998 | Arnold |
| 5,769,725 A | 6/1998 | Ogden et al. |
| 5,785,688 A | 7/1998 | Joshi et al. |
| 5,786,682 A | 7/1998 | Aiken et al. |
| 5,792,090 A | 8/1998 | Ladin |
| 5,795,584 A | 8/1998 | Totakura et al. |
| 5,810,755 A | 9/1998 | LeVeen et al. |
| 5,827,246 A | 10/1998 | Bowen |
| 5,830,176 A | 11/1998 | Mackool |
| 5,830,496 A | 11/1998 | Freeman |
| 5,833,646 A | 11/1998 | Masini |
| 5,840,777 A | 11/1998 | Eagles et al. |
| 5,843,011 A | 12/1998 | Lucas |
| 5,852,126 A | 12/1998 | Barnard et al. |
| 5,857,502 A | 1/1999 | Buchalter |
| 5,865,772 A | 2/1999 | George |
| 5,868,933 A | 2/1999 | Patrick et al. |
| 5,876,387 A | 3/1999 | Killian et al. |
| 5,876,611 A | 3/1999 | Shettigar |
| 5,885,237 A | 3/1999 | Kadash |
| 5,893,368 A | 4/1999 | Sugerman |
| 5,899,893 A | 5/1999 | Dyer et al. |
| 5,904,659 A | 5/1999 | Duarte |
| 5,911,222 A | 6/1999 | Lawrence et al. |
| 5,922,422 A | 7/1999 | Otruba |
| 5,928,265 A | 7/1999 | Fleischmann |
| 5,938,626 A | 8/1999 | Sugerman |
| 5,941,859 A | 8/1999 | Lerman |
| 5,944,703 A | 8/1999 | Dixon et al. |

(56) References Cited

U.S. PATENT DOCUMENTS

| | | |
|---|---|---|
| 5,954,680 A | 9/1999 | Augustine |
| 5,958,420 A | 9/1999 | Jenson |
| 5,964,723 A | 10/1999 | Augustine |
| 5,970,266 A | 10/1999 | Takato |
| 5,981,822 A | 11/1999 | Addison |
| 5,985,990 A | 11/1999 | Kantner et al. |
| 5,998,694 A | 12/1999 | Jensen et al. |
| 6,035,568 A | 3/2000 | Grosskopf et al. |
| 6,042,560 A | 3/2000 | Niederberger |
| 6,045,541 A | 4/2000 | Matsumoto |
| D424,236 S | 5/2000 | Reed |
| D424,699 S | 5/2000 | Allen |
| 6,071,267 A | 6/2000 | Zamierowski |
| 6,087,549 A | 7/2000 | Flick |
| 6,103,951 A | 8/2000 | Freeman |
| 6,110,197 A | 8/2000 | Augustine et al. |
| D430,674 S | 9/2000 | Dunshee et al. |
| 6,113,548 A | 9/2000 | deBoisblanc et al. |
| 6,117,111 A | 9/2000 | Fleischmann |
| 6,117,444 A | 9/2000 | Orgill et al. |
| 6,135,116 A | 10/2000 | Vogel et al. |
| 6,135,166 A | 10/2000 | Paradies et al. |
| D434,150 S | 11/2000 | Tumey |
| 6,142,982 A | 11/2000 | Hunt |
| 6,159,160 A | 12/2000 | Hsei et al. |
| 6,168,800 B1 | 1/2001 | Dobos et al. |
| 6,170,879 B1 | 1/2001 | Rawlings |
| 6,174,306 B1 | 1/2001 | Fleischmann |
| 6,176,307 B1 | 1/2001 | Danos et al. |
| 6,179,804 B1 | 1/2001 | Satterfield |
| D439,341 S | 3/2001 | Tumey et al. |
| 6,200,596 B1 | 3/2001 | Schwartzmiller et al. |
| 6,203,563 B1 | 3/2001 | Fernandez |
| 6,225,523 B1 | 5/2001 | Masini |
| 6,229,286 B1 | 5/2001 | Tokuyama |
| 6,250,005 B1 | 6/2001 | Richards |
| 6,252,129 B1 | 6/2001 | Coffee |
| 6,254,567 B1 | 7/2001 | Treu et al. |
| 6,255,552 B1 | 7/2001 | Cummings et al. |
| 6,258,200 B1 | 7/2001 | Kassab |
| 6,261,276 B1 | 7/2001 | Reitsma |
| 6,261,283 B1 | 7/2001 | Morgan et al. |
| 6,287,521 B1 | 9/2001 | Quay et al. |
| 6,291,050 B1 | 9/2001 | Cree et al. |
| 6,293,281 B1 | 9/2001 | Shultz et al. |
| D449,891 S | 10/2001 | Moro |
| 6,332,631 B1 | 12/2001 | Kirk |
| 6,345,623 B1 | 2/2002 | Heaton et al. |
| 6,350,339 B1 | 2/2002 | Sessions |
| 6,368,311 B1 | 4/2002 | Valerio et al. |
| 6,371,976 B1 | 4/2002 | Vrzalik |
| 6,383,163 B1 | 5/2002 | Kelly et al. |
| 6,391,294 B1 | 5/2002 | Dettmar et al. |
| 6,398,761 B1 | 6/2002 | Bills et al. |
| 6,398,767 B1 | 6/2002 | Fleischmann |
| 6,402,724 B1 | 6/2002 | Smith et al. |
| 6,442,413 B1 | 8/2002 | Silver |
| 6,450,773 B1 | 9/2002 | Upton |
| 6,458,109 B1 | 10/2002 | Henley et al. |
| 6,465,708 B1 | 10/2002 | Augustine |
| 6,471,685 B1 | 10/2002 | Johnson |
| 6,471,982 B1 | 10/2002 | Lydon et al. |
| 6,481,986 B1 | 11/2002 | Silver et al. |
| 6,482,491 B1 | 11/2002 | Samuelsen et al. |
| 6,486,285 B2 | 11/2002 | Fujita |
| 6,488,643 B1 | 12/2002 | Tumey et al. |
| 6,491,684 B1 | 12/2002 | Joshi et al. |
| 6,509,391 B2 | 1/2003 | Gothjaelpsen et al. |
| 6,520,982 B1 | 2/2003 | Boynton et al. |
| 6,527,203 B2 | 3/2003 | Hurray et al. |
| 6,536,056 B1 | 3/2003 | Vrzalik et al. |
| 6,547,756 B1 | 4/2003 | Greter et al. |
| 6,553,998 B2 | 4/2003 | Heaton et al. |
| 6,557,704 B1 | 5/2003 | Randolph |
| 6,564,972 B2 | 5/2003 | Sawhney et al. |
| 6,566,833 B2 | 5/2003 | Bartlett |
| 6,569,113 B2 | 5/2003 | Wirt et al. |
| 6,571,825 B2 | 6/2003 | Stacy |
| D477,086 S | 7/2003 | Tsuruda et al. |
| 6,595,949 B1 | 7/2003 | Shapiro |
| 6,599,262 B1 | 7/2003 | Masini |
| 6,604,307 B1 | 8/2003 | Cahill et al. |
| 6,626,827 B1 | 9/2003 | Felix et al. |
| 6,626,891 B2 | 9/2003 | Ohmstede |
| 6,629,774 B1 | 10/2003 | Guruendeman |
| 6,648,862 B2 | 11/2003 | Watson |
| 6,673,028 B1 | 1/2004 | Argenta et al. |
| 6,676,610 B2 | 1/2004 | Morton et al. |
| 6,680,113 B1 | 1/2004 | Lucast et al. |
| 6,682,506 B1 | 1/2004 | Navarro |
| 6,685,681 B2 | 2/2004 | Lockwood et al. |
| 6,695,823 B1 | 2/2004 | Lina et al. |
| 6,695,824 B2 | 2/2004 | Howard et al. |
| D488,928 S | 4/2004 | Foley et al. |
| 6,730,299 B1 | 5/2004 | Tayot et al. |
| 6,732,887 B2 | 5/2004 | Bills |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,767,334 B1 | 7/2004 | Randolph |
| D495,056 S | 8/2004 | Watanabe |
| 6,775,807 B2 | 8/2004 | Lowther et al. |
| 6,787,682 B2 | 9/2004 | Gilman |
| 6,794,554 B2 | 9/2004 | Sessions et al. |
| 6,797,855 B2 | 9/2004 | Worthley |
| D497,074 S | 10/2004 | Dardashti |
| 6,800,074 B2 | 10/2004 | Henley et al. |
| 6,814,079 B2 | 11/2004 | Heaton et al. |
| 6,820,766 B2 | 11/2004 | Keller et al. |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,872,196 B1 | 3/2005 | Bryan |
| 6,904,631 B2 | 6/2005 | Vrzalik et al. |
| 6,936,037 B2 | 8/2005 | Bubb et al. |
| D509,299 S | 9/2005 | Watanabe |
| 6,942,633 B2 | 9/2005 | Odland |
| 6,942,634 B2 | 9/2005 | Odland |
| 6,945,987 B2 | 9/2005 | Beard et al. |
| 6,951,553 B2 | 10/2005 | Bubb et al. |
| 6,974,428 B2 | 12/2005 | Knutson et al. |
| 6,977,323 B1 | 12/2005 | Swenson |
| 6,979,324 B2 | 12/2005 | Byordi et al. |
| D514,103 S | 1/2006 | Huang et al. |
| 6,988,423 B2 | 1/2006 | Bolam et al. |
| D516,217 S | 2/2006 | Brown et al. |
| 6,994,702 B1 | 2/2006 | Johnson |
| 7,004,915 B2 | 2/2006 | Boynton et al. |
| 7,005,556 B1 | 2/2006 | Becker et al. |
| 7,022,113 B2 | 4/2006 | Lockwood et al. |
| 7,030,288 B2 | 4/2006 | Liedtke et al. |
| 7,041,868 B2 | 5/2006 | Greene et al. |
| 7,049,478 B1 | 5/2006 | Smith |
| 7,067,709 B2 | 6/2006 | Murata et al. |
| 7,070,584 B2 | 7/2006 | Johnson et al. |
| 7,077,832 B2 | 7/2006 | Fleischmann |
| 7,087,298 B2 | 8/2006 | Key |
| 7,087,806 B2 | 8/2006 | Scheinberg et al. |
| 7,108,683 B2 | 9/2006 | Zamierowski |
| 7,117,869 B2 | 10/2006 | Heaton et al. |
| 7,118,545 B2 | 10/2006 | Boyde |
| 7,128,735 B2 | 10/2006 | Weston |
| D532,414 S | 11/2006 | Storti et al. |
| 7,137,968 B1 | 11/2006 | Burrell et al. |
| 7,141,714 B2 | 11/2006 | Nielsen |
| 7,144,390 B1 | 12/2006 | Hanningan. et al. |
| 7,160,273 B2 | 1/2007 | Greter et al. |
| 7,175,336 B2 | 2/2007 | Voellmicke et al. |
| 7,182,758 B2 | 2/2007 | McCraw |
| 7,195,624 B2 | 3/2007 | Lockwood |
| 7,198,046 B1 | 4/2007 | Argenta et al. |
| 7,214,202 B1 | 5/2007 | Vogel et al. |

(56) References Cited

U.S. PATENT DOCUMENTS

| | | |
|---|---|---|
| 7,216,651 B2 | 5/2007 | Argenta et al. |
| D544,092 S | 6/2007 | Lewis |
| 7,235,066 B1 | 6/2007 | Narini et al. |
| 7,276,051 B1 | 10/2007 | Henley et al. |
| 7,279,612 B1 | 10/2007 | Heaton et al. |
| 7,291,762 B2 | 11/2007 | Flick |
| 7,316,672 B1 | 1/2008 | Hunt et al. |
| 7,322,971 B2 | 1/2008 | Shehada |
| 7,335,809 B2 | 2/2008 | Riesinger |
| 7,338,482 B2 | 3/2008 | Lockwood et al. |
| 7,361,184 B2 | 4/2008 | Joshi |
| 7,381,859 B2 | 6/2008 | Hunt et al. |
| 7,438,705 B2 | 10/2008 | Karpowicz et al. |
| 7,447,327 B2 | 11/2008 | Kitamura et al. |
| 7,470,830 B2 | 12/2008 | Sigurjonsson et al. |
| 7,485,112 B2 | 2/2009 | Karpowicz et al. |
| 7,494,482 B2 | 2/2009 | Orgill et al. |
| 7,507,870 B2 | 3/2009 | Nielsen et al. |
| 7,518,031 B2 | 4/2009 | Liedtke et al. |
| 7,524,286 B2 | 4/2009 | Johnson |
| 7,524,315 B2 | 4/2009 | Blott et al. |
| 7,534,240 B1 | 5/2009 | Johnson |
| 7,534,927 B2 | 5/2009 | Lockwood et al. |
| 7,540,848 B2 | 6/2009 | Hannigan et al. |
| 7,553,306 B1 | 6/2009 | Hunt et al. |
| 7,569,742 B2 | 8/2009 | Haggstrom et al. |
| 7,605,298 B2 | 10/2009 | Bechert et al. |
| 7,611,500 B1 | 11/2009 | Lina et al. |
| 7,612,247 B2 | 11/2009 | Oyaski |
| 7,615,036 B2 | 11/2009 | Joshi et al. |
| 7,625,362 B2 | 12/2009 | Boehringer et al. |
| 7,645,253 B2 | 1/2010 | Gura et al. |
| 7,645,269 B2 | 1/2010 | Zamierowski |
| 7,674,837 B2 | 3/2010 | Gaserod et al. |
| 7,678,090 B2 | 3/2010 | Risk, Jr. |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,708,724 B2 | 5/2010 | Weston |
| 7,717,313 B2 | 5/2010 | Criscuolo et al. |
| 7,718,249 B2 | 5/2010 | Russell et al. |
| 7,722,582 B2 | 5/2010 | Lina et al. |
| 7,723,560 B2 | 5/2010 | Lockwood et al. |
| 7,731,702 B2 | 6/2010 | Byordi |
| 7,745,681 B1 | 6/2010 | Ferguson |
| 7,753,894 B2 | 7/2010 | Blott et al. |
| 7,758,554 B2 | 7/2010 | Lina et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,000 B2 | 7/2010 | Risk, Jr. et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,799,004 B2 | 9/2010 | Tumey |
| 7,830,980 B2 | 9/2010 | Griffiths et al. |
| 7,811,269 B2 | 10/2010 | Boynton et al. |
| 7,815,616 B2 | 10/2010 | Boehringer et al. |
| 7,825,289 B2 | 11/2010 | Vess |
| 7,828,782 B2 | 11/2010 | Suzuki |
| 7,838,717 B2 | 11/2010 | Haggstrom et al. |
| 7,846,141 B2 | 12/2010 | Weston |
| 7,862,339 B2 | 1/2011 | Mulligan |
| 7,883,494 B2 | 2/2011 | Martin |
| 7,884,258 B2 | 2/2011 | Boehringer et al. |
| 7,896,856 B2 | 3/2011 | Petrosenko et al. |
| 7,909,805 B2 * | 3/2011 | Weston ............ A61F 13/00068 604/313 |
| 7,910,791 B2 | 3/2011 | Coffey |
| 7,922,703 B2 | 4/2011 | Riesinger |
| 7,927,318 B2 | 4/2011 | Risk, Jr. et al. |
| 7,959,624 B2 | 6/2011 | Riesinger |
| 7,964,766 B2 | 6/2011 | Blott et al. |
| 7,976,519 B2 | 7/2011 | Bubb et al. |
| D642,594 S | 8/2011 | Mattson et al. |
| 7,998,125 B2 | 8/2011 | Weston |
| 8,012,169 B2 | 9/2011 | Joshi |
| 8,034,037 B2 | 10/2011 | Adams et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,084,663 B2 | 12/2011 | Watson, Jr. |
| 8,096,979 B2 | 1/2012 | Lina et al. |
| 8,100,887 B2 | 1/2012 | Weston |
| 8,105,295 B2 | 1/2012 | Blott et al. |
| 8,118,794 B2 | 2/2012 | Weston |
| 8,128,615 B2 | 3/2012 | Blott |
| 8,133,211 B2 | 3/2012 | Cavanaugh, II et al. |
| 8,147,468 B2 | 4/2012 | Barta et al. |
| 8,152,785 B2 | 4/2012 | Vitaris |
| 8,162,907 B2 | 4/2012 | Heagle |
| 8,162,909 B2 | 4/2012 | Blott et al. |
| 8,168,848 B2 | 5/2012 | Lockwood et al. |
| 8,188,331 B2 | 5/2012 | Barta et al. |
| 8,192,409 B2 | 6/2012 | Hardman et al. |
| 8,202,261 B2 | 6/2012 | Kazala, Jr. et al. |
| 8,207,392 B2 | 6/2012 | Haggstrom et al. |
| 8,235,955 B2 | 8/2012 | Blott et al. |
| 8,241,261 B2 | 8/2012 | Randolph et al. |
| 8,257,326 B2 | 9/2012 | Vitaris |
| 8,257,327 B2 | 9/2012 | Blott et al. |
| 8,282,611 B2 | 10/2012 | Weston |
| 8,303,552 B2 | 11/2012 | Weston |
| 8,338,402 B2 | 12/2012 | Fry et al. |
| 8,338,442 B2 | 12/2012 | Kumagai et al. |
| 8,348,910 B2 | 1/2013 | Blott et al. |
| 8,366,692 B2 | 2/2013 | Weston et al. |
| 8,372,049 B2 | 2/2013 | Jaeb et al. |
| 8,372,050 B2 | 2/2013 | Jaeb et al. |
| 8,398,614 B2 | 3/2013 | Blott et al. |
| 8,399,730 B2 | 3/2013 | Kazala, Jr. et al. |
| D679,819 S | 4/2013 | Peron |
| D679,820 S | 4/2013 | Peron |
| 8,409,157 B2 | 4/2013 | Haggstrom et al. |
| 8,444,612 B2 | 5/2013 | Patel et al. |
| 8,449,509 B2 * | 5/2013 | Weston ............... A61M 1/0001 604/319 |
| 8,460,255 B2 | 6/2013 | Joshi et al. |
| 8,529,548 B2 | 9/2013 | Blott et al. |
| 8,535,296 B2 | 9/2013 | Blott et al. |
| 8,540,699 B2 | 9/2013 | Miller et al. |
| D692,565 S | 10/2013 | Lattimore et al. |
| 8,545,464 B2 | 10/2013 | Weston |
| 8,551,061 B2 | 10/2013 | Hartwell |
| 8,569,566 B2 | 10/2013 | Blott et al. |
| 8,613,734 B2 | 12/2013 | Lina et al. |
| 8,628,505 B2 | 1/2014 | Weston |
| 8,641,691 B2 | 2/2014 | Fink et al. |
| 8,663,198 B2 | 3/2014 | Buan et al. |
| 8,680,360 B2 | 3/2014 | Greener et al. |
| 8,708,998 B2 | 4/2014 | Weston et al. |
| 8,715,256 B2 | 5/2014 | Greener |
| 8,758,313 B2 | 6/2014 | Blott et al. |
| 8,764,732 B2 | 7/2014 | Hartwell |
| 8,784,393 B2 | 7/2014 | Weston et al. |
| 8,791,315 B2 | 7/2014 | Lattimore et al. |
| 8,795,243 B2 | 8/2014 | Weston |
| 8,808,274 B2 | 8/2014 | Hartwell |
| 8,834,451 B2 | 9/2014 | Blott et al. |
| 8,845,619 B2 | 9/2014 | Blott et al. |
| 8,852,149 B2 | 10/2014 | Weston et al. |
| 8,882,746 B2 | 11/2014 | Blott et al. |
| 8,905,985 B2 | 12/2014 | Allen et al. |
| 8,926,592 B2 | 1/2015 | Blott et al. |
| 8,945,030 B2 | 2/2015 | Weston |
| 9,023,012 B2 | 5/2015 | Tout et al. |
| 9,044,579 B2 | 6/2015 | Blott et al. |
| 9,061,095 B2 | 6/2015 | Adie et al. |
| 9,084,845 B2 | 7/2015 | Adie et al. |

(56) References Cited

U.S. PATENT DOCUMENTS

| | | | |
|---|---|---|---|
| 9,198,801 B2 * | 12/2015 | Weston | A61F 13/00068 |
| 9,199,012 B2 | 12/2015 | Vitaris et al. | |
| 9,205,001 B2 | 12/2015 | Blott et al. | |
| 9,211,365 B2 | 12/2015 | Weston | |
| 9,272,080 B2 | 3/2016 | Weston | |
| 9,381,283 B2 | 7/2016 | Adams et al. | |
| 9,446,178 B2 | 9/2016 | Blott et al. | |
| 9,492,326 B2 | 11/2016 | Miller et al. | |
| 10,350,339 B2 * | 7/2019 | Weston | A61M 1/90 |
| 10,363,346 B2 * | 7/2019 | Weston | A61M 1/784 |
| 2001/0004082 A1 | 6/2001 | Keller et al. | |
| 2001/0016205 A1 | 8/2001 | Shimizu | |
| 2001/0027285 A1 | 10/2001 | Heinecke et al. | |
| 2001/0029956 A1 * | 10/2001 | Argenta | A61M 27/00 602/42 |
| 2001/0031943 A1 | 10/2001 | Urie | |
| 2001/0034499 A1 | 10/2001 | Sessions et al. | |
| 2001/0043943 A1 | 11/2001 | Coffey | |
| 2001/0049609 A1 | 12/2001 | Girouard et al. | |
| 2001/0051781 A1 | 12/2001 | Augustine et al. | |
| 2002/0002209 A1 | 1/2002 | Mork | |
| 2002/0038826 A1 | 4/2002 | Hurray et al. | |
| 2002/0040687 A1 | 4/2002 | van Der Lely et al. | |
| 2002/0065494 A1 * | 5/2002 | Lockwood | A61M 1/90 604/327 |
| 2002/0068913 A1 | 6/2002 | Fleischmann | |
| 2002/0082567 A1 | 6/2002 | Lockwood et al. | |
| 2002/0114847 A1 | 8/2002 | Peshoff | |
| 2002/0115952 A1 | 8/2002 | Johnson | |
| 2002/0128578 A1 | 9/2002 | Johnston et al. | |
| 2002/0143286 A1 | 10/2002 | Tumey | |
| 2002/0145007 A1 | 10/2002 | Sawhney et al. | |
| 2002/0161345 A1 | 10/2002 | McMillin | |
| 2002/0161346 A1 | 10/2002 | Lockwood et al. | |
| 2002/0183616 A1 | 12/2002 | Toews et al. | |
| 2002/0183659 A1 | 12/2002 | Krause | |
| 2002/0183702 A1 | 12/2002 | Henley et al. | |
| 2002/0198490 A1 | 12/2002 | Wirt et al. | |
| 2003/0009921 A1 | 1/2003 | McAllister | |
| 2003/0014025 A1 | 1/2003 | Allen et al. | |
| 2003/0021775 A1 | 1/2003 | Freeman | |
| 2003/0071893 A1 | 4/2003 | Miller et al. | |
| 2003/0078532 A1 | 4/2003 | Ruszczak et al. | |
| 2003/0093041 A1 | 5/2003 | Risk, Jr. et al. | |
| 2003/0097086 A1 | 5/2003 | Gura | |
| 2003/0125649 A1 | 6/2003 | Mcintosh et al. | |
| 2003/0125646 A1 | 7/2003 | Whitlock | |
| 2003/0134332 A1 | 7/2003 | Boykin | |
| 2003/0135174 A1 | 7/2003 | Benecke et al. | |
| 2003/0144619 A1 | 7/2003 | Augustine | |
| 2003/0148959 A1 | 8/2003 | Quirk et al. | |
| 2003/0171675 A1 | 9/2003 | Rosenberg | |
| 2003/0175798 A1 | 9/2003 | Raees et al. | |
| 2003/0183653 A1 | 10/2003 | Bills | |
| 2003/0211137 A1 | 11/2003 | Sierra | |
| 2003/0212357 A1 | 11/2003 | Pace | |
| 2003/0212359 A1 | 11/2003 | Butler | |
| 2003/0212431 A1 | 11/2003 | Brady et al. | |
| 2003/0216672 A1 | 11/2003 | Rastegar et al. | |
| 2003/0219469 A1 | 11/2003 | Johnson et al. | |
| 2003/0225347 A1 | 12/2003 | Argenta et al. | |
| 2004/0006319 A1 | 1/2004 | Lina et al. | |
| 2004/0019342 A1 | 1/2004 | Nagasuna et al. | |
| 2004/0033466 A1 | 2/2004 | Shellard et al. | |
| 2004/0039391 A1 | 2/2004 | Argenta et al. | |
| 2004/0039415 A1 | 2/2004 | Zamierowski | |
| 2004/0050411 A1 | 3/2004 | Lawrence | |
| 2004/0057855 A1 | 3/2004 | Gerlach et al. | |
| 2004/0064111 A1 | 4/2004 | Lockwood et al. | |
| 2004/0064132 A1 | 4/2004 | Boehringer et al. | |
| 2004/0093026 A1 | 5/2004 | Weidenhagen et al. | |
| 2004/0105230 A1 | 6/2004 | Lin | |
| 2004/0121438 A1 | 6/2004 | Quirk | |
| 2004/0122434 A1 | 6/2004 | Argenta et al. | |
| 2004/0138601 A1 | 7/2004 | Chalmers | |
| 2004/0162512 A1 | 8/2004 | Liedtke et al. | |
| 2004/0166277 A1 | 8/2004 | Key | |
| 2004/0167482 A1 | 8/2004 | Watson | |
| 2004/0167617 A1 | 8/2004 | Voellmicke et al. | |
| 2004/0171998 A1 | 9/2004 | Marasco, Jr. | |
| 2004/0193218 A1 | 9/2004 | Butler | |
| 2004/0224115 A1 | 11/2004 | Weissman et al. | |
| 2004/0241213 A1 | 12/2004 | Bray | |
| 2004/0241214 A1 | 12/2004 | Kirkwood et al. | |
| 2004/0243105 A1 | 12/2004 | Swan et al. | |
| 2004/0260230 A1 | 12/2004 | Randolph | |
| 2005/0020955 A1 | 1/2005 | Sanders et al. | |
| 2005/0029976 A1 | 2/2005 | Terry et al. | |
| 2005/0070858 A1 | 3/2005 | Lockwood et al. | |
| 2005/0085795 A1 | 4/2005 | Lockwood et al. | |
| 2005/0090787 A1 | 4/2005 | Risk, Jr. et al. | |
| 2005/0113733 A1 | 5/2005 | Liedtke et al. | |
| 2005/0130299 A1 | 6/2005 | Suzuki | |
| 2005/0131327 A1 | 6/2005 | Lockwood et al. | |
| 2005/0137272 A1 | 6/2005 | Gaserod et al. | |
| 2005/0137539 A1 | 6/2005 | Biggie et al. | |
| 2005/0143697 A1 | 6/2005 | Riesinger | |
| 2005/0147562 A1 | 7/2005 | Hunter et al. | |
| 2005/0163904 A1 | 7/2005 | Walker et al. | |
| 2005/0177190 A1 | 8/2005 | Zamierowski | |
| 2005/0181163 A1 | 8/2005 | Kose | |
| 2005/0229450 A1 | 10/2005 | Larsen et al. | |
| 2005/0230422 A1 | 10/2005 | Muller et al. | |
| 2005/0269374 A1 | 12/2005 | Koerner et al. | |
| 2006/0001382 A1 | 1/2006 | Nomoto | |
| 2006/0009744 A1 | 1/2006 | Edrman et al. | |
| 2006/0029650 A1 | 2/2006 | Coffey | |
| 2006/0029675 A1 | 2/2006 | Ginther | |
| 2006/0069365 A1 | 3/2006 | Sperl et al. | |
| 2006/0070458 A1 | 4/2006 | Jones et al. | |
| 2006/0142687 A1 | 6/2006 | Liedtke et al. | |
| 2006/0173253 A1 | 8/2006 | Ganapathy et al. | |
| 2006/0178608 A1 | 8/2006 | Stapf | |
| 2006/0241689 A1 | 10/2006 | Leiboff et al. | |
| 2006/0273109 A1 | 12/2006 | Keller | |
| 2007/0014837 A1 | 1/2007 | Johnson et al. | |
| 2007/0021697 A1 | 1/2007 | Ginther et al. | |
| 2007/0038172 A1 | 2/2007 | Zamierowski | |
| 2007/0055209 A1 | 3/2007 | Patel et al. | |
| 2007/0073200 A1 | 3/2007 | Hannigan et al. | |
| 2007/0142761 A1 | 6/2007 | Aali | |
| 2007/0167927 A1 | 7/2007 | Hunt et al. | |
| 2007/0185463 A1 | 8/2007 | Mulligan | |
| 2007/0219497 A1 | 9/2007 | Blott et al. | |
| 2007/0219513 A1 | 9/2007 | Lina et al. | |
| 2007/0225663 A1 | 9/2007 | Watt et al. | |
| 2007/0233022 A1 | 10/2007 | Henley et al. | |
| 2007/0237811 A1 | 10/2007 | Scherr | |
| 2007/0292488 A1 | 12/2007 | Bassiri et al. | |
| 2008/0004559 A1 | 1/2008 | Riesinger | |
| 2008/0069855 A1 | 3/2008 | Bonutti | |
| 2008/0095979 A1 | 4/2008 | Hatanaka et al. | |
| 2008/0119802 A1 | 5/2008 | Reisinger | |
| 2008/0132819 A1 | 6/2008 | Radl et al. | |
| 2008/0167593 A1 | 7/2008 | Fleischmann | |
| 2008/0188820 A1 | 8/2008 | Joshi | |
| 2008/0213344 A1 | 9/2008 | McCarthy et al. | |
| 2008/0223378 A1 | 9/2008 | Henderson et al. | |
| 2008/0243044 A1 | 10/2008 | Hunt et al. | |
| 2008/0294147 A1 | 11/2008 | Radl et al. | |
| 2008/0306456 A1 | 12/2008 | Riesinger | |
| 2009/0054855 A1 | 2/2009 | Blott et al. | |
| 2009/0082740 A1 | 3/2009 | Lockwood et al. | |
| 2009/0099519 A1 | 4/2009 | Kaplan | |
| 2009/0105671 A1 | 4/2009 | Daggar et al. | |
| 2009/0124988 A1 | 5/2009 | Coulthard | |
| 2009/0130186 A1 | 5/2009 | McCarthy et al. | |
| 2009/0131888 A1 | 5/2009 | Joshi | |
| 2009/0131892 A1 | 5/2009 | Karpowicz et al. | |
| 2009/0137973 A1 | 5/2009 | Karpowicz et al. | |
| 2009/0143753 A1 | 6/2009 | Blott et al. | |
| 2009/0177136 A1 | 7/2009 | Liedtke et al. | |
| 2009/0204085 A1 | 8/2009 | Biggie et al. | |
| 2009/0216170 A1 | 8/2009 | Robinson et al. | |

(56) References Cited

U.S. PATENT DOCUMENTS

| | | |
|---|---|---|
| 2009/0221977 A1 | 9/2009 | Blott et al. |
| 2009/0227968 A1 | 9/2009 | Vess |
| 2009/0234260 A1 | 9/2009 | Coward et al. |
| 2009/0234306 A1 | 9/2009 | Vitaris |
| 2009/0240185 A1 | 9/2009 | Jaeb et al. |
| 2009/0240218 A1 | 9/2009 | Braga et al. |
| 2009/0270820 A1 | 10/2009 | Johnson et al. |
| 2009/0275872 A1 | 11/2009 | Addison et al. |
| 2009/0299251 A1 | 12/2009 | Buan |
| 2009/0299255 A1 | 12/2009 | Kazala, Jr. et al. |
| 2009/0299257 A1 | 12/2009 | Long et al. |
| 2009/0299306 A1 | 12/2009 | Buan |
| 2009/0312723 A1 | 12/2009 | Blott et al. |
| 2009/0312727 A1 | 12/2009 | Heaton |
| 2010/0022972 A1 | 1/2010 | Lina et al. |
| 2010/0036334 A1 | 2/2010 | Heagle et al. |
| 2010/0036367 A1 | 2/2010 | Krohn |
| 2010/0063484 A1 | 3/2010 | Heagle |
| 2010/0069829 A1 | 3/2010 | Hutchinson et al. |
| 2010/0069858 A1 | 3/2010 | Olson |
| 2010/0069863 A1 | 3/2010 | Olson |
| 2010/0069885 A1 | 3/2010 | Stevenson et al. |
| 2010/0106117 A1 | 4/2010 | Lockwood et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0135915 A1 | 6/2010 | Greener et al. |
| 2010/0210986 A1 | 8/2010 | Sanders et al. |
| 2010/0211030 A1 | 8/2010 | Turner et al. |
| 2010/0249733 A9 | 9/2010 | Blott et al. |
| 2010/0262090 A1 | 10/2010 | Riesinger |
| 2010/0298866 A1 | 11/2010 | Fischvogt |
| 2010/0305490 A1 | 12/2010 | Coulthard et al. |
| 2010/0305524 A1 | 12/2010 | Vess et al. |
| 2010/0305526 A1 | 12/2010 | Robinson et al. |
| 2010/0324510 A1 | 12/2010 | Andresen et al. |
| 2010/0324516 A1 | 12/2010 | Braga et al. |
| 2011/0004171 A1 | 1/2011 | Blott et al. |
| 2011/0004172 A1 | 1/2011 | Eckstein et al. |
| 2011/0034892 A1 | 2/2011 | Buan |
| 2011/0054422 A1 | 3/2011 | Locke et al. |
| 2011/0054423 A1 | 3/2011 | Blott et al. |
| 2011/0092927 A1 | 4/2011 | Wilkes et al. |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0172612 A1 | 7/2011 | Greener |
| 2011/0172617 A1 | 7/2011 | Riesinger |
| 2011/0178451 A1 | 7/2011 | Robinson et al. |
| 2011/0224631 A1 | 9/2011 | Simmons |
| 2011/0230849 A1 | 9/2011 | Coulthard et al. |
| 2012/0004628 A1 | 1/2012 | Blott et al. |
| 2012/0053538 A1 | 3/2012 | Blott et al. |
| 2012/0083755 A1 | 4/2012 | Lina et al. |
| 2012/0123356 A1 | 5/2012 | Greener |
| 2013/0096519 A1 | 4/2013 | Blott |
| 2013/0116635 A1 | 5/2013 | Fleischmann |
| 2013/0116641 A1 | 5/2013 | Hicks |
| 2013/0138054 A1 | 5/2013 | Fleishchmann |
| 2013/0150814 A1 | 6/2013 | Buan |
| 2013/0274688 A1 | 10/2013 | Weston |
| 2014/0018753 A1 | 1/2014 | Ashok et al. |
| 2014/0094761 A1 | 4/2014 | Corley |
| 2014/0228791 A1 | 8/2014 | Hartwell |
| 2014/0236109 A1 | 8/2014 | Greener |
| 2014/0249493 A1 | 9/2014 | Hartwell |
| 2014/0371691 A1 | 12/2014 | Blott et al. |
| 2015/0057625 A1 | 2/2015 | Coulthard et al. |
| 2015/0065966 A1 | 3/2015 | Adie et al. |
| 2015/0073361 A1 | 3/2015 | Pratt et al. |
| 2015/0080788 A1 | 3/2015 | Blott et al. |
| 2015/0157508 A1 | 6/2015 | Blott et al. |
| 2015/0165101 A1 | 6/2015 | Blott et al. |
| 2015/0173954 A1 | 6/2015 | Blott et al. |
| 2015/0174306 A1 | 6/2015 | Blott et al. |
| 2015/0209492 A1 | 7/2015 | Blott et al. |
| 2016/0206790 A1 | 7/2016 | Weston |
| 2019/0091383 A1 | 3/2019 | Weston |

FOREIGN PATENT DOCUMENTS

| | | |
|---|---|---|
| CA | 1305587 C | 6/1988 |
| CA | 2057000 C | 5/1990 |
| CA | 2115746 | 8/1992 |
| CA | 1309560 | 11/1992 |
| CA | 1309560 C | 11/1992 |
| CA | 1320888 | 8/1993 |
| CA | 2198243 A1 | 2/1996 |
| CA | 2214804 A1 | 2/1996 |
| CA | 2240732 | 12/1996 |
| CA | 2238413 A1 | 5/1997 |
| CA | 2551340 A1 | 5/1997 |
| CA | 2280808 A1 | 2/1998 |
| CA | 2285470 A1 | 9/1998 |
| CA | 2331555 A1 | 6/1999 |
| CA | 2367460 A1 | 10/2000 |
| CA | 2369022 C | 10/2000 |
| CA | 2369024 A1 | 10/2000 |
| CA | 2390513 A1 | 5/2001 |
| CA | 2121688 C | 7/2001 |
| CA | 2369022 A1 | 10/2001 |
| CA | 2408305 A1 | 11/2001 |
| CA | 2254999 C | 4/2002 |
| CA | 2042768 C | 8/2002 |
| CA | 2442724 A1 | 10/2002 |
| CA | 2432293 A1 | 2/2003 |
| CA | 2458285 A1 | 3/2003 |
| CA | 2157772 C | 9/2003 |
| CA | 2490027 A1 | 12/2003 |
| CA | 2486274 A1 | 9/2004 |
| CA | 2349638 C | 6/2005 |
| CA | 2216791 C | 7/2005 |
| CN | 1514739 A | 7/2004 |
| CN | 1921897 A | 2/2007 |
| CN | 1960690 A | 5/2007 |
| DE | 561757 C | 10/1932 |
| DE | 847475 C | 8/1952 |
| DE | 2 809 828 A1 | 9/1978 |
| DE | 3 137 839 A1 | 3/1983 |
| DE | 3 539 533 | 5/1987 |
| DE | 3 935 818 A1 | 5/1991 |
| DE | 4 012 232 A1 | 10/1991 |
| DE | 4 016 034 A1 | 11/1991 |
| DE | 4 102 684 | 8/1992 |
| DE | 4 111 122 | 4/1993 |
| DE | 2 950 4378 | 10/1995 |
| DE | 2 961 8426 U1 | 2/1997 |
| DE | 1 963 0690 | 2/1998 |
| DE | 198 44 355 | 4/2000 |
| DE | 20 2004 017 052 | 7/2005 |
| DE | 202005019670 U1 | 12/2005 |
| DE | 3 032 092 A1 | 8/2008 |
| EP | 0053936 A2 | 6/1982 |
| EP | 0 020 662 B1 | 7/1984 |
| EP | 0147119 A2 | 7/1985 |
| EP | 0 099 748 B1 | 5/1987 |
| EP | 0 122 085 B1 | 6/1987 |
| EP | 0 340 018 | 11/1989 |
| EP | 0 355 186 A1 | 2/1990 |
| EP | 0 355 536 A2 | 2/1990 |
| EP | 0 358 302 A2 | 3/1990 |
| EP | 0 418 607 A1 | 3/1991 |
| EP | 0 485 657 A1 | 5/1992 |
| EP | 0 521 434 A1 | 1/1993 |
| EP | 0 325 771 B1 | 9/1993 |
| EP | 0 617 938 A1 | 3/1994 |
| EP | 0 425 164 A1 | 9/1994 |
| EP | 0 619 105 A1 | 10/1994 |
| EP | 0 638 301 A1 | 2/1995 |
| EP | 0 648 122 A1 | 4/1995 |
| EP | 0 392 640 B1 | 6/1995 |
| EP | 0 441 418 | 7/1995 |
| EP | 0 777 504 B1 | 8/1995 |

(56) References Cited

FOREIGN PATENT DOCUMENTS

| | | |
|---|---|---|
| EP | 0 853 950 B1 | 8/1995 |
| EP | 0 670 705 A1 | 9/1995 |
| EP | 0 690 736 A1 | 1/1996 |
| EP | 0 724 888 A1 | 8/1996 |
| EP | 0 733 375 A2 | 9/1996 |
| EP | 0 465 601 B1 | 1/1997 |
| EP | 0 754 064 A1 | 1/1997 |
| EP | 0 762 860 A1 | 3/1997 |
| EP | 0 772 464 A1 | 5/1997 |
| EP | 0 762 860 B1 | 12/1997 |
| EP | 0 537 559 B1 | 1/1998 |
| EP | 0 620 720 B1 | 3/1998 |
| EP | 0 880 953 B1 | 5/1998 |
| EP | 0 856 318 A1 | 8/1998 |
| EP | 0 858 810 A2 | 8/1998 |
| EP | 0 651 983 B1 | 9/1998 |
| EP | 0 876 165 A1 | 11/1998 |
| EP | 0 888 141 A1 | 1/1999 |
| EP | 0 912 251 A1 | 5/1999 |
| EP | 0 782 421 B1 | 7/1999 |
| EP | 1 068 451 A1 | 10/1999 |
| EP | 1 007 015 A1 | 6/2000 |
| EP | 1 013 290 A1 | 6/2000 |
| EP | 1 021 180 A1 | 7/2000 |
| EP | 1 029 585 A1 | 8/2000 |
| EP | 1 030 657 A1 | 8/2000 |
| EP | 0 688 189 B1 | 9/2000 |
| EP | 0 993 833 A3 | 10/2000 |
| EP | 1 169 071 A1 | 10/2000 |
| EP | 0 690 706 B1 | 11/2000 |
| EP | 1 085 925 A1 | 3/2001 |
| EP | 1 088 569 A2 | 4/2001 |
| EP | 1 088 589 A | 4/2001 |
| EP | 1 105 110 A1 | 6/2001 |
| EP | 1 105 171 A2 | 6/2001 |
| EP | 1 105 180 A1 | 6/2001 |
| EP | 1 107 813 A1 | 6/2001 |
| EP | 0 865 304 B1 | 7/2001 |
| EP | 1 411 874 A1 | 7/2001 |
| EP | 1 138 336 A1 | 10/2001 |
| EP | 1 156 839 A1 | 11/2001 |
| EP | 1 283 702 A1 | 11/2001 |
| EP | 0 921 775 B1 | 12/2001 |
| EP | 0 564 502 B1 | 1/2002 |
| EP | 1 339 366 A2 | 6/2002 |
| EP | 0 875 222 B1 | 7/2002 |
| EP | 1 218 437 A1 | 7/2002 |
| EP | 1 219 311 | 7/2002 |
| EP | 0 853 950 B1 | 10/2002 |
| EP | 1 306 123 A1 | 2/2003 |
| EP | 0 708 620 B1 | 5/2003 |
| EP | 1 088 569 B1 | 8/2003 |
| EP | 0 993 317 B1 | 9/2003 |
| EP | 1 565 219 A2 | 12/2003 |
| EP | 1 219 311 B1 | 7/2004 |
| EP | 1 440 737 A1 | 7/2004 |
| EP | 1 018 967 B1 | 8/2004 |
| EP | 1 488 816 A1 | 12/2004 |
| EP | 1 578 477 A2 | 9/2005 |
| EP | 1 440 667 B1 | 3/2006 |
| EP | 1 632 252 A1 | 3/2006 |
| EP | 1 284 777 B1 | 4/2006 |
| EP | 1 263 366 B1 | 7/2006 |
| EP | 0 982 015 B1 | 8/2006 |
| EP | 0 620 720 B2 | 11/2006 |
| EP | 1 923 077 B1 | 11/2006 |
| EP | 1 904 137 A2 | 1/2007 |
| EP | 1 448 261 B1 | 2/2007 |
| EP | 1 171 065 B1 | 3/2007 |
| EP | 1 880 840 A1 | 1/2008 |
| EP | 2 059 204 A2 | 1/2008 |
| EP | 1 476 217 B1 | 3/2008 |
| EP | 1 897 569 A1 | 3/2008 |
| EP | 2 106 255 A2 | 7/2008 |
| EP | 1 955 887 | 8/2008 |
| EP | 2 109 472 A1 | 8/2008 |
| EP | 1 121 163 | 11/2008 |
| EP | 2 185 206 A2 | 1/2009 |
| EP | 2 178 573 A2 | 2/2009 |
| EP | 2 203 137 A1 | 4/2009 |
| EP | 1 772 160 B1 | 6/2009 |
| EP | 2 098 257 | 9/2009 |
| EP | 2 244 746 A2 | 9/2009 |
| EP | 2 254 537 A2 | 9/2009 |
| EP | 2 111 804 A2 | 10/2009 |
| EP | 1 513 478 B1 | 12/2009 |
| EP | 1 985 270 A3 | 12/2009 |
| EP | 1 637 088 B1 | 1/2010 |
| EP | 2 326 295 A1 | 3/2010 |
| EP | 2 172 164 A1 | 4/2010 |
| EP | 2 253 353 A1 | 11/2010 |
| EP | 2 255 837 A1 | 12/2010 |
| EP | 2 004 116 B1 | 6/2011 |
| EP | 2 349 155 A2 | 8/2011 |
| EP | 1 263 366 B2 | 9/2011 |
| EP | 2 420 214 A1 | 2/2012 |
| EP | 2 021 046 | 3/2012 |
| EP | 2 462 908 A1 | 6/2012 |
| EP | 2 648 668 | 1/2015 |
| EP | 2 836 711 | 2/2015 |
| EP | 2 814 556 | 7/2015 |
| EP | 2 079 507 B1 | 11/2016 |
| FR | 1 163 907 | 5/1958 |
| GB | 114754 | 4/1918 |
| GB | 236350 | 7/1925 |
| GB | 641061 | 8/1950 |
| GB | 1063066 A | 3/1967 |
| GB | 1224009 A | 3/1971 |
| GB | 1255395 | 12/1971 |
| GB | 1273342 A | 5/1972 |
| GB | 1400124 A | 7/1975 |
| GB | 1522086 A | 8/1978 |
| GB | 1549756 A | 8/1979 |
| GB | 2041756 | 9/1980 |
| GB | 2085305 A | 1/1985 |
| GB | 2195255 A | 4/1988 |
| GB | 2235877 | 3/1991 |
| GB | 2272917 A | 6/1994 |
| GB | 2288734 A | 11/1995 |
| GB | 2306437 | 5/1997 |
| GB | 2307180 A | 5/1997 |
| GB | 2329127 | 3/1999 |
| GB | 2305610 B | 7/1999 |
| GB | 2336546 B2 | 6/2000 |
| GB | 2344531 A | 6/2000 |
| GB | 2378392 A | 2/2003 |
| GB | 2357286 B | 11/2003 |
| GB | 2389794 A1 | 12/2003 |
| GB | 2365350 B | 8/2004 |
| GB | 2415908 A | 1/2006 |
| GB | 2418738 A | 4/2006 |
| GB | 2422545 A | 8/2006 |
| GB | 2423019 A | 8/2006 |
| GB | 2424581 A | 10/2006 |
| GB | 2424582 A | 10/2006 |
| GB | 2435419 A | 2/2007 |
| JP | 59-502014 A | 12/1984 |
| JP | H08-024344 A | 1/1996 |
| JP | H11-069660 A | 3/1999 |
| JP | 2001-314479 A | 11/2001 |
| JP | 2002-035133 A | 2/2002 |
| JP | 2003-165843 A | 6/2003 |
| JP | 2004-121819 A | 4/2004 |
| JP | 2005-261376 A | 9/2005 |
| JP | 2006-262647 A | 9/2006 |
| JP | 2008119497 A | 5/2008 |
| NL | 1 005 726 C2 | 10/1998 |
| RU | 240188 | 3/1969 |
| SE | 429720 | 9/1983 |
| SU | 1251912 A1 | 8/1986 |
| SU | 1762940 A1 | 9/1992 |
| WO | WO 1980/01139 | 6/1980 |
| WO | WO 1980/02182 | 10/1980 |
| WO | WO 1983/00742 | 3/1983 |

(56) References Cited

FOREIGN PATENT DOCUMENTS

| | | |
|---|---|---|
| WO | WO 1984/01904 | 5/1984 |
| WO | WO 1987/00759 | 2/1987 |
| WO | WO 1987/04626 | 8/1987 |
| WO | WO 1989/05133 | 6/1989 |
| WO | WO 1990/10424 | 9/1990 |
| WO | WO 1990/11795 | 10/1990 |
| WO | WO 1991/00718 | 1/1991 |
| WO | WO 1991/16030 | 10/1991 |
| WO | WO-9200299 A1 | 1/1992 |
| WO | WO 1992/09651 | 6/1992 |
| WO | WO 1992/13713 | 8/1992 |
| WO | WO 1992/19313 | 11/1992 |
| WO | WO 1992/20299 | 11/1992 |
| WO | WO 1993/00056 | 1/1993 |
| WO | WO 1993/06802 | 4/1993 |
| WO | WO 1993/09176 | 5/1993 |
| WO | WO 1993/09727 | 5/1993 |
| WO | WO 1994/20041 | 9/1994 |
| WO | WO 1994/020133 | 9/1994 |
| WO | WO 1995/03838 | 2/1995 |
| WO | WO 1996/00760 | 1/1996 |
| WO | WO 1996/05873 | 2/1996 |
| WO | WO 1996/24316 | 8/1996 |
| WO | WO 1996/040174 | 12/1996 |
| WO | WO 1997/003717 | 2/1997 |
| WO | WO 1997/05685 | 2/1997 |
| WO | WO 1997/13520 | 4/1997 |
| WO | WO 1997/18737 | 5/1997 |
| WO | WO 1997/033643 | 9/1997 |
| WO | WO 1997/033922 | 9/1997 |
| WO | WO 1997/042986 | 11/1997 |
| WO | WO 1997/043991 | 11/1997 |
| WO | WO 1998/06444 | 2/1998 |
| WO | WO 1998/013000 | 4/1998 |
| WO | WO 1998/038955 | 9/1998 |
| WO | WO 1999/01173 | 1/1999 |
| WO | WO 1999/13793 | 3/1999 |
| WO | WO 1999/15121 | 4/1999 |
| WO | WO 1999/017698 | 4/1999 |
| WO | WO 1999/23010 | 5/1999 |
| WO | WO 1999/030629 | 6/1999 |
| WO | WO 1999/047097 | 9/1999 |
| WO | WO 1999/64081 | 12/1999 |
| WO | WO 1999/065536 | 12/1999 |
| WO | WO 2000/07653 | 2/2000 |
| WO | WO 2000/09199 | 2/2000 |
| WO | WO 2000/21586 | 4/2000 |
| WO | WO 2000/038752 | 7/2000 |
| WO | WO 2000/50143 | 8/2000 |
| WO | WO 2000/59418 | 10/2000 |
| WO | WO 2000/59424 | 10/2000 |
| WO | WO 2000/61046 | 10/2000 |
| WO | WO 2000/061206 | 10/2000 |
| WO | WO 2000/062827 | 10/2000 |
| WO | WO 2000/064396 | 11/2000 |
| WO | WO 2001/005443 | 1/2001 |
| WO | WO 2001/19430 | 3/2001 |
| WO | WO 2001/024709 | 4/2001 |
| WO | WO 2001/34223 | 5/2001 |
| WO | WO 2001/35882 | 5/2001 |
| WO | WO 2001/37773 | 5/2001 |
| WO | WO 2001/37922 A2 | 5/2001 |
| WO | WO 2001/37922 A3 | 5/2001 |
| WO | WO 2001/041779 | 6/2001 |
| WO | WO 2001/49233 | 7/2001 |
| WO | WO 2001/062312 | 8/2001 |
| WO | WO 2001/066017 | 9/2001 |
| WO | WO 2001/85248 | 11/2001 |
| WO | WO 2001/93793 | 12/2001 |
| WO | WO 2002/000268 | 1/2002 |
| WO | WO 2002/002079 | 1/2002 |
| WO | WO 2002/05737 | 1/2002 |
| WO | WO 2002/09765 | 2/2002 |
| WO | WO 2002/20026 | 3/2002 |
| WO | WO 2002/26180 | 4/2002 |
| WO | WO 2002/034304 | 5/2002 |
| WO | WO 2002/39940 | 5/2002 |
| WO | WO 2002/41878 | 5/2002 |
| WO | WO 2002/45761 | 6/2002 |
| WO | WO 2002/064182 | 8/2002 |
| WO | WO 2002/076834 | 10/2002 |
| WO | WO 2002/083046 | 10/2002 |
| WO | WO 2002/091965 | 11/2002 |
| WO | WO 2002/092783 | 11/2002 |
| WO | WO 2002/094256 | 11/2002 |
| WO | WO 2002/102864 | 12/2002 |
| WO | WO 2003/005943 | 1/2003 |
| WO | WO 2003/009796 | 2/2003 |
| WO | WO 2003/018098 | 3/2003 |
| WO | WO 2003/020358 | 3/2003 |
| WO | WO 2003/030966 | 4/2003 |
| WO | WO 2003/041686 | 5/2003 |
| WO | WO 2003/045492 | 6/2003 |
| WO | WO 2003/057070 | 7/2003 |
| WO | WO 2003/057307 | 7/2003 |
| WO | WO 2003/063923 | 8/2003 |
| WO | WO 2003/070135 | 8/2003 |
| WO | WO 2003/071991 | 9/2003 |
| WO | WO 2003/073970 | 9/2003 |
| WO | WO 2003/086232 | 10/2003 |
| WO | WO 2003/092620 | 11/2003 |
| WO | WO 2003/074100 | 12/2003 |
| WO | WO 2003/101385 | 12/2003 |
| WO | WO 2003/101508 | 12/2003 |
| WO | WO 2004/012678 | 2/2004 |
| WO | WO 2004/018020 | 3/2004 |
| WO | WO 2004/024300 | 3/2004 |
| WO | WO 2004/032977 | 4/2004 |
| WO | WO 2004/037334 | 5/2004 |
| WO | WO 2004/045498 | 6/2004 |
| WO | WO 2004/054632 | 7/2004 |
| WO | WO 2004/077387 | 9/2004 |
| WO | WO 2004/091370 | 10/2004 |
| WO | WO 2005/009225 | 2/2005 |
| WO | WO 2005/009488 | 2/2005 |
| WO | WO 2005/016179 | 2/2005 |
| WO | WO 2005/017000 | 2/2005 |
| WO | WO 2005/018695 | 3/2005 |
| WO | WO 2005/025447 | 3/2005 |
| WO | WO 2005/025666 | 3/2005 |
| WO | WO 2005/034875 | 4/2005 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/070480 | 8/2005 |
| WO | WO 2005/082435 | 9/2005 |
| WO | WO 2005/105174 | 11/2005 |
| WO | WO 2005/105175 | 11/2005 |
| WO | WO 2005/105176 | 11/2005 |
| WO | WO 2005/105180 | 11/2005 |
| WO | WO 2005/115497 | 12/2005 |
| WO | WO 2005/123170 | 12/2005 |
| WO | WO 2006/014764 | 2/2006 |
| WO | WO 2006/052839 | 5/2006 |
| WO | WO 2006/056294 | 6/2006 |
| WO | WO 2006/081403 | 8/2006 |
| WO | WO 2006/130594 | 12/2006 |
| WO | WO 2006/135934 | 12/2006 |
| WO | WO 2007/013064 | 2/2007 |
| WO | WO 2007/019038 | 2/2007 |
| WO | WO 2007/030601 | 3/2007 |
| WO | WO 2007/075379 | 7/2007 |
| WO | WO 2008/010094 | 1/2008 |
| WO | WO 2008/014358 | 1/2008 |
| WO | WO 2008/030872 | 3/2008 |
| WO | WO 2008/036360 | 3/2008 |
| WO | WO 2008/039839 | 4/2008 |
| WO | WO 2008/040681 | 4/2008 |
| WO | WO 2008/064503 | 6/2008 |
| WO | WO 2008/086397 | 7/2008 |
| WO | WO 2008/104609 | 9/2008 |
| WO | WO 2008/131896 | 11/2008 |
| WO | WO 2009/011856 | 1/2009 |

(56) References Cited

FOREIGN PATENT DOCUMENTS

| | | |
|---|---|---|
| WO | WO 2009/019415 | 2/2009 |
| WO | WO 2009/019496 | 2/2009 |
| WO | WO 2009/021523 | 2/2009 |
| WO | WO 2009/066105 | 5/2009 |
| WO | WO 2009/066106 | 5/2009 |
| WO | WO 2009/070905 | 6/2009 |
| WO | WO 2009/124100 | 10/2009 |
| WO | WO 2009/158128 | 12/2009 |
| WO | WO 2009/158131 | 12/2009 |
| WO | WO 2010/016791 | 2/2010 |
| WO | WO 2010/033271 | 3/2010 |
| WO | WO 2010/033574 | 3/2010 |
| WO | WO 2010/033613 | 3/2010 |
| WO | WO 2010/051068 | 5/2010 |
| WO | WO 2010/051073 | 5/2010 |
| WO | WO 2010/072309 | 7/2010 |
| WO | WO 2010/142959 | 12/2010 |
| WO | WO 2010/147533 | 12/2010 |
| WO | WO 2012/001371 | 1/2012 |
| WO | WO 2012/069793 | 5/2012 |
| WO | WO 2012/069794 | 5/2012 |
| WO | WO 2013/123005 | 8/2013 |

OTHER PUBLICATIONS

US 6,306,115 B1, 10/2001, Kelly et al. (withdrawn)
Brief Communication—Letter from the Proprietor of the Patent, re the Opposition of European Patent No. 3246054, dated Nov. 13, 2020, 5 pages.
Brief Communication, Letter from the Opponent for Opposition of European Patent No. 3246054, dated Dec. 22, 2020, 2 pages.
Brief Communication, Letter from the Proprietor for Opposition of European Patent No. 3246054, dated Jul. 22, 2020, 23 pages.
Bush, G.K., "What is a Counter Irritant? Name Any That You Know and the Method of their Application," the British Journal Nursing, Oct. 1927, p. 232.
Communication of a Notice of Opposition including Statement of Facts and Evidence for European Patent No. 3246054, dated Jul. 10, 2020, 24 pages.
Communication pursuant to Rule 77(1) EPC Indicating deficiencies in the notice of opposition for European Patent No. 3246054, dated Jul. 24, 2020, 5 pages.
Communication to the parties concerning the termination of the opposition proceedings for European Patent No. 3246054, dated May 3, 2021, 1 page.
Davydov Y.A., et al., "Vacuum Therapy in the Treatment of Purulent Lactation Mastitis," 1986, pp. 66-70.
Decision to discontinue the opposition proceedings for European Patent No. 3246054, dated Jan. 18, 2021, 2 pages.
Discussion between Mr. Kevin Cordina and Mr. Nadeem Bridi regarding Opponent's name, mailed on Dec. 11, 2019, 2 pages.
Letter regarding the opposition procedure, for European Patent No. 3246054, dated Sep. 7, 2020, 4 pages.
Notice of Opposition—Statement of Facts and Evidence for the European Patent No. 2731564, mailed on Jan. 22, 2020, 12 pages.
Notice of Opposition—Statement of Facts and Evidence, re European Patent No. 3246054, dated Feb. 13, 2020, 13 pages.
State on Oath of Kevin Cronin submitted in the Opposition against European Patent No. 3246054, signed on Sep. 3, 2020, 1 page.
Summons to Attend Oral Proceedings Pursuant to rule 115(1) EPC for European Patent No. 3246054, mailed on Dec. 15, 2020, 13 pages. <iframe class="ginger-extension-definitionpopup" src="chrome-extension://kdfieneakcjfaiglcfcgkidlkmlijjnh/content/popups/definitionPopup/index.html?title=Pursuant&description=(followed%20by%20'to')%20in%20conformance%20to%20or%20agreement%20with" style="left: 204.444px; top: 16.8889px; z-index: 2147483646; display: none;"></iframe>.
Termination of the Opposition Proceedings with Maintenance of the Patent for European Patent No. 3246054, dated Apr. 28, 2021, 1 page.
Withdrawal of an opposition by the opponent for European Patent No. 3246054, mailed on Dec. 16, 2020, 3 pages.
Invia Liberty Negative Pressure Wound Therapy (NPWT) System, Medela, accessed Apr. 10, 2018, 5 pages. URL: http://www.medela-healthcare.us/healthcare/products/npwt/invialiberty.
U.S. Appl. No. 10/599,720, filed Oct. 6, 2006, Blott et al..
U.S. Appl. No. 12/192,000, filed Apr. 14, 2008, Hartwell et al..
U.S. Appl. No. 12/260,962, filed Oct. 29, 2009, Weston.
European Supplemental Search Report, re EP Application No. 05 75 0239, dated Apr. 23, 2010 in 3 pages.
Supplementary European Search Report, re EP Application No. 05 75 0239 dated Aug. 2, 2010.
International Standard ISO 10079-1, First Edition, May 15, 1991, in 2 pages.
"General Characteristics of Wound Healing and Russian Classification of Wound Healing Process", (author and date unknown), in 5 pages.
Thomas, S., "Hydrocolloids", Journal of Wound Care, vol. 1, No. 2, Jul.-Aug. 1992, pp. 27-30, in 5 pages.
"Pleur-evac. Adult-Pediatric, Non-Metered", Code No. A-4000. Control No. F7961J, in 1 page.
3M Health Care, "Controlling the Risk of Surgical Site Infections after Cardiovascular Procedures: the Importance of Providing a Sterile Surface", Brochure, St. Paul, MN and London, Ontario, Canada, 1997, in 8 pages.
"A Sensational Medical Discovery", the British Journal of Nursing, Jul. 15, 1911, p. 42, in 1 page.
Abelson, R., "Hospitals See Possible Conflict on Medical Devices for Doctors", Sep. 22, 2005, Newspaper Article, in 1 page.
Achterberg, V. et al., "Hydroactive dressings and serum proteins: an in vitro study," Journal of Wound Care, vol. 5, No. 2, Feb. 1996, pp. 79-82, in 4 pages.
Aeros, "Moblvac II," 1 page, Aeros Instruments, Inc., Northbrook, IL Oct. 1988.
Aeros, Aeros Instruments, Inc. 1111 Lakeside Dr., Gurnee, IL 60031. Aug. 1993. "Care-E-Vac", in 2 pages.
Aeros, Aeros Instruments, Inc. 3411 Commercial Ave., Northbrook, IL 60062. Oct. 1988. Part No. 1504-02 7M. "Instavac Aspirator", in 1 page.
Aeros, "care-e-vac II", Downloaded from internet Apr. 10, 2006, in 2 pages. URL: http://www.aerosinstruments.com.
Aeros, moblvac® III, Downloaded from internet Apr. 10, 2006. URL: http://www.aerosinstruments.com.
Agarwala, S. et al., "Use of Mini-Vacuum Drains in Small Surgical Wounds", Plastic and Reconstructive Surgery, Apr. 1998, vol. 101(5), pp. 1421-1422 (Correspondence), in 2 pages.
Agrama, H.M. et al., "Functional Longevity of Intraperitoneal Drains", Amer. Journ. of Surg., Sep. 1976, vol. 132, pp. 418-421, in 4 pages.
Alexander, J., "Prevention of Wound Infections," the American Journal of Surgery, Jul. 1976, pp. 59-63, vol. 132, USA.
Alper, J.C. et al., "An Effective Dressing for a Large, Draining Abdominal Wound", *RN*, Dec. 1988, pp. 24-25, in 2 pages.
Alper, J.C. et al., "Moist Wound Healing under a Vapor Permeable Membrane", Journ. of Amer. Acad. of Derm., Mar. 1983, vol. 8(3), pp. 347-353, in 7 pages.
Alper, J., "Recent Advances in Moist Wound Healing," Southern Medical Journal, Nov. 1986, pp. 1398-1404, vol. 79, No. 11, USA, in 7 pages.
Antonic, M. et al., "Experience with the Use of Vacuum Therapy—Vacusac", Timocki Medicinski Glasnik, Year XII, Zajecar, 1987, No. 1, pp. 77-82, in 7 pages.
Appendix PA1 Hydrokolloide Verbände http:--www.pflegewiki.de-wiki-Hydrokolloide_Verbände dated Jan. 19, 2015 in 3 pages. English translation produced using Google translate on May 26, 2015.
Argenta, L. et al., "Vacuum-Assisted Closure: a New Method for Wound Control and Treatment: Clinical Experience", Ann Plas Surg, 1997, vol. 38, pp. 563-577 (Dec. 10, 1996), in 14 pages.
Arnljots, B. et al., "Irrigation Treatment in Split-Thickness Skin Grafting of Intractable Leg Ulcers," Scandinavian Journal of Plastic and Reconstructive Surgery, 1985, vol. 19, pp. 211-213, in 3 pages.

(56) References Cited

OTHER PUBLICATIONS

Article Excerpt, The Lancet, Jun. 14, 1952, pp. 1175-1176, in 2 pages.
Article Excerpt, "Part III. Resolving Selected Clinical Dilemmas", pp. 17-20, in 4 pages.
Arturson, M., "The Pathophysiology of Severe Thermal Injury", JBCR, Mar./Apr. 1985, vol. 6(2), pp. 129-146, in 17 pages.
Ashrafov, A.A. et al., "An Experimental and Clinical Validation for the Use of a Collagen Sponge for Treating the Suppurative-Inflammatory Complications of Wound Healing in Emergency Abdominal Surgery", Klin Khir, 1993, vol. 1, PubMed, abstract downloaded from internet Apr. 28, 2006, 1 page.
"Assessing the Patient with a Fistula or Draining Wounds", Nursing, Jun. 1980, pp. 49-51, in 3 pages.
Aubrey, D.A. et al., "Treatment of the Perineal Wound after Proctectomy by Intermittent Irrigation", Arch. Surg., Oct. 1984, vol. 119, pp. 1141-1144, in 4 pages.
Avocat, C. et al., "Nouvelle Presentation de Materiel Pour Drainage de Redon et Jost", La Nouvelle Presse Medicale, Jun. 26, 1976, vol. 5(6), pp. 1644-1645 (in French), in 2 pages.
Ayoub, M.H. et al., "A Study of Cutaneous and Intracompartmental Limb Pressures Associated with the Combined Use of Tourniquets and Plaster Casts", Abstract., Proc. and Reports of Univ., Colleges, Councils, Assoc., and Societies, vol. 68-B:3, May 1986, p. 497, in 1 page.
Bagautdinov, "Variant of External Vacuum Aspiration in the Treatment of Purulent Diseases of Soft Tissues," Current Problems in Modern Clinical Surgery, 1986, 4 pages.
Bagautdinov, N.A. "Variant of External Vacuum Aspiration in the Treatment of Purulent Diseases of Soft Tissues," in Current Problems in Modern Clinical Surgery: Interdepartmental Collection, edited by V.Ye. Volkov et al. (Chuvashia State University, Cheboksary, USSR 1986) pp. 94-96.
Baldwin, J.F., Ed., The Columbus Medical Journal, Columbus, Ohio, 1887, vol. V., p. 561, in 1 page.
Barbul, A. et al., Eds., Clinical and Experimental Approaches to Dermal and Epidermal Repair—Normal and Chronic Wounds, Progress in Clin. and Biol. Res., vol. 365, Proc. of the 3rd Intnl. Symp. on Tissue Repair, Miami, FL, Jan. 10-14, 1990, abstract, in 2 pages.
Bar-El, Y. et al., "Potentially Dangerous Negative Intrapleural Pressures Generated by Ordinary Pleural Drainage Systems", Chest, Feb. 2001, vol. 119(2), pp. 511-514.
Barker, D.E. et al., "Vacuum Pack Technique of Temporary Abdominal Closure: a 7-Year Experience with 112 Patients", *Journal of Trauma: Injury and Critical Care*, Feb. 2000, vol. 48(2), pp. 201-207, in 7 pages.
Bascom, J., "Pilonidal Sinus", Current Therapy in Colon and Rectal Surgery, 1990, pp. 1-8, in 8 pages.
Benjamin, P.J., "Feculent Peritonitis: a Complication of Vacuum Drainage", Br. J. Surg., 1980, vol. 67, pp. 453-454, in 2 pages.
Berman, A. et al., "Closed Suction Drainage", Orthopedics, Mar. 1990, vol. 13(3), pp. 310-314, in 5 pages.
Berman, A. et al., "Comparison Between Intermittent (Spring-Loaded) and Continuous Closed Suction Drainage of Orthopedic Wounds: a Controlled Clinical Trial", Orthopedics, Mar. 1990, vol. 13(3), in 9 pages.
Besst, J.A., "Wound Healing—Intraoperative Factors", Nursing Clinics of North America, Dec. 1979, vol. 14(4), pp. 701-712, in 7 pages.
Betancourt, S., "A Method of Collecting the Effluent from Complicated Fistula of the Small Intestine," Dept. of Surgery, Allegheny General Hospital, Pittsburgh, p. 375, USA, in 1 page.
Bevan, D. et al., "Diverse and potent activities of HGF/SF in skin wound repair", Journal of Pathology, vol. 203, 2004, pp. 831-838.
Biblehimer, H., "Dealing With a Wound that Drains 1.5 Liters a Day," RN, Aug. 1986, pp. 21-23, USA, in 5 pages.
Bier, A., Hyperemia as a Therapeutic Agent, Ed. Dr. Gustavus M. Blech, A. Robertson & Co., Chicago 1905. (the entire reference has been submitted, but pp. 74-85 may be the most relevant).

Birdsell, D.C., et al., The Theoretically Ideal Donor Site Dressing; Annals of Plastic Surgery, vol. 2, Jun. 1979; Gadgetry, Div. of Plastic Surgery, Foothills, Hospital, Calgary, Canada, 535-537.
Bischoff, M. et al., "Vacuum-Sealing Fixation of Mesh Grafts", Euro. Journ. Plast. Surg., Jul. 2003, vol. 26(4), pp. 189-190, abstract downloaded from internet Apr. 6, 2006, in 1 page.
Blumberg, J. et al., "The Effect of Specific Compression on Soft-Tissue Response to Formalinized PVA (Ivalon) Sponge: a Critical Evaluation", Annals Surg., Mar. 1960, vol. 151(3), pp. 409-418, in 10 pages.
Bonnema, J. et al., "A Prospective Randomized Trial of High Versus Low Vacuum Drainage after Axillary Dissection for Breast Cancer", Amer. Journ. Surg., Feb. 1997, vol. 173, pp. 76-79, in 4 pages.
Boretos, J., "Cellular Polymers for Medical Use: the Vital Role of Porosity and Permeability," Cellular Polymers, 1984, vol. 3, pp. 345-358, in 14 pages.
Borzov, M.V. et al., "Vacuum Therapy of Some Skin Diseases", Vestn. Dermatol. Venerol., No. 8, Aug. 1965, in 12 pages.
Britton, B.J. et al., A Comparison Between Disposable and Non-Disposable Suction Drainage Units: a Report of a Controlled Trial, Br. J. Surg., 1979, vol. 66, pp. 279-280, in 5 pages.
Broader, J.H. et al., "Management of the Pelvic Space after Proctectomy", Br. J. Surg., 1974, vol. 62, pp. 94-97, in 4 pages.
Brock, W.B., et al., "Temporary closure of open abdominal wounds: the Vacuum Pack", Am. Surg. Jan. 1995, vol. 61(1), pp. 30-35, in 6 pages.
Brubacher, L., "To Heal a Draining Wound", RN, Mar. 1982, pp. 30-35, USA, in 7 pages.
Brummelkamp, W.H. et al., "High-vacuum drainage and primary perineal wound closure in abdominoperineal excision of the rectum", the Netherlands Journal of Surgery, 1991, pp. 236-238, Netherlands.
Bruno, P., "The Nature of Wound Healing: Implications for Nursing Practice", Nursing Clinics of North American, Dec. 1979, vol. 14(4), pp. 667-682, in 9 pages.
Bucalo, B. et al., "Inhibition of Cell Proliferation by Chronic Wound Fluid." Wound Repair and Regeneration. Miami, 1993. pp 181-186, in 6 pages.
Bui, T.D. et al., "Negative Pressure Wound Therapy with Off-the-Shelf Components", Amer. Journ. Surg., Jan. 16, 2006, vol. 192, pp. 235-237, in 3 pages.
Burdette-Taylor, S.R., "Use of the Versatile One (V1) for Closed Suction Drainage to Stimulate Closure in Chronic Wounds in Home Care", Case Study Presentation, 2003, in 2 pages.
Bush, G.K., What is a Counter Irritant? Name Three and the Method of Applying Them, Brit. Journ. Nurs., Jun. 1934, p. 142, in 1 page.
Calhoun, P. et al., "Pouching Management of Patients with Open Abdomen, Eviscerations and Bowel Fistulas", Case Studies, Univ. of Miami/Jackson Memorial Medical Center, in 1 page.
Campbell, P.E., "Surgical Wound Case Studies with the versatile 1 Wound Vacuum System for Negative Pressure Wound Therapy", J. WOCN, Mar./Apr. 2006, vol. 33, pp. 176-190.
Campbell, P.E., "Think Negative, Advances for Providers of Post-Acute Care", Sep./Oct. 2005, in 1 page.
Candiani, P. et al., "Repair of a Recurrent Urethrovaginal Fistula with an Island Bulbocavernosus Musculocutaneous Flap", Plastic and Reconstructive Surgery, Dec. 1993, pp. 1393-1394, in 2 pages.
Carroll, P.L., The Principles of Vacuum and its Use in the Hospital Environment, 2nd Ed., 1986, in 30 pages.
Chardak, W. et al., "Experimental Studies on Synthetic Substitutes for Skin and Their Use in the Treatment of Burns," Annals of Surgery, vol. 155, No. 1, 1962, pp. 127-139, in 13 pages.
Chariker, M.E. et al., "Effective Management of Incisional and Cutaneous Fistulae with Closed Suction Wound Drainage," Contemporary Surgery. Jun. 1989, pp. 59-63, vol. 34 USA.
Chart: Influence of Wound Closure on Healing of Perineal Wound after Abdominoperineal Resection or Total Proctocolectomy, excerpt faxed Jan. 23, 2006, 1 page.
Chernavskii, V. A. et al., exerpt from Free Skin Plasty of Wounds and Ulcers using the Vacuum Method, Meditsina Publishers of the Uzbek SSR, Tashkent 1970, pp. 5-37, in 33 pages.
Chin, S. et al., "Closed Wound Suction Drainage," the Journal of Foot Surgery, pp. 76-81, vol. 24 No. 1, 1985.

(56) References Cited

OTHER PUBLICATIONS

Chintamani, V. et al., "Half versus full vacuum suction drainage after modified radical mastectomy for breast cancer—a prospective randomized clinical trial", Research Article, Jan. 27, 2005, pp. 1-5, in 5 pages.
Chua Patel, C.T. et al., "Vacuum-Assisted Closure", AJN, Dec. 2000, vol. 100(12), pp. 45-49, in 6 pages.
Clark, R. et al., The Molecular and Cellular Biology of Wound Repair, Chapter 1, 1988, in 31 pages.
Clean Auxiliary Requests as filed on Mar. 24, 2015, re European Patent No. 2 021 047, in 45 pages.
CMS, HCPCS Public Meeting Summary Report for: Durable Medical Equipment (DME), Jun. 23, 2005, in 39 pages.
Cobb, J.P., "Why Use Drains?", Br. J. Bone Joint Surg., Nov. 1990, vol. 72-B(6), pp. 993-995, in 3 pages.
The Columbia Electronic Encyclopedia: the effect of body temperature on wound healing, printed Jan. 16, 2009, in 3 pages, URL: http://encyclopedia2.thefreedictionary.com/body+temperature.
ComforTrac, ComforTrac Defeats the Saunders Group, Keysville, VA, MEDICA,, Nov. 2006, Brochure, in 2 pages.
Cooper, D.M., "Optimizing Wound Healing", Nursing Clinics of North America, Mar. 1990, vol. 25(1), pp. 163-179, in 10 pages.
Cooper, D.M., "Postsurgical Nursing Intervention as an Adjunct to Wound Healing", Nursing Clinics of North America, Dec. 1979, vol. 14(4), pp. 713-726, in 8 pages.
Cooper, S. et al., "Topical Negative Pressure", Commentary, International Journal of Dermatology, 2000, vol. 39, pp. 892-898, in 3 pages.
Costa, V. et al., "Vacuum-Assisted Wound Closure Therapy (V.A. C.)", Jul. 11, 2005, Centre Universitaire de Sante McGill, McGill University Health Centre, pp. 1-24, in 24 pages.
Costunchenok, B.M., et al., Effect of Vacuum on Surgical Purulent Wounds, *Vestnik Chirurgia* Sep. 18-20, 1986 (in Russian with English translation).
Cotton, P.B. et al., "Early Endoscopy of Oesophagus, Stomach, and Duodenal Bulb in patients with Haematemesis and Melaena", Br. Med. Journ., Jun. 1973, vol. 2, pp. 505-509.
Creative Medical Laboratories, "Instruction Manual", Inc. P.O. Box 6347, Rochester, Minn. 55903. "TUGS" (Transportable Universal Gradient Suction), in 8 pages.
Crisp, W.J. et al., "Granuflex Dressings for Closed Surgical Wounds Combined with Suction Drainage", Annals of the Royal College of Surgeons of England, 1990, vol. 72, p. 76, in 2 pages.
Cucuroos, Y.C., "Vacuum Drainage of Post Operative Wounds", Kiev Army Hospital, Dept. of Hospital Surgery, Kiev medical University, pp. 64-65, in Russian with English translation, in 5 pages.
Curtin, L.L., "Wound Management: Care and Cost—an Overview", Nursing Management, Feb. 1984, vol. 15, pp. 22-25, in 4 pages.
Davis, J.C. et al., Eds., "Chapter 1—Infection and Oxygen", Problem Wounds: the Role of Oxygen, 1988, pp. 1-15.
Davydov et al. "Pathogenic Mechanism of the Effect of Vacuum Therapy on the Course of the Wound Process" Dec. 1986.
Davydov, Y. et al., "Pathogenic Mechanism of the Effect of Vacuum Therapy on the Course of the Wound Process", Khirurgiya, Dec. 1990, No. 6, pp. 42-47, in Russian with English translation, in 15 pages.
Davydov, Y. et al., "Device and Method for Vacuum Therapy of Purulent Lactation Mastites", Khirurgiya, No. 4, Apr. 1988, pp. 131-132 (English translation only), in 2 pages.
Davydov, Y.A., et al. Justifying the Usage of Force Early Secondary Sutures in treatment of Purulent Wounds by the Vacuum Therapy, Vestnik Chirurgia 1990, March Edition, 126-129 (in Russian with English translation).
Davydov, Y.A., et al., Concept of Clinico-Biological Management of Wound Process in Treatment of Purulent Wounds with the Help of Vacuum Therapy, Vestnik Chirurgia 1991, February Edition, 132-135 (in Russian with English translation).

Davydov, Y.A. et al., "The Bacteriological & Cytological Assessment of Vacuum Therapy of Purulent Wounds", Vestnik Chirurgia Oct. 1988 Edition 48-52 (in Russian with English translation). 1987.
Davydov, Y.A. et al., "Vacuum Therapy in the Treatment of Purulent Lactational Mastitis", Vestnik Chirurgia, Grexova Sep. 1986 Edition, 66-70 (in Russian with English translation).
Davydov, Yu A., et al., "Concepts for Clinical Biological Management of the Wound Process in the Treatment of Purulent Wounds Using Vacuum Therapy", the Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", the Kremlin Papers: Perspectives in Wound Care, Russian Journal: Vestnik Khirurgii, BlueSky Publishing, La Costa, California (2004), 11-14.
Davydov, Yu A., et al., "Vacuum Therapy in the Treatment of Purulent Lactation Mastitis", the Kremlin Papers: Perspectives in Wound Care, Russian Journal: Vestnik Khirurgii, BlueSky Publishing, La Costa, California (2004), 5-7.
De Lange, M.Y. et al., "Vacuum-Assisted Closure: Indications and Clinical Experience", Eur J Plast Surg, 2000, vol. 2, Feb. 9, 2000, pp. 178-182, in 5 pages.
Deknatel, Div. of Howmedica, Inc. Queens Village, NY 11429. "Pleur-evac.".
Dewan, P.A., "An Alternative Approach to Skin Graft Donor Site Dressing", Aust. N.Z. J. Surg. 1986, vol. 56, pp. 509-510, in 4 pages.
Dillon, R., "Treatment of Resistant Venous Stasis Ulcers and Dermatitis with the End-Diastolic Pneumatic Compression Boot", Angiology—the Journal of Vascular Diseases, pp. 47-55, Jan. 1986, in 9 pages.
Dilmaghani, A. et al., "A Method for Closed Irrigation and Suction Therapy in Deep Wound Infections," Journal of Bone and Joint Surgery, 1969, vol. 51-A, No. 2, pp. 323-342, in 20 pages.
Doillon, C.J. et al., "Collagen-Based Wound Dressings: Control of the Pore Structure and Morphology", Journal of Biomedical Materials Research, Sep. 13, 2004, vol. 20(8), pp. 1219-1228, abstract downloaded from Internet Apr. 28, 2006, in 2 pages. URL: http://www3.interscience.wiley.com.
Domkowski, P.W. et al., "Evaluation of Vacuum-Assisted Closure in the Treatment of Poststernotomy Mediastinitis", Journ. of Thorac. and Cardiovascular Surg., Aug. 2003, vol. 126(2), pp. 386-390, in 5 pages.
Doss, M. et al., "Vacuum-Assisted Suction Drainage Versus Conventional Treatment in the Management of Poststernotomy Osteomyelitis", Euro. Journ. Cardio-Thoracic. Surg., vol. 22, 2002, pp. 934-938, in 4 pages.
Draper, J., "Make the Dressing Fit the Wound", Nursing Times, Oct. 9, 1985, pp. 32-35, in 4 pages.
Dunbar, A. et al., "Silicone Net Dressing as an Adjunct with Negative Pressure Wound Therapy", Ostomy/Wound Management, Nov. 2005, vol. 51(1A Suppl.), pp. 21-22, in 2 pages.
Dunbar, J.M., "State What You Have Learned Recently on the Up-to-Date Care of Wounds", Brit. Journ. Nurs., Dec. 1941, p. 200, in 1 page.
Dunlop, M.G et al. "Vacuum Drainage of Groin Wounds after Vascular Surgery: a Controlled Trial", Br. J. Surg., May 1990, vol. 77, pp. 562-563, in 2 pages.
Eaglstein, W.H. et al., "Wound Dressings: Current and Future", Clin, and Exper. Approaches to Dermal and Epidermal Repair: Normal and Chronic Wounds, 1991, pp. 257-265, in 5 pages.
ECRI, Target Report, "Negative Pressure Wound Therapy for Chronic Wounds", Jan. 24, 2006, pp. 1-7, downloaded from internet, in 7 pages. URL: http://www.target.ecri.org/summary/detail.aspx7dox_id=1155.
Eisenbud, D.E., Modern Wound Management, Anadem Publishing, Chap. 16, 109-116, 2000.
Ellingwood, F. "Ellingwood's Therapeutist", Jun. 14, 1908, vol. 2(6), pp. 32-33, in 4 pages.
Elwood, E.T. et al., "Negative-Pressure Dressings in the Treatment of Hidradenitis Suppurative", Annals of Plastic Surgery, Jan. 2001, vol. 46(1), pp. 49-51, in 3 pages.
Emerson, J.H. Emerson Co., 22 Cottage Park Ave., Cambridge, MA 02140, "Emerson Transport Suction Unit."

(56) References Cited

OTHER PUBLICATIONS

Emerson, Series 55, J.H. Emerson Co., 22 Cottage Park Ave., Cambridge, MA 02140. "Emerson Post-Operative Suction Pumps," 1 page.
Engdahl, O. et al., "Quantification of Aspirated Air vol. reduces Treatment Time in Pneumothorax", Eur. Respir, J., 1990, vol. 3, pp. 649-652, in 6 pages.
Engdahl, O. et al., "Treatment of Pneumothorax: Application of a Technique which Quantifies Air Flow Through the Chest Drain", Adv. in Therapy, May/Jun. 1988, vol. 5(3), pp. 47-54.
English Translation of Invalidity Suit by KCI Medizinprodukte GmbH versus Kalypto Medical, Inc., concerning declaration of invalidity of the German part of the European Patent No. 2 021 046 (German application No. 60 2007 021 330.4) dated Mar. 11, 2015 in 38 pages.
English translation of Opposition of European patent EP 2021047 B1, dated Jul. 16, 2014, on behalf of Sorbion GmbH & Co., in 32 pages.
Erichsen, J.E., The Science and Art of Surgery, London: Longmans, Green, and Co., 1895, vol. 1, pp. 258-259, and 289, in 4 pages.
Examination Report for International Application No. PCT/GB2004/004564, dated Jun. 11, 2008 in 3 pages.
Fabian, T.S., The Evaluation of Subatmospheric Pressure and Hyperbaric Oxygen in Ischemic Full-Thickness Wound Healing, Ischemic Full-Thickness Wound Healing, Dec. 2000, vol. 66(12), pp. 1136-1143, in 8 pages.
Falanga, V., "Growth Factors and Chronic Wounds: the Need to Understand the Microenvironment." Journal of Dermatology, vol. 19, pp. 667-672, 1992, in 6 pages.
Fay, M.F., "Drainage Systems: Their Role in Wound Healing", AORN Journal, Sep. 1987, vol. 46(3), pp. 442-455.
Fellin, R., "Managing Decubitus Ulcers", Nursing Management, Feb. 1984, pp. 29-30, in 2 pages.
Fingerhut, A., et al., "Passive vs. Closed Suction drainage after Perineal Wound Closure Following Abdominoperineal Rectal Excision for Carcinoma", Dis Colon Rectum, Sep. 1995, pp. 926-932, in 7 pages.
Finley, J., "Practical Wound Management: a Manual of Dressing," London, pp. 45, 127, 143, 149, 207, 1981, in 7 pages.
Firlit, C.F. et al., "Surgical Wound Drainage: a Simple Device for Collection", Journ. of Urology, Aug. 1972, vol. 108, p. 327, in 1 page.
Fisher, J. et al., "A Technique for Skin Grafting Around Abdominal Wall Fistulas", Annals of Plastic Surgery, vol. 11:6, Dec. 1983, pp. 563-564, in 2 pages.
Flanagan, S. et al., "Optional Sump: Novel Use of Triple Lumen Closed Drainage System", Anz. J. Surg., Nov. 2002, vol. 72(11), pp. 806-807, abstract downloaded from internet Nov. 30, 2003, in 1 page.
Fleck, C.A., "When Negative is Positive: a Review of Negative Pressure Wound therapy", Wound Care, Mar./Apr. 2004, pp. 20-25, in 6 pages.
Fleischmann, "Vacuum sealing: indication, technique, and results," European Journal of Orthopaedic Surgery & Traumatology, vol. 5(1), 1995, pp. 37-40.
Fleischmann, W. Acta Orthopaedical Belgica, "Treatment of Bone and Soft Tissue Defects in Infected Nonunion," vol. 58, Suppl. I-1992, pp. 227-235, in 9 pages.
Fleischmann, W. Unfall Chirurg, Springer-Variag, "Vakuumversiegelung zur Behandlung des Weichteilschadens bei offenen Frakturen," (English abstract, no English translation), 1993, pp. 488-492.
Fleischmann, W. Wund Forum Spezial, "Vakuumversiegelung zur Behandlung von Problemwunden" (with English translation: Vacuum Sealing for Treatment of Problematical Wounds), IHW '94, 6 pages.
Flynn, M.E. et al., "Wound Healing Mechanisms", Amer. Journ. of Nursing, Oct. 1982, 1544-1556, in 14 pages.
Fox, J.W. et al., "The Use of Drains in Subcutaneous Surgical Procedures", Amer. Journ. of Surg, Nov. 1976, vol. 132, pp. 673-674, in 2 pages.
Froberg, Birgitta et al., Vacusac Therapy—a Supplement to the Treatment of Varicose Ulcers? (Stockholm) 1990, in 37 pages.
Garcia-Rinaldi, R. et al., "Improving the Efficiency of Wound Drainage Catheters", Amer. Journ. of Surg., Sep. 1975, vol. 130, pp. 372-373, in 2 pages.
Garner, G. et al., "Vacuum-assisted wound closure provides early fascial reapproximation in trauma patients with open abdomens," Am. J. of Surgery, vol. 182, 2001, pp. 630-638, in 9 pages.
Geiger Jones, E. et al., "Management of an Iliostomy and Mucous Fistula Located in a Dehisced Wound in a Patient with Morbid Obesity", J. WOCN, Nov. 2003, vol. 30(6), pp. 351-356, in 7 pages.
Gill, P., "What is a Counter-Irritant? Name Three and the Method of Applying Them", Brit. Journ. Nurs., Jun. 1934, p. 142, in 1 page.
Goddard, L., "Inflammation: Its Cause and Treatment", Brit. Journ. Nurs., Jan. 1944, p. 2, in 1 page.
Gogia, P., "The Biology of Wound Healing", Ostomy/Wound Management. Nov.-Dec. 1992, pp. 12-20.
Gogolewski, S. et al., "Polyurethane Vascular Prosthesis in Pigs", Colloid & Polymer Science, Sep. 1987, vol. 265(9), pp. 774-778, abstract downloaded from internet Mar. 20, 2006, in 2 pages.
"Gomco Suction Equipment & Accessories Guide", Catalog, Apr. 2006, in 20 pages.
"GOMCO Gastro-Intestinal Thermotic Drainage Pump 270 NR", eBay, downloaded from internet Apr. 7, 2006, in 6 pages. URL: http://cgi.ebay.com.
Gouttefangeas, C. et al., "Functional T Lymphocytes Infiltrate Implanted Polyvinyl Alcohol Foams During Surgical Wound Closure Therapy", Clin. Exp. Immunol., 2001, vol. 124, pp. 398-405, in 8 pages.
Goverman, J. et al., "The 'Fistula VAC,' a Technique for Management of Enterocutaneous Fistulae Arising within the Open Abdomen: Report of 5 Cases", Journ. of Trauma Injury, Infection, and Critical Care, Feb. 2006, vol. 60(2), pp. 428-431, in 4 pages.
Grabowski, S., "Leczenie ran z zastosowaniem posicśnienia (wg Redona I Josta)", II Klinik Xhieuefxnej AM w Warszawie; klerownik: Prof. Dr. Z. Lapinski, No. 1, pp. 19-21 (in Polish), in 3 pages.
Greene, M. A. et al., "Laparotomy Wound Closure with Absorbable Polyglycolic Acid Mesh", Surgery, Gynecology and Obstetrics, Mar. 1993, vol. 176, pp. 213-218.
Grishdevich, V. et al., "Postburn Facial Resurfacing with a Split Ascending Neck Flap", Plastic and Reconstructive Surgery, Dec. 1993, pp. 1384-1391, in 8 pages.
Grobmyer, S.R. et al., "High-Pressure Gradients Generated by Closed-Suction Surgical Drainage Systems", Surg. Infect. (Larchmt), Autumn 2002, vol. 3(3), pp. 245-249, abstract downloaded Nov. 30, 2003, in 1 page.
Grover, R. et al., "Recent Advances: Plastic Surgery", Clinical Review, BMJ, Aug. 8, 1998, vol. 317, pp. 397-400, in 5 pages.
Gupta, S., Ed., "Guidelines for Managing Pressure Ulcers with Negative Pressure Wound Therapy", Advances in Skin & Wound Care Suppl., Nov./Dec. 2004, vol. 17(2), pp. 1-16, in 16 pages.
Gupta, S., "Guidelines for Managing: Pressure Ulcers with Negative Pressure Wound Therapy", downloaded from internet Feb. 3, 2006, in 19 pages. URL: http://proquest.umi.com.
Gwan-Nulla, D.N. et al., "Toxic Shock Syndrome Associated with the Use of the Vacuum-Assisted Closure Device", Ann. Plast. Surg., Nov. 2001, vol. 47(5), pp. 552-554, in 3 pages.
Halasev, S., "Growing Public", MX Business Strategies for Medical Technology Executives, Mar./Apr. 2005, in 5 pages.
Hallstrom, B.R. et al., "Postoperative Course after Total Hip Arthroplasty: Wound Drainage versus No Drainage", Orthopaedic Review, Jul. 1992, pp. 847-851, in 5 pages.
"Hanbok för Hälso-Och Sjukvårdsarbete Lokal Anvisning för Landstinget Sörmland", Jan. 2001, in Swedish, downloaded from internet Aug. 14, 2001, in 7 pages. URL: http://www.landstinget.sormland.se.
Hargens, A. et al., "Lower Body Negative Pressure to Provide Load Bearing in Space", Aviation, Space and Environmental Medicine, Oct. 1991, pp. 934-937, in 4 pages.
Hargens, A. et al., "Control of Circulatory Functions in Altered Gravitational Fields", Space Physiology Laboratory Life Science Division, NASA Ames Research Center, Physiologist, Feb. 1992, vol. 35(1 Suppl):S80-3, in 4 pages.

(56) References Cited

OTHER PUBLICATIONS

Harkiss, K., "Cheaper in the Long Run", Community Outlook, Aug. 1985, pp. 19-22.
Harle, A., "Schwachstellen herkommlicher Drainagen,"Z Orthop, vol. 127, 1989, pp. 513-517.
Harris, D., "A new technique of skin grafting using Stei-Greffe and a self-adhering foam pad", Brit. J. of Plastic Surg., vol. 34(2), Apr. 1981, pp. 181-185, in 6 pages.
Hartz, R.S. et al., "Healing of the Perineal Wound", Arch. Surg., Apr. 1980, vol. 115, pp. 471-474, in 4 pages.
Harvard Pilgrim Health Care, Technology Assessment Policy, "TA 6.29 Negative Pressure Wound Therapy for Wound Healing", Dec. 2004, pp. 1-6, in 6 pages.
Hay, J. et al., "Management of the Pelvic Space With or Without Omentoplasty after Abdominoperineal Resection for Carcinoma of the Rectum: a Prospective Multicenter Study", Eur. J. Surg, 1997, abstract only, in 1 page.
Hays, K., "Online Casket Seller Provides an Alternative", San Antonio Express-News, Sunday, Feb. 13, 2005, Sec. 1, in 3 pages.
CMS, HCPCS Public Meeting Agenda for Jun. 23, 2005, Durable Medical Equipment (DME), in 28 pages.
"Applications for Modifications to HCPCS Level II Code Set in the 2005-2006 Coding Cycle", HCPCS, in 60 pages.
Health Technology Literature Review, "Vacuum Assisted Closure Therapy for Wound Care", Dec. 2004, pp. 3-57, in 57 pages.
Higgins, S., "The Effectiveness of Vacuum Assisted Closure (VAC) in Wound Healing", Centre for Clinical Effectiveness, Monash Medical Centre, Clayton VIC Australia, Dec. 2003, pp. 1-16.
Hilsabeck, J.R., "The Presacral Space as a Collector of Fluid Accumulations Following Rectal Anastomosis: Tolerance of Rectal Anastomosis to Closed Suction Pelvic Drainage", Amer. Soc. of Colon and Rectal Surgeons, vol. 25(7), Oct. 1982, in 5 pages.
Hilton, P., "Surgical Wound Drainage: a Survey of Practices among Gynaecologists in the British Isles", Br. Journ. of Obstetrics and Gynaecology, Oct. 1988, vol. 95, pp. 1063-1069, in 7 pages.
Hollis, H.W. et al., "A Practical Approach to Wound care in patients with Complex Enterocutaneous Fistulas", Surg., Gyn. & Obs., Aug. 1985, vol. 161, pp. 179-181, in 3 pages.
Hugh, T.B., "Abdominal Wound Drainage", Med. Journ. of Australia, May 4, 1987, vol. 146, p. 505 (Correspondence), in 1 page.
Hulten, L. et al., "Primary Closure of Perineal Wound after Proctocolectomy or Rectal Excision", Acta Chir. Scand., 1971, vol. 137, pp. 467-469, in 3 pages.
Hunt, T.K. et al., Eds., Fundamentals of Wound Management, Appleton-Century-Crofts/New York, 416-447, 1979, in 19 pages.
"Chapter VIII—Hyperemia by Suction Apparatus", pp. 74-85, in 6 pages.
Ilizarov, G.A., "The Tension-Stress Effect on the Genesis and Growth of Tissues: Part II. The Influence of the Rate and Frequency of Distribution", Clinical Orthopaedics and Related Research, Feb. 1989, vol. 239, pp. 263-283, in 21 pages.
Info V.A.C. User Manual—KCI—Dec. 2006, in 76 pages.
INSTECH Model P720 Peristaltic Pump Operation Manual, Dec. 1997, pp. 1-11, in 7 pages.
Izmailov, S.G. et al., "Device for Treatment of wounds and Abdominal Cavity", Contents, Surgery No. 8, 1997, downloaded from internet, in 1 page. URL: http://www.mediasphera.ru/surgery/97/8/e8-97ref.htm.
Izmailov, S.G., "The Treatment of Eventrations with a Special Apparatus", Abstracts, Surgery No. 1, 1997, downloaded from internet, in 1 page. URL: http://www.mediasphera.ru/surgery/97/1/e1-97ref.htm.
Jahns, B. et al., Poster "Problemwundversorgung mit einem neuen anschmiegsamen Silikonschaumverband mit Anwendung der Vakuumtechnik," 2nd Congress of German Wound Treatment Society 1998.
Jeter, K., "Closed Suction Wound Drainage System", J. WOCN, Mar./Apr. 2004, p. 51 (Correspondence), in 1 page.
Jeter, K. et al., "Managing Draining Wounds and Fistulae: New and Established Methods", Chronic Wound Care, Chapter 27, pp. 240-246, 1990, in 7 pages.
Jeter. K., Poster Presentation—Meeting for Int'l Association for Enterostomal Therapy in Washington, DC, Jun. 6-10, 1989, in 10 pages.
Johnson, F.E., "An Improved Technique for Skin Graft Placement using a Suction Drain", Surgery, Gynecology & Obstetrics, Dec. 1984, vol. 159(6), pp. 584-585, in 3 pages.
Kalypto Medical, NPD 1000 Negative Pressure Wound Care System, Clinician & Patient Instructions for Use (publication date unknown, believed to be Feb. 2010), in 36 pages.
Kalypto Medical, NPD 1000 Product Brochure (publication date unknown, believed to be Nov. 2010), in 4 pages.
Kazan Medical Institute Doctors, "A Gadget to Bring the Wound Edges Close", Aug. 20, 1985, pp. 78-79 (in Russian with English translation), in 4 pages.
"KCI Introduces New Vacuum Assisted Closure Product; V.A.C. Freedom Device Continues Company's Leadership in Advanced Wound Healing Systems," PR Newswire, Oct. 2002, in 3 pages.
KCI Licensing, "V.A.C. Abdominal Dressing System Advanced Management of the Open Abdomen," 2004, in 6 pages.
KCI USA, Inc., Vacuum Therapy Unit, U.S. Food and Drug Administration, database updated Apr. 1, 2005, download from internet, in 2 pages.
KCI, Inc., "Annual Report 2004—Changing the Standard of Healing", pp. 1-113, in 128 pages.
KCI, Inc., "If It's Not V.A.C. Therapy, It's Not Negative Pressure Wound Therapy", KCI brochure, Jan. 2005, pp. 1-5, in 5 pages.
KCI, Inc., "Introducing the V.A.C. GranuFoam Silver Dressing", Flyer, in 2 pages.
KCI, Inc., "V.A.C. Freedom® System Receives Joint Airworthiness Certification", Yahoo Finance, Press release downloaded from internet, published Dec. 21, 2006, in 5 pages. URL: http://biz.yahoo.com/bw/061221/20061221005599.html?v=1.
KCI, Inc., "The V.A.C. System", 2000-2001, Brochure, in 2 pages.
KCI, Inc., "V.A.C. Therapy (Negative Pressure Wound Therapy)—Medicare Part-B Documentation Guidelines", May 2001, Lit. No. 26-B-104, pp. 1-19, in 19 pages.
KCI, Inc., Vacuum Assisted Closure (V.A.C) from Wound Healing, Evidence Note 5, NHS Quality Improvement Scotland, Nov. 2003, 1 page.
Keen, W.W., Ed., "Surgery—Its Principles and Practice", 1919, W. B. Saunders Company, p. 56, excerpt, in 2 pages.
Keith, C.F., "Wound Management Following Head and Neck Surgery", Nursing Clinics of North America, Dec. 1979, vol. 14(4), pp. 761-779, in 10 pages.
"Kendall ULTEC Hydrocolloid Dressing (4"×4")", product ordering page, web page downloaded Jul. 13, 2014, in 1 page.
Kennard, H.W., "Bier's Hyperaemia", British Journal of Nursing, Mar. 20, 1909, p. 223, in 1 page.
Khan, T. et al., "Influence of Chitosan Molecular Weight on its Physical Properties", EIMJM, 2003, vol. 2(1), pp. 1-8.
Khil'Kin, A.M. et al., "Use of a Collagen Hemostatic Sponge for the Experimental Closing of the Surface of a Liver Wound" (article in Russian), EKSP Khir Anesteziol, Nov.-Dec. 1974, vol. 6, pp. 38-41, citation cownloaded from the internet Apr. 24, 2006, in 1 page. URL:http://www.ncbi.nlm.nih.gov.
The Kremlin Papers, "A Collection of Published Studies Complementing the Research and Innovation of Wound Care", the Kremlin Papers—Perspectives in Wound Care, Russian Medical Journal, Vestnik Khirurgii, Blue Sky Publishing (2004), pp. 2-17, in 17 pages.
Kiemele, L. J. et al., "Catheter-Based Negative Pressure Wound Therapy: a New Paradigm of Care", Nursing Home Wound Care Consultative Service, Mayo Clinic, Rochester, MN, in 2 pages.
Kim, S.H. et al., "Wangensteen Suction Drainage, Apparatus in Neurosurgical Practice", Dept. of Neurosurgery, Yonsei University of College of Medicine, Seoul, Korea, 1975, pp. 159-160, abstract only (in Korean and English), in 2 pages.
Klemp, P. et al., "Subcutaneous Blood Flow in Early Male Pattern Baldness", Journal of Investigative Dermatology, 1989, pp. 725-726, in 2 pages.

(56) References Cited

OTHER PUBLICATIONS

Kloth, L.C. et al., "Chapter 10—Adjunctive Interventions for Wound Healing", Wound Healing Alternatives in Management, 3rd Ed., 2002, pp. 339-352, in 15 pages.

Knight, M., "A Second Skin for Patients with Large Draining Wounds", Nursing, Jan. 1976, p. 37, USA, in 1 page.

Kockrow, E., "Chapter 13—Surgical Wound Care", Surgical Wound Care, 2006, pp. 1-32, in 33 pages.

Kohlman, P. et al., "Pouching Procedure to Collect Drainage From Around a Biliary Drainage Catheter," Ostomy/Wound Management, Nov./Dec. 1991, vol. 37, pp. 47-50.

Kordasiewicz, L.M., "Abdominal Wound with a Fistula and Large Amount of Drainage Status after Incarcerate Hernia Repair", J. WOCN, May/Jun. 2004, vol. 31(3), pp. 150-153, in 4 pages.

Kostiuchenok, B. M., et al., "The Vacuum Effect in the Surgical Treatment of Purulent Wounds", the Kremlin Papers: Perspectives in Wound Care, Russian Journal: Vestnik Khirurgii, BlueSky Publishing, La Costa, California (2004), 3-4.

Landes, R.R. et al., "An Improved Suction Device for Draining Wounds," Arch. Surg., May 1972, vol. 104, p. 707, in 1 page.

Landis, E.M. et al., "The Effects of Alternate Suction and Pressure on Blood Flow to the Lower Extremities", Alternate Suction and Pressure, J Clin Invest. Sep. 1933, vol. 12(5), pp. 925-961.

Larichev, A.B., "Vacuum Therapy in Treatment of Purulent Wounds and Mechanism of its Influence on Wound Process", 1988, article in Russian, labeled [21], in 13 pages.

Larichev, A.B., "Vacuum Therapy of Wounds and Wound Infection", 1st. Ed., BlueSky Publishing, 2005, in 237 pages.

Lee, J.H. et al., "Application of Medifoam B® & Negative Pressure Therapy for the Auxiliary Treatment of Pressure Sore", Sep. 31, 2004, Department of Plastic and Reconstructive Surgery, College of Medicine, Eulji Univ., Daejeon, Korea, abstract only, in 1 page.

Lehrman, S., "The Not-So-Bald-Truth", Science, Sep. 1992, p. 42, in 1 page.

Letsou, G. et al., "Stimulation of Adenylate Cyclase Activity in Cultured Endothelial Cells Subjected to Cyclic Stretch", Journal of Cardiovascular Surgery 3, Toronto, Sep. 1989, pp. 634-639, in 6 pages.

Levine, J.M., "Implementing the New CMS Guidelines for Wound Care", Nursing Homes, Apr. 21, 2006, downloaded from internet, in 12 pages. URL: http://www.nursinghomesmagazine.com/Past_Issues.htm?ID=4408.

Linden, W. et al. "Randomized Trial of Drainage After Cholecystectomy", Modern Operative Techniques, vol. 141, Feb. 1981, pp. 289-294, in 6 pages.

Lockwood, C.B., "Aseptic Surgery, Drainage", British Journal of Nursing, Mar. 26, 1904, p. 245, in 1 page.

Luchette, F.A., "When Should the General Surgeon Leave the Abdomen Open?", Division of Trauma, Surgical Critical Care and Burns, Loyola University Medical Center, Maywood, Illinois., 37 pages (date N/A).

Lumley, J.S.P. et al., "The Physical and Bacteriological Properties of Disposable and Non-Disposable Suction Drainage Units in the Laboratory", British Journal of Surgery, 1974, vol. 61, pp. 832-837, in 6 pages.

Lundvall, J. et al., "Transmission of Externally Applied Negative Pressure to the Underlying Tissue: a Study on the Upper Arm of Man", Acta Physiol. Scand. 1989, vol. 136, pp. 403-409, in 7 pages.

Maddin, W. et al., "The Biological Effects of a Pulsed Electrostatic Field with Specific References to Hair: Electrotrichogenesis", International Journal of Dermatology, vol. 29, Jul./Aug. 1990, pp. 446-450, in 5 pages.

Magee, C. et al., "Potentiation of Wound Infection by Surgical Drains", Amer. Journ. of Surg., May 1976, vol. 131, pp. 547-549, in 3 pages.

Maitland, I. et al., "Suction Drainage", Brit. J. Surg, Mar. 1970, vol. 57(3), pp. 195-197, in 5 pages.

Malli, S., "Keep a Close Eye on Vacuum-Assisted Wound Closure", Device Safety, DHHS, CDRH, May 2005, in 1 page.

Mayo, C.W., "The One-Stage Combined Abdominoperineal Resection for Carcinoma of the Rectum, RectoSigmoid and Sigmoid", Surgical Clinics of North America, Aug. 1939, Mayo Clinic No. 1011-1012, in 9 pages.

McFarlane, R. M., "The Use of Continuous Suction Under Skin Flaps", F.R.C.S.(c), vol. 1, 1958, pp. 77-86, in 10 pages.

McGuire, S., "Drainage after Abdominal Section", British Journal of Nursing, Dec. 15, 1903, pp. 447-449, in 3 pages.

McLaughlan, J., "Sterile Microenvironment for Postoperative Wound Care", The Lancet, pp. 503-504, Sep. 2, 1978, in 2 pages.

Medela Product Information (with English Summary): "Pleupump MK II is the new micro-data controlled thoracic drainage", in 12 pages.

Medela, Inc., Medela Obstetrical Vacuum Delivery System, 510(k) Summary K041579, Apr. 21, 2005, Correspondence, in 6 pages.

Medela, Inc., "Medela to Increase Presence in Wound Care Market", Press Release, Chicago, IL, Aug. 29, 2006, in 2 pages.

Medela, Inc., Pleupump MK II, Aug. 14, 2001, Brochure (in German). 12 pages.

Medela, Manualectric Breastpump, Catalog, in 4 pages.

Medtronic, Octopus System, Catalog, in 3 pages.

Advantec MFS, Inc., "Membrane Filters" (catalog), accessed Jan. 29, 2016 (publication date unknown, but believed to be copyright 2001-2011), in 17 pages. URL: http://www.advantecmfs.com/catalog/filt/membrane.pdf#page=11.

Mendez-Eastman, S., Guidelines for Using Negative Pressure Wound Therapy, Advances in Skin & Wound Care, 14(6), Nov./Dec. 2001, 314-325.

Mendez-Eastman, S., "When Wounds Won't Heal", RN, Jan. 1998, pp. 2-7, in 7 pages.

Meyer et al., Bier's Hyperemic Treatment, Fig. 69-70, 1908, p. 557, in 1 page.

Meyer and Schmieden, Bier's Hyperemic Treatment, Published 1908 W. B. Saunders Company, 44-65.

Meyer, W. et al., "Bier's Hyperemic Treatment in Surgery, Medicine, and the Specialties: a Manual of its Practical Application", 1908, in 222 pages (uploaded in 3 parts).

Meyer, W. & Schmieden, V., Bier's Hyperemic Treatment, W B. Saunders Company 1908, (the entire reference has been submitted, but pp. 44-65 may be the most relevant).

Meyer, Weight-Loaded Syringes as a Simple and Cheap Alternative to Pumps for Vacuum-Enhanced Wound Healing, Plastic and Reconstructive Surg., Jun. 2005, 2174-2176 (Correspondence).

Microtek Heritage, Inc. P.O. Box 2487, Columbus, MS 39704, "Wound-Evac ET," 4 pages.

Miles, W., "Technique of the Radical Operation for Cancer of the Rectum", The British Journal of Surgery, 2006, pp. 292-304, United Kingdom 1914-1915.

Miles, W.E., A Method of Performing Abdominoperineal Excision for Carcinoma of the Rectum and of the Terminal Portion of the Pelvic Colon, The Lancet, Dec. 19, 1908, 1812-1813.

Miller, M.S. and C. McDaniel, Treating a Pilonidal Cystectomy Abscess Wound with the BlueSky Medical Versatile 1™ Negative Pressure Wound Therapy, the Wound Healing Center, Terre Haute, Indiana, Case Study 2004-2006, 1 page.

Miller, M.S., APWCA Case #3: Using Negative Pressure for Wound Therapy, Podiatry Management, Jun./Jul. 2005, 121-126.

Miller, M.S., Commentary: New Microvascular Blood Flow Research Challenges Practice Protocols in Negative Pressure Wound Therapy, Wounds 2005, 17(10) 290-294.

Miller, M.S., et al., Negative Pressure Wound Therapy Options Promote Patient Care, Biomech, Sep. 2005, Downloaded from internet http://www.biomech.com , Jan. 19, 2007.

Miller, M.S., et al., Negative Pressure Wound Therapy: an Option for Hard-to-Heal Wounds, focuson Wound care, Jan. 2006, 57-61.

Miller, M.S., et al., Treating a Postoperative, Ischemic Foot Wound Using Bovine Dermal-Derived Extra-Cellular Matrix PRIMATRIX™ with the BlueSky Medical Versatile 1™ Negative Pressure Wound Therapy System, the Wound Healing Center, Terre Haute, Indiana, Case Study 2005.

Miller, M.S., et al., Treating an Wagner Grade 3 Diabetic Foot Ulcer using BlueSky Medical Versatile 1™ Negative Pressure Wound

(56) References Cited

OTHER PUBLICATIONS

Therapy System and the Miller DermiVex™ Drain, the Wound Healing Center, Terre Haute, Indiana, Case Study 2005.
Miller, M.S., Negative Pressure Wound Therapy: "A Rose by Any Other Name," Ostomy/Wound Management, Mar. 2005, 51(3), 44-49.
Milsom, I. and A. Gustafsson, an Evaluation of a Post-Operative Vacuum Drainage System, Curr. Med. Res. Opin. (1979), 6, 160-164.
Mitchell, R. et al., "Role of Stem Cells in Tissue Homeostasis", Pocket Companion to Robbins and Cotran Pathologic Basis of Disease, Seventh Ed., 2006, in 1 page.
Mokhtari, A., et al., Sternal Stability at Different negative Pressure during Vacuum-Assisted Closure Therapy, Soc. of Thoracic Surgeons, 2006, 82, 1063-1067.
Moloney, G. E., "Apposition and Drainage of Large Skin Flaps by Suction", ANZ Journal of Surgery vol. 26, Issue 3, Feb. 1957, pp. 173-179.
Morykwas, M. J., et al., "Vacuum-Assisted Closure: a New Method for Wound Control and Treatment: Animal Studies and Basic Foundation," Annals of Plastic Surgery 38 (1997) 553-562, Dec. 10, 1996.
Morykwas, M. J., et al.: "Nonsurgical Modalities to Enhance Healing and Care of Soft Tissue Wounds", Journal of the Southern Orthopaedic Association, vol. 6, No. 4 Winter 1997 in 11 pages.
Morykwas, M.J., et al., Effects of Varying Levels of Subatmospheric Pressure on the Rate of Granulation Tissue Formation in Experimental Wounds in Swine, Abs., Ann. Plast. Surg. 2001, 47:547.
Morykwas, Michael J., et al., "Vacuum-Assisted Closure: a New Method for Wound Control and Treatment: Animal Studies and Basic Foundation", Ann Plast Surg 1997;38:553-562 (Dec. 10, 1996).
Moserova, J. and E. Houskova, the Healing and Treatment of Skin Defects, 1989, 116-143.
Moss, W., What is Cellulitis? Describe Some Forms of Treatment You Would Expect to be Used for Cellulitis of the Arm, Brit. Journ. Nurs., Nov. 1935, 282.
Mulder, G.D., Ed., et al., Clinicians' Pocket Guide to Chronic Wound Repair, Wound Healing Publications, Spartanburg, SC, 1991, 54-55.
Mullner, T., et al., The Use of Negative Pressure to Promote the Healing of Tissue Defects: a Clinical Trial Using the Vacuum Sealing Technique, Br. J. Plast. Surg., Apr. 1997, 51(1), 79, Abs.
Musashaikhov, K.T., et al., The Course of Wound Healing under the Influence of Polyphepan in patients with Diabetes Mellitus, Abstracts, Surg. No. 5, 1997, Downloaded from internet, http://www.mediasphera.ru/surgery/97/5/e5-97ref.htm, 1 page.
Nakayama et al., Ann. Plast. Surg., 26: 499-502 (1991), "A New Dressing Method for Free Skin Grafting in Hands."
Nakayama, Y. et al., "A New Method for the Dressing of Free Skin Grafts", Plastic and Reconstructive Surgery, Dec. 1990, pp. 1216-1219.
Nasser, A.N., The Use of the Mini-Flap Wound Suction Drain in maxillofacial Surgery, Annals of the Royal College of Surgeons of England, 1986, 68, 151-153.
Navsaria, P.H., et al., Temporary Closure of Open Abdominal Wounds by the Modified Sandwich-Vacuum Pack Technique, Br. Journ. Surg., 2003, 90, 718-722.
Nghiem, D.D., A Technique of Catheter insertion for Uncomplicated Peritoneal Dialysis, Surgery, Gynecology & Obstetrics, Dec. 1983, 157, 575-576.
Nicholas, J.M., Options for Management of the Open Abdomen, Presentation from Emory University School of Medicine, 66 pgs. Invited Speaker American College of Surgeons 32nd Annual Spring Meeting, General Session 12—Presentation and Panel Discussion on the Open Abdomen in General Surgery—How Do You Close the Abdomen When You Can't—Boston Marriott Copley Place Hotel, Boston, MA Apr. 26, 2004.
Nightingale, K., Making Sense of wound Drainage, Nursing time Jul. 5, 1989, 85(27), 40-42.
Noblett, E.A., What is an Empyema? What Operations are Undertaken for its Relief, and What Have You to Say About the After-Nursing?, Brit. Journ. Nurs., Apr. 29, 1916, 375.
Norton, S.E., et al., Vacuum-Assisted Closure (V.A.C Therapy) and the Risk of Fluid Loss in Acute Trauma, Ann. of Plast. Surg., Feb. 2006, 56(2), 194-195.
Nursing75, "Wound Suction: Better Drainage with Fewer Problems", Nursing, vol. 5, No. 10, Oct. 1975, pp. 52-55.
O'Byrne, C., Clinical Detection and Management of Postoperative Wound Sepsis, Nursing Clinics of North American, Dec. 1979, 14(4), 727-741.
Ohotskii, V.P., et al., Usage of Vacuum Suction During the Primary Surgical Debridement of Open Limb Injuries, Sovetskaya Medicina, 1973, January, 17-20 (in Russian with English translation).
Olenius et al., "Mitotic Activity in Expanded Human Skin." Plastic and Reconstructive Surgery. Feb. 1993. 213-215.
Ontario Ministry of Health and Long Term Care for the Ontario Health Technology Advisory Committee, "Vacuum Assisted Closure Therapy for Wound Care, Health Technology Literature Review," Dec. 2004, Toronto, Ontario, Canada, pp. 1-57.
Ontario, Vacuum Assisted Closure Therapy for Wound Care, Dec. 2004, Toronto, ON, Canada, 1-59.
Orgill, D. P., et al., Microdeformational Wound Therapy—a New Era in Wound Healing, *Tissue Engin. and Wound Healing Laboratory, Brigham and Women's Hospital, Business Briefing: Global Surgery—Future Direction* 2005, 22.
Orgill, D., et al., Current Concepts and Approaches to Wound Healing, Critical Care Medicine, Sep. 1988, 16(9), 899-908.
Orgill, D.P., et al., Guidelines for Treatment of Complex Chest Wounds with Negative Pressure Wound Therapy, *Wounds, a Compendium of Clinical Research and Practice*, Suppl. B, Dec. 2004, 1-23.
Orringer et al., "Management of Wounds in Patients with Complex Enterocutaneous Fistulas," Surgery, Gynecology, & Obstetrics, Jul. 1987, vol. 165, pp. 79-80.
Oschsner, A.J., Surgical Diagnosis and Treatment, 1921, 11, 266-269.
Paradise Valley Hospital, the Center for Wound Healing and Hyperbaric Medicine, Brochure. 3 pgs.
Paradise Vally Hospital, Healthy Living, Newsletter, Fall 2001, 7 pgs.
Parker, M.J. and C. Roberts, Closed suction Surgical Wound Drainage after Orthopaedic Surgery, Cochran Database of Systematic Review 2005, 3, 3 pages.
Parulkar, B.G., et al., Dextranomer Dressing in the Treatment of Infected Wounds and Cutaneous Ulcers, J. Postgrad. Med., 1985, 31(1), 28-33.
Penman, M., What Are the Signs and Symptoms of Gallstones? What Instruments Would You have Ready for the Operation? How Would You Nurse a Case After Operation?, Brit. Journ. Nurs., Aug. 9, 1919, 88.
Pham, C., et al., Vacuum-Assisted Closure for the Management of Wounds: an Accelerated Systematic Review, Asernip-Accelerated Review of Vacuum Assisted Wound Closure, Report No. 27, Dec. 2003, 1-52.
Precision Medical, Easy Go V.A.C Aspirator, http://presicionmedical.com website Downloaded from internet Apr. 10, 2006.
Precision Medical, Power VAC+ Intermittent Aspirator, http://precisionmedical.com Downloaded from internet Apr. 10, 2006, 2 pages.
Press Release for BlueSky by McClanahan and Clearman, LLP, Judge Enters Judgment Upholding BlueSky Medical Verdict in Wound-Care Patent Battle, San Antonio PR/Newswire, Downloaded from Internet Aug. 30, 2006.
Press Release, BlueSky Medical Group, Inc., BlueSky Leads Fire Victim Releif Effort in San Diego Area, http://blueskymedical.com, Mar. 31, 2006.
Press Release, BlueSKy Medical Group, Inc., BlueSky Wins Key Jury Verdict. Aug. 3, 2006.
Press Release, BlueSky Medical Group, Inc., Department of HHS to Review Reimbursement in NPWT Area, http://blueskymedical.com, Mar. 29, 2006.

(56) References Cited

OTHER PUBLICATIONS

Press Release, BlueSky Medical Group, Inc., European Patent Office to Rule on KCI Patent, Downloaded from internet, http://blueskymedical.com, Mar. 29, 2006.
Press Release, BlueSky Medical Group, Inc., Request for Decrease in Reimbursement for NPWT, http://blueskymedical.com, Mar. 30, 2006.
Press Release, BlueSky Medical Group, Inc., Request for Investigation in Potential Unfair Trade Practices, Downloaded from internet, http://blueskymedical.com, Mar. 30, 2006.
Prevena™ Incision Management System, Clinician Guide, pp. 1-9, Jan. 2010.
Prevena™ Incision Management System, Patient Guide, pp. 1-2, Jan. 2010.
Johnson, P., "The Use of Continuous Negative Pressure after Laryngectomy and Radical Neck Dissection", Surgery, Gynecology & Obstetrics, Aug. 1956, pp. 244-246, USA.
Raffl, A., "Use of Negative Pressure Under Skin Flaps After Radical Mastectomy", Dept. of Surgery, State Univ. of N.Y., College of Medicine, Syracuse, NY, submitted for publication Apr. 1953, p. 1048, USA.
Ramirez, O.M. et al., "Optimal Wound Healing under Op-Site Dressing", Ideas and Innovations, Plast Reconstr Surg., vol. 73(3), pp. 474-475.
Rammensee, H.G., Untersuchung der Lymphozytenin filtrate in Implantierte PVA-Schwämme nach der Therapie infizierter Wunden mit Vakuumversiegelung, Aus dem Interfakulatären Institut für Zellbiologie der Universität Tübingen Abeilung Immunologie Abteilungsleter, 2004, 119 pgs.
Ranson, John H. M.D., "Safer Intraperitoneal Sump Drainage", Surgery Gynecology and Obstetrics, pp. 841-842, 1973 vol. 137.
Redon, H. and J. Troques, La Fermeture Sous Depression des Plaies Etendues, Academie de Chirurgie, Mar. 1954, 304-306. (in French).
Redon, H., Closure of Large Wounds under a Partial Vacuum, Paris, Notes on Practical Medicine, published under L. Rouques, 1-3.
Reedy, J., The Science Behind Wound Healing, UW Health Sciences/ UW Medicine News and Community Relations, Winter/Spring 2005, 4 pages.
Reference Handbook of the Medical Sciences, Hyperaemia, 553.
Reid, D., "Information on Cupping or Using Suction Cups on Wounds and for Healing Purposes", Chinese Herbal Medicine, 2 pages.
Reimann, D., et al., Successful Treatment Due to Vacuum Seal Technique of a Severe Scedosporium Apiospermum Skin Infection in a Renal Transplant Recipient, Nephrol. Dial. Transplant, 2004, 19 (1), 245-248.
Renner, R., et al., Vacuum Therapy in dermatology: a Review. JDDG, 2006, 4, 468-476.
Retro Search, Wound Drainage citations, Biological Abstracts, Downloaded from Internet, http://www.nerac.com, Dec. 4, 2001, 1-213.
Richter, Treatment of Inflammatory Conditions of the Skin with Hot Baths, Brit. Journ. Nurs., Aug. 25, 1906, 149.
Roberts, R.H., et al., Randomised Trial of Medinorm LVS and Surgivac Drainage System after Operations for Breast Cancer May 1999, Amer. Journ. Surg., Feb. 1997, 2 pgs.
Robertson, "The Influence upon Wound Contraction of a Negative Interstitial Fluid Pressure Within Granulation Tissue, " Journal of Anatomy, 1969, vol. 105, No. 1, pp. 189.
Rodrigo, J. J. et al., The Effect of Varying Degrees of Suction Pressure on Drainage of Hematomas, Dept. of Orthopaedic Surgery, University of California, David, Sacramento, California, 9 pages (date N/A).
Rosser, C.J., et al., A New Technique to Manage Perineal Wounds, Infections in Urology, Mar./Apr. 2000, 4 pgs.
Royle, G.T. and B.J. Britton, Disposable Drains, Articles of the Royal College of Surgeons of England, (1984), vol. 66, 1 page.
Russ and Fleischmann, Vakuumversiegelung, List of References (in English and German), 2000, 4 pgs.

Safronov, A. A., "Vacuum Therapy of Trophic Ulcers of the Lower Leg with Simultaneous Autoplasty of the Skin", Ministry of Public Health of the USSR, Central Scientific Research Institute of Traumatolog and Orthopedics, 1967.
Sagi, A., Burn Hazard from Cupping—an Ancient Universal Medication Still in Practice, burns, 1988, 14(4), 323-325.
Sames, C.P., Sealing of Wounds with Vacuum Drainage, Br. Med. Journ., Nov. 5, 1977, p. 1223, Correspondence.
Samson, D., et al., Wound-Healing Technologies: Low-Level Laser and Vacuum-Assisted Closure, Evidence report/Technology Assessment, No. 111, Dec. 2004, AHRQ Publication No. 05-E005-2 97 pages.
Sandahl, L., Slides at Geisinger Medical Center, Danville, PA, Apr. 10, 1990, Correspondence, 4 pages.
Sartipy, U. et al., Cardiac Rupture During Vacuum-Assisted Closure Therapy, Ann. Thorac. Surg. 2006, 82, 1110-1111.
Schaffer, D.B., Closed Suction Wound Drainage, Nursing97, Nov., Downloaded from internet www.springnet.com, 62-64. 1997.
Schaum, K.D., Payment Strategies: a New Medicare Part B Wound Care Policy, Advance in Skin and Wound Care, Sep./Oct. 2001, 14(5), 238-240.
Schein et al., "The 'Sandwich Technique' in the Management of the Open Abdomen," British Journal of Surgery, 1986, vol. 73, May, pp. 369-370.
Schumann, D., Preoperative Measures to Promote Wound Healing, Nursing Clinics of North America, Dec. 1979, 14(4), 683-699.
Schwab, P. et al., "Primary closure of the Perineal Wound After Proctectomy", Mayo Clinic Proc., Mar. 1974, pp. 176-179, vol. 49, USA.
Scott, F., "Babies in Bottles", Advance for Respiratory Care Practitioners, Nov. 23, 1992, in 2 pages.
Senyutovich, R.V., "Napkin Preventing Abdominal Contamination in Performance of Colonic Anastomosis", Abstracts, Surgery No. 1, 1997, in 1 page. URL: http://www.mediasphera.ru/surgery/97/1/el-97ref.htm.
Shaer, W.D et al., "Inexpensive Vacuum-Assisted Closure Employing a Conventional Disposable Closed-Suction Drainage System", Plastic and Reconstructive Surgery, Jan. 2001, p. 292, in 1 page.
Sheen, A.W., Some Experiences of Shell Wounds in the Present War, (excerpt), the British Journal of Nursing, Jan. 16, 1915, p. 42, in 1 page.
Sheppard, M.D. et al., "Sealed Drainage of Wounds", The Lancet, Jun. 14, 1952, pp. 1174-1176, in 3 pages.
Silvis, R. et al., "The Use of Continuous Suction Negative Pressure Instead of Pressure Dressing", Annals of Surgery, Aug. 1955, vol. 142, No. 2, pp. 252-256, in 5 pages.
Smith, L. A. et al., "Vacuum Pack Technique of Temporary Abdominal Closure: a Four-Year Experience", the American Surgeon, Dec. 1997, vol. 63(12), pp. 1102-1108, in 7 pages.
Smith & Nephew, "PICO Single Use Negative Pressure Wound Therapy System", spiral booklet, Mar. 2011, in 7 pages.
Solovev et al., "The Method of Treatment of Immature External Fistulas in the Upper Gastrointestinal Tract," USSR Ministry of Health, S.M. Kirov Gorky State Medical Institute, 1987. (with English translation).
Solovev, V.A. "Treatment and Prevention of Suture Failures after Gastric Resection" (Dissertation Abstract) (S.M. Kirov Gorky State Medical Institute, Gorky USSR 1988).
SPAHN, Slide presented at the WOCN meeting in Ontario, California, Sep. 2001.
"Power Source Multi-Purpose Surgical Aspirator", Sparta Instrument Corp., 26602 Corporate Ave., Hayward, CA 94545, in 1 page.
Specific Inflammations, Diseases of the Skin, pp. 549-550, in 2 pages.
Spengler, M. et al., "Performance of Filtered Sump Wound Drainage Tubes", Surgery, Gynecology & Obstetrics, Mar. 1982, pp. 333-336, vol. 54, USA, in 4 pages.
Steenvoorde, P. et al., "Failure of the Topical Negative Pressure Abdominal Dressing System in the "Fat" Open Abdomen: Report of a Case and Review of the Literature", Wounds, 2006, vol. 18(2), pp. 44-50, in 6 pages.

(56) References Cited

OTHER PUBLICATIONS

Stewart, J., Ph.D., "Next generation products for wound management", World Wide Wounds, Nov. 2002, in 13 pages. URL: http://www.worldwidewounds.com/2003/april/Stewart/Next-Generation-Products.html.
Stewart, M. F. et al., "Cleaning v Healing", Community Outlook, Aug. 1985, pp. 22-26, in 3 pages.
Suarez, L., "NPWT vs Standard Care: Which is the Better Treatment for Complex Wounds?", Diabetic Microvascular Complications Today, Jan./Feb. 2006, pp. 26-27, in 2 pages.
Summit Medical, "LowVac Plus", Feb. 1, 2006, in 1 page, downloaded from http://www.summit-medical.co.uk.
Sterion Incorporated, "SURGIDYNE, Closed Systems for Management of Wound Drainage", brochure and catalog, [dated unavailable], downloaded from www.sterion.com, in 6 pages.
Svedman, P., "Irrigation Treatment of Leg Ulcers," The Lancet, Sep. 3, 1983, pp. 532-534, in 3 pages.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133, in 9 pages.
Swanson, L., "Solving stubborn-wound problem could save millions, team says", JAMC, Feb. 23, 1999, vol. 160(4), p. 556, in 1 page.
Swift, S. et al., "Quorum Sensing in Aeromonas hydrophila and Aeromonas salmonicida: Identification of LuxR1 Homologs AhyRI and AsaRI and Their Cognate N-Acylhomoserine Lactone Signal Molecules", J. Bacteriol., 1997, vol. 179(17), pp. 5271-5281, in 12 pages.
Taylor, V., "Meeting the Challenge of Fistulas & Draining Wounds", Nursing, Jun. 1980, pp. 45-51, USA, in 7 pages.
"HiBlow Air Pump", Techno Takatsuki., Co., Ltd., 8-16 Hatchonishimachi, Takatsuki City, Osaka, Japan, in 5 pages.
Teder, H. et al., "Continuous Wound Irrigation in the Pig," Journal of Investigative Surgery, 1990, vol. 3, pp. 399-407, in 9 pages.
Tennant, C.E., "The Use of Hyperemia in the Postoperative Treatment of Lesions of the Extremities and Thorax," Journal of American Medical Association, May 8, 1915, pp. 1548-1549, in 2 pages.
Tenta, L.T. et al., "Suction Drainage of Wounds of the Head and Neck", Surg. Gyn. & Ob., Dec. 1989, vol. 169, p. 558, in 1 page.
"The Bier Treatment", the British Journal of Nursing, Jun. 6, 1908, p. 452, in 1 page.
The British Journal of Nursing, Nov. 4, 1911, p. 368, in 1 page (title of article unknown).
Thomas, S., "Comparative Review of the Properties of Six Semipermeable Film Dressings", the Pharmaceutical Journal, Science and Technology, Jun. 18, 1988, pp. 785-788, in 7 pages.
Thomas, S., "Wound Management and Dressings", 1990, pp. 35-42.
Tittel, K. et al., "Forum: VariDyne—Neue Standards in der Postoperative Wunddrainage" (New Standards in Postoperative Wound Drainage), Unfallchirurgie, 1988, vol. 14(2), pp. 104-107 (in German with English Translation), in 6 pages.
Tribble, D., "An Improved Sump Drain-Irrigation Device of Simple Construction", Archives of Surgery New York, pp. 511-513, 1972, vol. 105, in 4 pages.
Tricenturion, article for Negative Pressure Wound Therapy Pumps—Policy Article, CMS, Jan. 2006, downloaded from internet, in 4 pages. URL: www.hhs.gov.
"Tuberculous Joints", The Nursing Record & Hospital World, Apr. 28, 1894, p. 280, in 1 page.
Brubacher, L. "The RN Magazine/University of California Continuing Education Curriculum; Examination on 'To heal a draining wound'", RN, Mar. 1982, p. 36, USA, in 1 page.
Unknown, Medela product information with English Summary: "Pleupump MK II is the new micro-data controlled thoracic drainage".
Urschel, J. D. et al., "The Effect of Mechanical Stress on Soft and Hard Tissue Repair; a Review", British Journal of Plastic Surgery, 1988, vol. 41, pp. 182-186, in 5 pages.
US Medco Healthcare, Healing through Technology, HYPO Wound Therapy System, downloaded from internet Apr. 18, 2006, in 8 pages. URL: http://www.usmedco.net.
Usupov, Y. N., et al., "Active Wound Drainage", the Kremlin Papers: Perspectives in Wound Care, Russian Journal: Vestnik Khirurgii, BlueSky Publishing, La Costa, California (2004), 8-10.
Usypov, Y. N. and M.V. Ephfanov, Active Drainage of wounds, Dept. of Hospital Surgery, Army Medical Academy, Leningrad, Vestnik Chirurgia 1987, April Edition, 42-45 (in Russian with English translation).
Valenta, A. L., "Using the Vacuum Dressing Alternative for Difficult Wounds", AIN, Apr. 1994, pp. 44-45, in 2 pages.
Van Heurn, L. W. E. et al., "Prospective Randomized Trial of High versus Low Vacuum Drainage after Axillary Lymphadenectomy", British Journal of Surgery, 1995, vol. 82, pp. 931-932, in 4 pages.
Van Way III, C.W., "Prevention of Suction-Induced Gastric Mucosal Damage in Dogs", Critical Care Medicine, Aug. 1987, vol. 15(8), pp. 774-777, in 4 pages.
Varley, G.W. et al., "Wound Drains in Proximal Femoral Fracture Surgery: a Randomized Prospective Trial of 177 Patients", J. R. Coll. Surg. Edinb., Dec. 1995, vol. 40, pp. 416-418, in 3 pages.
Venturi, M. L., "Mechanisms and Clinical Applications of the Vacuum-Assisted Closure (VAC) Device", Am J Clin Dermatol, 2005, vol. 6(3), pp. 185-194, Review Article (2005), in 10 pages.
Vijanto, J. et al., "Local Hyperalimentation of Open Wounds", Br. J. Surg., 1976, vol. 63, pp. 427-430, in 4 pages.
Wackenfors, A. et al., "Effects of Vacuum-Assisted Closure Therapy on Inguinal Wound Edge Microvascular Blood Flow", Wound Rep. Reg, 2004, vol. 12(6), pp. 600-606, in 7 pages.
Warren, J.C. et al., Ed., "The International Text-Book of Surgery", 1902, vol. 1, pp. 70-79, in 11 pages.
Waymack, J. P. et al., "An evaluation of Aquaphor Gauze dressing in burned children", Burns Include Therm Inj., Aug. 1986, vol. 12(6), pp. 443-438.
Wayne, M.A., "Cook Pneumothorax Catheter Set, Wayne Pneumothorax Catheter Set", Cook Critical Care, Cook Incorporated 1997, in 3 pages.
Webb, L., "New Techniques in Wound Management: Vacuum-Assisted Wound Closure", Journal of the American Academy of Orthopaedic Surgeons, vol. 10(5), pp. 303-311, Sep. 2002, in 9 pages.
Webster's Revised Unabridged Dictionary, published 1913 by C. & G. Merriam Co., definition of "Flapper Valve", downloaded from Free Online Dictionary, in 2 pages.
Wells Johnson Company, 2045 N. Forbes Blvd., Suite 106, Tuscon, AZ, "Suction Tips", in 1 page.
Wells Johnson Company, 2045 N. Forbes Blvd., Suite 106, Tuscon, AZ. "Point 5 Aspirator", in 1 page.
Westaby, S. et al., "A Wound Irrigation Device", The Lancet, Sep. 2, 1978, pp. 503-504, in 2 pages.
Westaby, S., "Wound Care No. 11", Nursing Times, Jul. 21, 1982, pp. 41-48, in 8 pages.
White, R.A. et al., "Vacuum-Assisted Closure Complicated by Erosion and Hemorrhage of the Anterior Tibial Artery", Journal of Orthopaedic Trauma, Jan. 2005, vol. 19(1), pp. 56-59, abstract cited in BlueSky internal email dated Nov. 9, 2005, 1 page.
Williams, J. et al., "Survey of the Use of Suction Drains in Head and Neck Surgery and Analysis of their Biomechanical Properties", J. Otolaryngol., Feb. 2003, vol. 32(1), pp. 16-22, abstract downloaded from internet Nov. 30, 2003, in 1 page.
"Windows on Medical Technology—Vacuum-Assisted Wound Closure for Chronic and Acute Wounds", ECRI Health Technology Assessment Information Service, Oct. 2000, 38, pp. 1-21, in 25 pages.
Witkowski, J.A. et al., Synthetic Dressings: Wound Healing in the '80s, Hospital Therapy, Nov. 1986, pp. 75-84, in 15 pages.
Wolthuis, R. et al., "Physiological Effects of Locally Applied Reduced Pressure in Man," Physiological Reviews, Jul. 1974, pp. 566-595 vol. 54, No. 3, USA, in 30 pages.

(56) References Cited

OTHER PUBLICATIONS

Wooding-Scott, M. et al., "No Wound is Too Big for Resourceful Nurses," RN, Dec. 1988, pp. 22-25, USA, in 4 pages.

Worth, M.H. et al., "The Effectiveness of Bacterial Filtration in Vented Wound Drains", Journ. of Surg. Research, 1979, vol. 27, pp. 405-407, in 3 pages.

Wright, P., "Sales Soar for BlueSky's Wound-Healing Device", North County Times, Nov. 2006, D-1 and D-6 (newspaper article), in 1 page.

Wu, P. et al., "In Vitro Assessment of Water Vapour Transmission of Synthetic Wound Dressings", Biomaterials, 1995, vol. 16(3), pp. 171-175, in 5 pages.

Wu, W.S. et al., "Vacuum therapy as an intermediate phase in wound closure: a clinical experience", Eur J Past Surg, 2000, vol. 23, pp. 174-177.

Wysocki, A. et al., "Wound Fluid form Chronic Leg Ulcers Contains Elevated Levels of Metalloproteinases MMP-2 and MMP-9", the Society for Investigative Dermatology, Inc., Jul. 1993, pp. 64-68.

Yukhtin, V.I. et al., "Surgical Treatment of Purulent Diseases of Soft tissues and Bones with the Use of Drainage-Bathing System", Contents, Surg. No. 9, 1997, downloaded from internet, in 1 page. URL: http://www.mediasphera.ru/surgery/97/9/e9-97ref.htm.

Zamierowski, D., Letter: "All Foam Sponges are not Equal in Vacuum Dressings," British Journal of Plastic Surgery, 1999, 52, 78-81, p. 79, United Kingdom.

Zhetimkarimov, D.S. et al., "The Applied Significance of Anatomic Peculiarities of Greater Omentum", Contents, Surg. No. 6, 1997, downloaded from internet, in 1 page. URL: http://www.mediasphera.ru/surgery/97/6/e6-97ref.htm.

Zivadinovic, G. et al., "Our Experience in the Treatment of Patients with Arterial Failure of the Extremities Using the Vacusac Unit", Timocki Medicinski Glasnik, Year XII, Zajecar, 1987, No. 1, pp. 55-65, in 12 pages.

Zivadinovic, G. et al., "Vacuum Therapy in the Treatment of Peripheral Blood Vessels", Timocki Medicinski Glasnik (Conference Papers of the 5th Timok Medical Days, Majdanpek, 1986), Year XI, Zajecar, 1986, No. 3-4, with English translation, pp. 161-164, in 10 pages.

"Technology Watch", May 1989, in 1 page.

Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.

Protz, K., "Moderne Wundauflagen unterstutzen Heilungsprozess", Wundversorgung: Indikation und Anwendung, Geriatrie Journal, Apr. 2005, pp. 3333-3339, with translation, in 17 pages.

\* cited by examiner

REDUCED PRESSURE TREATMENT APPLIANCE

CROSS-REFERENCE TO RELATED APPLICATIONS

This application is a continuation application of U.S. application Ser. No. 14/949,624, filed Nov. 23, 2015, which is a continuation application of U.S. application Ser. No. 13/902,446, filed May 24, 2013, and issued as U.S. Pat. No. 9,198,801, which is a continuation application of U.S. application Ser. No. 12/832,031, filed Jul. 7, 2010, and issued as U.S. Pat. No. 8,449,509, which is a continuation of U.S. application Ser. No. 11/098,265, filed Apr. 4, 2005, and issued as U.S. Pat. No. 7,909,805, which claims the benefit of U.S. Provisional Application No. 60/559,727, filed Apr. 5, 2004, and which is also a continuation-in-part of U.S. patent application Ser. No. 11/064,813, filed Feb. 24, 2005, and issued as U.S. Pat. No. 8,062,272. The disclosures of these prior applications are hereby incorporated by reference in their entirety.

BACKGROUND

The present invention generally relates to treatment of wounds, and more specifically to an improved apparatus and method for treating all or a portion of a wound on a body by applying reduced pressure to the portion of the wound for which treatment is desired. In this context, the terms "wound" and "body" are to be interpreted broadly, to include any body part of a patient that may be treated using reduced pressure.

The treatment of open or chronic wounds that are too large to spontaneously close or otherwise fail to heal by means of applying reduced pressure to the site of the wound is well known in the art. One such system is disclosed in U.S. patent application Ser. No. 10/652,100, which was filed by the present inventor with the U.S. Patent and Trademark Office on Aug. 28, 2003. The disclosure of this U.S. patent application is incorporated herein by reference. Another system is disclosed in a U.S. patent application entitled "Improved Reduced Pressure Wound Treatment Appliance," which was filed by the present inventor with the U.S. Patent and Trademark Office on or about Dec. 30, 2004. The disclosure of this U.S. patent application is also incorporated herein by reference.

Reduced pressure wound treatment systems currently known in the art commonly involve placing a cover that is impermeable to liquids over the wound, using various means to seal the cover to the tissue of the patient surrounding the wound, and connecting a source of reduced pressure (such as a vacuum pump) to the cover in a manner so that an area of reduced pressure is created under the cover in the area of the wound. However, the covers currently known and used in the art have a number of disadvantages. For example, in one version they tend to be in the form of a flexible sheet of material that is placed over the wound and sealed to the surrounding tissue using an adhesive, adhesive tape, or other similar means. As tissue swelling in the area of the wound decreases during the healing process, the adhesive may begin to stretch the surrounding tissue, as well as tissue within the wound, resulting in discomfort and pain to the patient. This may necessitate more frequent cover changes, increasing the time medical staff must expend in treating the wound. This additional time, of course, also tends to increase the expense involved in treating the wound. In addition, these types of covers can typically only be used where there is normal tissue adjacent to the wound to which the adhesive seal can be attached. Otherwise, the seal must be made in a portion of the area of the wound, and exudate from the wound tends to break the seal so that reduced pressure cannot be maintained beneath the wound cover. Thus, such covers (and many other covers requiring adhesive seals) may typically only be used to treat an entire wound, as opposed to only a portion of a wound. Further, the adhesive seal creates discomfort for the patient when the sheet cover is removed. In other versions, the covers tend to be rigid or semi-rigid in nature so that they are held away from the surface of the wound. In these versions, the covers are sometimes difficult to use because the shape and contour of the patient's body in the area of the wound do not readily adapt to the shape of the cover. In such cases, additional time is required for the medical staff to adapt the cover for its intended use. This also increases the expense of wound treatment. In addition, it is also often necessary to use an adhesive, adhesive tape, or other similar means to seal the rigid or semi-rigid cover to the tissue surrounding the wound. In these instances, the same disadvantages discussed above with respect to the first version also apply to this version as well. In still other cases, the rigid and semi-rigid covers must be used with padding in the area where the cover is adjacent to the patient to prevent the edges of the cover from exerting undue pressure on the tissue surrounding the wound. Without the padding, the patient may experience pain and discomfort. The additional padding, which may make the cover itself more expensive, may also take a greater amount of time to place on the patient for treatment purposes. These covers may also have the problem of placing tension on the surrounding tissue as the swelling in the area of the wound decreases during the healing process. In yet another version, covers are constructed of combinations of flexible materials and rigid materials. In these versions, a flexible member, such as a flexible sheet, is typically supported by a rigid or semi-rigid structure that is either placed between the flexible member and the wound or in the area above and outside the flexible member. In either case, the flexible member must usually be sealed to the tissue surrounding the wound using an adhesive, adhesive tape, or other similar means. This seal creates the same problems described above. In addition, the same problems described above with respect to rigid and semi-rigid structures are also often present. In all of the versions described above, it may be difficult to tell if reduced pressure in the area of the wound under the cover has been lost because the cover itself does not generally provide a visual clue of such loss.

Therefore, there is a need for a reduced pressure wound treatment system that has a means to enclose all or a portion of a wound without the need for an adhesive seal. There is also a need for such enclosing means to be flexible, so that it adapts to changing shapes and contours of the patient's body as wound healing progresses. Further, there is a need for an enclosing means that is adaptable to a wide variety of patient body shapes and contours. There is also a need for an enclosing means that is simple to apply to the patient's body, and simple to remove from the patient's body. Such enclosing means would also take less time to apply and remove, reducing the expense involved in wound treatment. There is also a need for an enclosing means that is relatively inexpensive, while meeting the needs described above. In addition, there is a need for an enclosing means that may be used within the wound (or a portion thereof), without the need to seal the enclosing means to normal tissue surrounding the wound. Further, there is a need for an enclosing means that flexes with movement of the portion of the body surrounding the wound, without the need for an adhesive seal or rigid or semi-rigid structure. Finally, there is a need for an enclosing means that provides a visual clue of loss of reduced pressure in the area of the wound under the enclosing means.

SUMMARY

The present invention is directed to a reduced pressure wound treatment appliance and methods that satisfy the needs described above. As described in greater detail below, they have many advantages over existing reduced pressure wound treatment apparatus and methods when used for their intended purpose, as well as novel features that result in a new reduced pressure wound treatment appliance and methods that are not anticipated, rendered obvious, suggested, or even implied by any of the prior art apparatus or methods, either alone or in any combination thereof.

In accordance with the present invention, a wound treatment appliance is provided for treating all or a portion of a wound by applying reduced pressure (i.e., pressure that is below ambient atmospheric pressure) to the portion of the wound to be treated in a controlled manner for a selected time period in a manner that overcomes the disadvantages of currently existing apparatus. The application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

In a first aspect of a first version of the present invention, the wound treatment appliance is comprised of an impermeable flexible overlay and reduced pressure supply means, which are described in more detail below and are used to connect the flexible overlay to a reduced pressure supply source that provides a supply of reduced pressure to the flexible overlay. In this first aspect of the first version of the invention, the flexible overlay is adapted to be placed over and enclose all or a portion of a wound on the surface of the body of a patient. The flexible overlay is also adapted to maintain reduced pressure under the flexible overlay in the area of the wound. The flexible overlay collapses in the approximate direction of the area of the wound to be treated when reduced pressure is supplied to the volume under the flexible overlay in the area of the wound. This collapse causes the formation of an approximately hermetic seal (described in more detail below) between the flexible overlay and the body in the area of the wound. In some embodiments of this first aspect of the first version of the invention, the flexible overlay is further comprised of an interior surface facing the area of the wound to be treated, wherein the surface area of the interior surface is greater than the surface area of the portion of the body to be enclosed by the flexible overlay. In other embodiments of this first aspect of the first version of the invention, the flexible overlay is further comprised of a bottom portion having an approximately elongated conical shape with an approximately elliptically-shaped open end at the base of the elongated conical bottom portion. In these embodiments, the approximately elliptically-shaped open end at the base is sized to be placed over and enclose the area of the wound to be treated. In yet other embodiments of this first aspect of the first version of the invention, the flexible overlay (as opposed to only the bottom portion thereof) has an approximately elongated conical shape having an approximately elliptically-shaped open end at its base. In these embodiments, the approximately elliptically-shaped perimeter of the open end at the base of the flexible overlay is positioned over all or a portion of the wound on the surface of the body. In some of these embodiments, the flexible overlay further comprises a port located approximately at the apex of the elongated conically-shaped flexible overlay. In these embodiments, the reduced pressure supply means is operably connected to the port. In yet other embodiments of this first aspect of the first version of the invention, the flexible overlay is comprised of at least three cover portions, each of such cover portions being approximately triangular in shape. One point of each of the at least three triangular-shaped cover portions are joined to form an apex of the flexible overlay and one side of each at least three triangular-shaped cover portions adjacent to the apex is joined to an adjacent side of another of such at least three triangular-shaped cover portions so that the bases of the at least three triangular-shaped cover portions form an opening sized to be placed over and enclose the area of the wound to be treated. In some of these embodiments, the flexible overlay is further comprised of a port located approximately at the apex of the flexible overlay and the reduced pressure supply means is operably connected to the port. In yet other embodiments, the flexible overlay may be cup-shaped. In still other embodiments of this first aspect of the first version of the invention, at least one fold forms in the surface of the flexible overlay when it collapses, so that fluids aspirated by the wound flow along the at least one fold to the reduced pressure supply means, where they are removed from the flexible overlay by means of the reduced pressure supply means cooperating with the reduced pressure supply source. In other embodiments, the flexible overlay is further comprised of suction assist means, which assist in the application of reduced pressure to the area of the wound and removal of exudate from the wound. In some of these embodiments, the suction assist means may be channels disposed in, or raised portions disposed on, the surface of the flexible overlay. In other embodiments, the appliance further comprises supplemental sealing means, which are described in more detail below, to form a seal between the flexible overlay and the body in the area of the wound. In yet other embodiments, the appliance further comprises a suction drain and suction drain connecting means, which are described in more detail below, to operably connect the reduced pressure supply means to the suction drain so that the suction drain is in fluid communication with the reduced pressure supply means and reduced pressure is supplied to the volume under the flexible overlay in the area of the wound by means of the suction drain. The suction drain extends from the reduced pressure supply means into the volume under the flexible overlay in the area of the wound.

In a second aspect of the first version of the present invention, the wound treatment appliance is comprised of a wound treatment device and a vacuum system. In this second aspect of the first version of the invention, the vacuum system is further comprised of a reduced pressure supply source that provides a supply of reduced pressure and reduced pressure supply means to operably connect the wound treatment device to the reduced pressure supply source, so that the volume under the wound treatment device in the area of the wound is supplied with reduced pressure by the reduced pressure supply source. In various embodiments of this second aspect of the first version of the invention, the wound treatment device and the reduced pressure supply means may generally have substantially the same structure, features, characteristics and operation as the appliance described above in connection with the first aspect of the first version of the invention.

In some embodiments of this second aspect of the first version of the invention, the reduced pressure supply source is comprised of a vacuum pump. In some of these embodiments, the reduced pressure supply source further comprises a control system for the vacuum pump, wherein the control system may control at least the level of suction produced by the vacuum pump or the rate of fluid flow produced by the vacuum pump, or any combination of rate of suction and rate of fluid flow of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms aspirated from the wound or fluids aspirated from the wound or both. In yet other embodiments, the vacuum pump is comprised of a portable vacuum pump. In still other embodiments of this second aspect of the first version of the invention, the reduced pressure supply means is comprised of flexible tubing. In other embodiments, the reduced pressure supply means is further comprised of a collection system that is operably positioned between the wound treatment device and the reduced pressure supply source. In some of these embodiments, the collection system comprises a container to receive and hold fluid aspirated from the wound and pressure halting means to halt the application of reduced pressure to the wound when the fluid in the container exceeds a predetermined amount. In other embodiments of this second aspect of the first version of the invention, the reduced pressure under the flexible overlay in the area of the wound is in the range from approximately 20 mm of Hg below atmospheric pressure to approximately 125 mm of Hg below atmospheric pressure. In yet other embodiments, the reduced pressure is applied in a cyclic nature, the cyclic nature providing alternating time periods of application of reduced pressure and without application of reduced pressure. In some embodiments of this second aspect of the first version of the invention, the wound treatment appliance further comprises tissue protection means, which are described in more detail below, to protect and strengthen the body tissue that is adjacent to the flexible overlay at the wound site. In some of these embodiments, the tissue protection means is a hydrocolloid material.

In a third aspect of the first version of the invention, the wound treatment appliance is comprised of a wound treatment device, a vacuum system, and wound packing means, which are described in more detail below, that are positioned between the wound treatment device and the portion of the wound to be treated. In various embodiments of this third aspect of the first version of the invention, the wound treatment device and the vacuum system may generally have substantially the same structure, features, characteristics and operations as the wound treatment device and the vacuum system, respectively, described above in connection with the second aspect of the first version of the invention. In this third aspect of the first version of the invention, the flexible overlay of the wound treatment device is placed over all or a portion of the wound and the wound packing means when the flexible overlay is positioned on the surface of the body at the wound site. In some embodiments of this third aspect of the first version of the invention, the wound packing means is comprised of absorbent dressings, antiseptic dressings, nonadherent dressings, water dressings, or combinations of such dressings. In some of these embodiments, the wound packing means is preferably comprised of gauze or cotton or any combination of gauze and cotton. In still other embodiments, the wound packing means is comprised of an absorbable matrix adapted to encourage growth of the tissue in the area of the wound under the flexible overlay into the matrix. The absorbable matrix is constructed of an absorbable material that is absorbed into the epithelial and subcutaneous tissue in the wound as the wound heals. Because of the absorbable nature of the absorbable matrix, the matrix should require less frequent changing than other dressing types during the treatment process. In other circumstances, the matrix may not need to be changed at all during the treatment process. In some of these embodiments, the absorbable matrix is comprised of collagen or other absorbable material. In some embodiments of this third aspect of the first version of the invention, the appliance further comprises a suction drain and suction drain connecting means, which are described in more detail below, to operably connect the reduced pressure supply means to the suction drain so that the suction drain is in fluid communication with the reduced pressure supply means and reduced pressure is supplied to the volume under the impermeable flexible overlay in the area of the wound by means of the suction drain. In these embodiments, the suction drain extends from the reduced pressure supply means into the volume under the impermeable flexible overlay in the area of the wound. In some of these embodiments, the suction drain is further comprised of a distal end portion and the distal end portion has at least one perforation in the surface thereof. In some of these embodiments, the distal end portion of the suction drain is positioned within the interior volume of the wound packing means.

In a fourth aspect of the first version of the invention, the wound treatment appliance is comprised of a wound treatment device and a vacuum system. In various embodiments of this fourth aspect of the first version of the invention, the wound treatment device is comprised of an impermeable flexible overlay and a seal. The impermeable flexible overlay is sized to be placed over and enclose the area of the wound to be treated and is adapted to maintain reduced pressure in the area of the wound to be treated. The seal seals the impermeable flexible overlay to the body in the area of the wound in a manner so that reduced pressure is maintained under the impermeable overlay in the area of the wound to be treated. In addition, in the various embodiments of this fourth aspect of the first version of the invention, the vacuum system is comprised of a suction bulb, which may (but not necessarily) provide a source of reduced pressure, and reduced pressure supply means, which are described in more detail below, to operably connect the impermeable flexible overlay to the suction bulb, so that the area of the wound under the impermeable flexible overlay may be supplied with reduced pressure by the suction bulb. In some embodiments of this fourth aspect of the first version of the invention, the flexible wound cover may be comprised of a flexible overlay that has substantially the same structure, features, characteristics and operation as the flexible overlay described above in connection with the first aspect of this first version of the invention. In some embodiments of this fourth aspect of the first version of the invention, the suction bulb is further comprised of an inlet port and an outlet port, wherein the inlet port is operably connected to the reduced pressure supply means, and the vacuum system further comprises an exhaust tubing member operably connected to the outlet port. In some of these embodiments, the vacuum system further comprises an exhaust control valve operably connected to the exhaust tubing member. In other embodiments, the vacuum system is further comprised of a filter operably connected to the exhaust tubing member, which prevents the venting of micro-organisms aspirated from the wound or fluids aspirated from the wound or both. In yet other embodiments, the vacuum system is further comprised of a supplemental vacuum system that is operably connected to the exhaust tubing member. In these embodiments, the supplemental vacuum system may generally have substantially the same structure, features, characteristics and operation as the vacuum system described above in connection with the second and third aspects of the first version of the invention.

A fifth aspect of the first version of the present invention discloses a method of treating a wound on a body. In one embodiment of this fifth aspect of the first version of the invention, the method comprises the following steps. First, positioning an flexible overlay on the body over the area of the wound to be treated, wherein the flexible overlay is sized to be placed over and enclose the area of the wound to be treated and adapted to maintain reduced pressure in the area of the wound to be treated. Second, operably connecting the flexible overlay with a vacuum system for producing reduced pressure in the volume under the flexible overlay in the area of the wound to be treated. Third, collapsing the flexible overlay in the approximate direction of the wound when reduced pressure is supplied to the volume under the flexible overlay in the area of the wound so that an approximately hermetic seal (described in more detail below) is formed between the impermeable flexible overlay and the body in the area of the wound. Fourth, maintaining the reduced pressure until the area of the wound being treated has progressed toward a selected stage of healing. In other embodiments of this fifth aspect of the first version of the invention, the method further comprises the step of placing tissue protection means on the tissue of the body that is to be approximately adjacent to the flexible overlay, such step being performed prior to positioning the flexible overlay over the area of the wound to be treated. The tissue protection means, which is described in more detail below, protects and strengthens the tissue of the body adjacent to the flexible overlay at the wound site. In yet other embodiments of this fifth aspect of the first version of the invention, the method further comprises the step of placing wound packing means (described in more detail above) between the wound and the flexible overlay in the area of the wound to be treated, such step being performed prior to positioning the flexible overlay over the area of the wound to be treated. In still other embodiments of this fifth aspect of the first version of the invention, the vacuum system is comprised of a suction bulb and the method further comprises the step of squeezing the suction bulb to reduce its volume and then releasing the suction bulb, so that reduced pressure is produced in the volume under the flexible overlay in the area of the wound. In other embodiments of this fifth aspect of the first version of the invention, the reduced pressure under the impermeable overlay in the area of the wound is in the range from approximately 20 mm of Hg below atmospheric pressure to approximately 125 mm of Hg below atmospheric pressure. In still other embodiments of this fifth aspect of the first version of the invention, the reduced pressure is applied in a cyclic nature, the cyclic nature providing alternating time periods of application of reduced pressure and without application of reduced pressure.

As is illustrated in the detailed descriptions herein, the wound treatment appliance of the present invention meets the needs discussed above in the Background section. For example, in the preferred embodiment of a flexible overlay having a bottom portion with an approximately elongated conical shape, the flexible overlay is placed over and encloses all or a portion of the wound. When the flexible overlay is enclosing all or a portion of the wound, the portions of the flexible overlay positioned adjacent to the surface of the body at the wound site are at (or can be deformed to be at) a relatively acute angle relative to such surface of the body. When reduced pressure is applied to the area under the flexible overlay, the flexible overlay is drawn downward, collapsing the flexible overlay in the approximate direction of the wound. As the flexible overlay collapses, the portions of the flexible overlay adjacent to the perimeter of the opening of the flexible overlay are drawn tightly against the surface of the body at the wound site, thus forming an approximately hermetic seal. References to an "approximately hermetic seal" herein refer generally to a seal that is gas-tight and liquid-tight for purposes of the reduced pressure treatment of the wound. It is to be noted that this seal need not be entirely gas-tight and liquid-tight. For example, the approximately hermetic seal may allow for a relatively small degree of leakage, so that outside air may enter the volume under the flexible overlay in the area of the wound, as long as the degree of leakage is small enough so that the vacuum system can maintain the desired degree of reduced pressure in the volume under the flexible overlay in the area of the wound. In some uses where the collapsing flexible overlay may not produce an approximately hermetic seal that is solely capable of maintaining the reduced pressure in the volume under the impermeable overlay in the area of the wound, it may be necessary to provide supplemental sealing means, which are described in more detail below, and which are used to provide a seal between the portions of the flexible overlay and the body where the approximately hermetic seal is not adequate. As a result, the flexible overlay is simple to apply to the patient. There is also often no need for any other sealing means in most cases, which means that there is usually no need for medical staff to take the time to make a separate seal. Even where the geometry of the surface of the body surrounding the wound may require that supplemental sealing means be used to provide some limited assistance to ensure a seal, the amount of such assistance (such as by applying an adhesive) is limited, especially when compared to current covers in the art. In addition, as swelling of tissue at the wound site decreases, the flexible nature of the flexible overlay allows it to further deform to conform to the changing shape and contours at the wound site. This prevents the patient from being discomforted as the swelling decreases. It also reduces the need to change the covering over the wound as healing progresses. This is generally not true in cases involving flexible, semi-rigid and rigid covers that exist in the art. For example, even where semi-rigid and rigid covers do not utilize an adhesive seal and rely solely upon the reduced pressure to hold them in place, they do not generally change shape enough to flex with substantial changes in the shape and contour of the surrounding body surface. Thus, they may not be appropriate for use with body portions that are subject to such changes, while the flexible nature of the flexible overlay, along with its increased surface area that can bend and flex, allow it to be used in such circumstances without the need for an adhesive seal. In the same way, the flexible overlay may generally be used for unusual geometries of the body at or surrounding the wound because of the overlay's flexible nature and relatively large surface area. In contrast, flexible sheets and semi-rigid and rigid covers may require substantial modification and means to provide an adequate seal. In addition, such covers may require that the patient be partially or wholly immobilized during the treatment process to avoid movement in the area of the body surrounding the wound to avoid breaking the seal. And such covers must usually be sealed to normal tissue surrounding the wound. The flexible overlay, however, may be used within the perimeter of a wound in many cases because there is not typically a need to seal the flexible overlay to normal tissue surrounding the wound. Further, because there is typically no need for an adhesive seal, removal of the flexible overlay merely requires removal of the reduced pressure from the area under the flexible overlay. It is thus simple to remove from the patient. For this reason, it will tend to reduce the time required of medical staff for wound treatment, which will also tend to reduce the cost of wound treatment. In addition, there is no pain and discomfort for the patient when the flexible overlay is removed. Even if a limited amount of supplemental sealing means (such as an adhesive) are required to provide a seal at a portion of the flexible overlay that is adjacent to the surface surrounding the wound, the reduced amount of supplemental sealing means will cause a corresponding reduction in the amount of such pain and discomfort. Further, the preferred embodiments of the collapsed flexible overlay will have folds in its surface while in the collapsed state, so that fluid aspirated by the wound may flow along the folds to be removed from under the flexible overlay. In some embodiments, the flexible overlay is further comprised of suction assist means, which also assist in the application of reduced pressure to the area of the wound and removal of exudate from the wound. In some of these embodiments, the suction assist means may be channels disposed in, or raised portions disposed on, the surface of the flexible overlay. In addition, if reduced pressure is lost under the flexible overlay, the flexible overlay will expand outward from the wound, providing a visual indication that reduced pressure has been lost. Finally, in its preferred embodiments, the flexible overlay is relatively inexpensive to manufacture, even though it meets the described needs.

In a first aspect of a second version of the present invention, the wound treatment appliance is comprised of a fluid impermeable flexible overlay, a collection chamber to receive and hold fluid aspirated from the wound, collection chamber attachment means to operably attach the collection chamber to the flexible overlay, as described in more detail below, and reduced pressure supply means, which are described in more detail below. In this first aspect of the second version of the invention, the flexible overlay is adapted to be placed over and enclose all or a portion of the wound. In the various embodiments of this first aspect of the second version of the invention, except as described in more detail below, the flexible overlay has substantially the same structure, features characteristics and operation as the flexible overlay described above in connection with the first aspect of the first version of the invention: In addition, in this first aspect of the second version of the invention, the reduced pressure supply means is used to operably connect the collection chamber to a reduced pressure supply source that provides a supply of reduced pressure to the collection chamber, so that the volume within the collection chamber and under the impermeable overlay in the area of the wound to be treated are supplied with reduced pressure by the reduced pressure supply source. In the various embodiments of this second version of the invention, except as described in more detail below, the reduced pressure supply means to connect the reduced pressure supply source to the collection chamber in the embodiments of this second version of the invention may have substantially the same structure, features, characteristics and operation as the reduced pressure supply means described above in connection with the first version of the invention.

In this first aspect of the second version of the invention, the flexible overlay is attached by collection chamber attachment means to a collection chamber that receives and holds fluid aspirated from the wound. In some embodiments, the collection chamber may be approximately cylindrical in shape. In the various embodiments of this first aspect of the second version of the invention, the collection chamber attachment means operably attaches the collection chamber to the flexible overlay in a manner so that the fluid and reduced pressure are permitted to flow between the collection chamber and the volume under the flexible overlay in the area of the wound. In some embodiments of this first aspect of the second version of the invention, the collection chamber is positioned approximately adjacent to the impermeable flexible overlay on the side of the impermeable flexible overlay opposite the wound and the collection chamber attachment means is a rigid or semi-rigid connecting member positioned between the collection chamber and the impermeable flexible overlay. In these embodiments, the connecting member has a port therein that extends between the collection chamber and the flexible overlay. In embodiments where the flexible overlay is approximately elongated-conically shaped, the collection chamber and the collection chamber attachment means may be positioned approximately at the apex of the flexible overlay on the side of the impermeable flexible overlay opposite the wound. In some embodiments, the collection chamber may be approximately cylindrical in shape. In other embodiments, the collection chamber attachment means may be further comprised of a flow control means, which is described in more detail below, operably positioned between the collection chamber and the flexible overlay. In these embodiments, the flow control means permit the fluid to flow from the volume under the flexible overlay in the area of the wound into the collection chamber, but not in the opposite direction. In some of these embodiments, the flow control means may be comprised of a valve. In some of these embodiments, the valve may be comprised of a flapper-type valve. In yet other embodiments, the collection chamber is positioned approximately adjacent to the impermeable flexible overlay on the side of the impermeable flexible overlay opposite the wound and the collection chamber attachment means is comprised of a membrane. In these embodiments, the membrane acts as a barrier separating the collection chamber and the impermeable flexible overlay, so that the membrane acts as a portion of the surface of the collection chamber and a portion of the surface of the impermeable flexible overlay. In addition, the membrane has at least one port therein so that the volume within the collection chamber is in fluid communication with the volume under the impermeable flexible overlay in the area of the wound. In embodiments where the impermeable flexible overlay has an approximately conical shape or approximately elongated conical shape, the impermeable flexible overlay may have a base end opening and a top end opening opposite the base end opening. In these embodiments, the base end opening may have an either approximately circular shape or approximately elliptical shape sized to be placed over and enclose the area of the wound to be treated. The top end opening may have either an approximately circular shape or approximately elliptical shape. In these embodiments, the membrane is sized to be of the same shape and size as the top end opening and the membrane is positioned so that it is attached to the entire perimeter of the top end opening and covers the entire top end opening. In some embodiments, the collection chamber may have an approximately conical shape or approximately elongated conical shape with a chamber bottom end opening and a reduced pressure supply port positioned at the apex of the collection chamber opposite the chamber bottom end opening. In various embodiments, the chamber bottom end opening may have an either approximately circular shape or approximately elliptical shape adapted to be of approximately the same size and shape as the top end opening of the impermeable flexible overlay. In some of these embodiments, the perimeter of the chamber bottom end opening is attached to the membrane in a manner so that the collection chamber is airtight, except for the port in the membrane and the reduced pressure supply port. The reduced pressure supply port operably connects the reduced pressure supply means to the collection chamber. In some embodiments, the collection chamber attachment means is further comprised of flow control means operably connected with the at least one port, wherein the flow control means permits fluid aspirated from the wound to flow from the volume under the impermeable flexible overlay in the area of the wound through the at least one port to the collection chamber, but not in the opposite direction. In some of these embodiments, the flow control means is comprised of a valve. Preferably, this valve is comprised of a flapper-type valve.

In a second aspect of the second version of the present invention, the wound treatment appliance is comprised of a wound treatment device and a vacuum system, which is further comprised of a reduced pressure supply source that provides a supply of reduced pressure and reduced pressure supply means to operably connect the wound treatment device to the reduced pressure supply source. In various embodiments of this second aspect of the second version of the invention, except as described below, the wound treatment device and the reduced pressure supply means may generally have substantially the same structure, features, characteristics and operations as the appliance described above in connection with the first aspect of the second version of the invention. In these embodiments, the reduced pressure supply means operably connect the wound treatment device to the reduced pressure supply source so that the volume within the collection chamber and under the wound treatment device in the area of the wound is supplied with reduced pressure by the reduced pressure supply source.

In some embodiments of this second aspect of the second version of the invention, the reduced pressure supply source is comprised of a vacuum pump. In some of these embodiments, the reduced pressure supply source further comprises a control system for the vacuum pump, wherein the control system controls the operation of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms aspirated from the wound or fluids aspirated from the wound or both. In yet other embodiments, the vacuum pump is comprised of a portable vacuum pump. In still other embodiments, the reduced pressure supply means is comprised of flexible tubing. In other embodiments of this second aspect of the second version of the invention, the reduced pressure under the flexible overlay in the area of the wound is in the range from approximately 20 mm of Hg below atmospheric pressure to approximately 125 mm of Hg below atmospheric pressure. In yet other embodiments, the reduced pressure is applied in a cyclic nature, the cyclic nature providing alternating time periods of application of reduced pressure and without application of reduced pressure. In some embodiments of this second aspect of the second version of the invention, the wound treatment appliance further comprises tissue protection means, which are described in more detail below, to protect and strengthen the body tissue that is adjacent to the flexible overlay at the wound site. In some of these embodiments, the tissue protection means is a hydrocolloid material. In still other embodiments, wound packing means, which are described in more detail herein, are positioned between the wound treatment device and the portion of the wound to be treated.

A third aspect of the second version of the present invention discloses a method of treating a wound on a body. In one embodiment of this third aspect of the second version of the invention, the method comprises the following steps. First, a wound treatment device is positioned on the body over the area of the wound to be treated, wherein the wound treatment device is comprised of an impermeable flexible overlay, a collection chamber, and collection chamber attachment means, which are described in more detail below. In this embodiment, the flexible overlay is sized to be placed over and enclose the area of the wound to be treated and adapted to maintain reduced pressure in the area of the wound to be treated. In addition, in this embodiment, the collection chamber receives and holds fluid aspirated from the wound and the collection chamber attachment means, which is described in more detail below, operably attaches the collection chamber to the impermeable flexible overlay in a manner so that reduced pressure and the fluid are permitted to flow between the collection chamber and the impermeable flexible overlay. Second, the collection chamber is operably connected with a vacuum system for producing reduced pressure in the volume within the collection chamber and in the volume under the flexible overlay in the area of the wound to be treated. Third, the flexible overlay is collapsed in the approximate direction of the wound when reduced pressure is supplied to the volume under the flexible overlay in the area of the wound so that an approximately hermetic seal (described in more detail herein) is formed between the impermeable flexible overlay and the body in the area of the wound. Fourth, reduced pressure is maintained until the area of the wound being treated has progressed toward a selected stage of healing. In other embodiments of this third aspect of the first version of the invention, the method further comprises the step of placing tissue protection means on the tissue of the body that is to be approximately adjacent to the impermeable flexible overlay, such step being performed prior to positioning the impermeable flexible overlay over the area of the wound to be treated. The tissue protection means, which is described in more detail below, protects and strengthens the tissue of the body adjacent to the flexible overlay at the wound site. In yet other embodiments of this third aspect of the first version of the invention, the method further comprises the step of placing wound packing means (described in more detail herein) between the wound and the impermeable flexible overlay in the area of the wound to be treated, such step being performed prior to positioning the impermeable flexible overlay over the area of the wound to be treated. In still other embodiments of this third aspect of the first version of the invention, the reduced pressure under the impermeable overlay in the area of the wound is in the range from approximately 20 mm of Hg below atmospheric pressure to approximately 125 mm of Hg below atmospheric pressure. In still other embodiments of this third aspect of the first version of the invention, the reduced pressure is applied in a cyclic nature, the cyclic nature providing alternating time periods of application of reduced pressure and without application of reduced pressure.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which.

DETAILED DESCRIPTION OF THE PREFERRED EMBODIMENTS

Figure 1A:
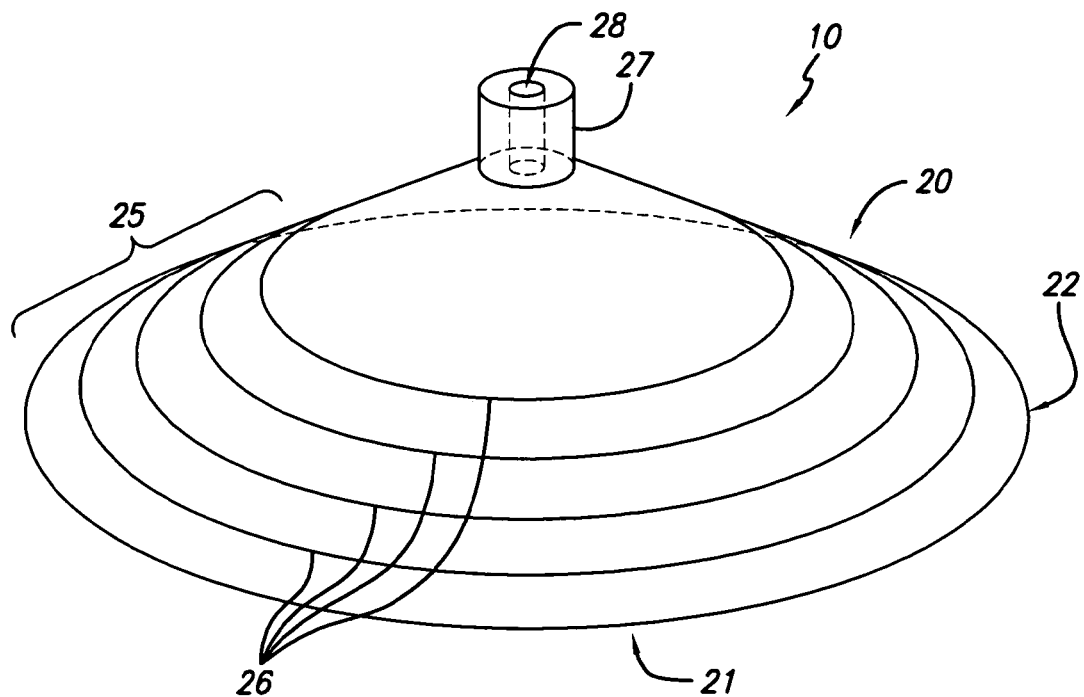
FIG. 1A is a perspective view of an embodiment of an impermeable flexible overlay of a wound treatment appliance of a first version of the present invention, as viewed from the side of and above the flexible overlay comprising the wound treatment appliance (as the flexible overlay would be oriented when placed on the body of a patient)
Figure 1B:
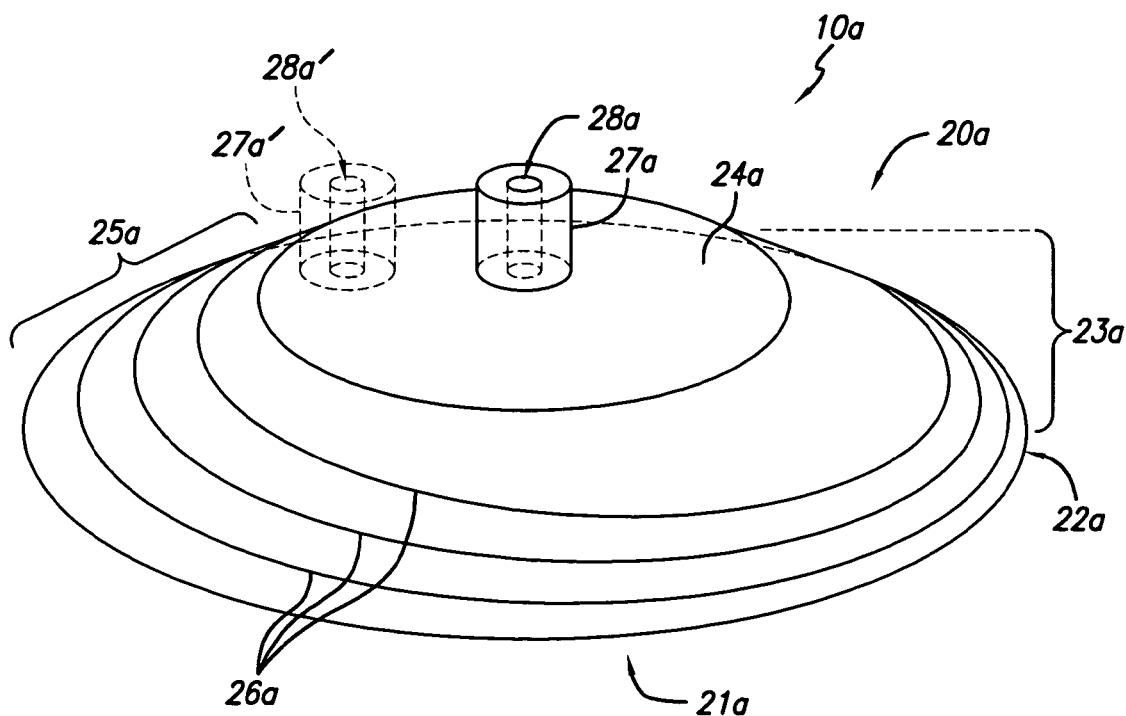
FIG. 1B is a perspective view of another embodiment of an impermeable flexible overlay of a wound treatment appliance of the first version of the present invention, as viewed from the side of and above the flexible overlay comprising the wound treatment appliance (as the flexible overlay would be oriented when placed on the body of a patient)
Figure 1C:
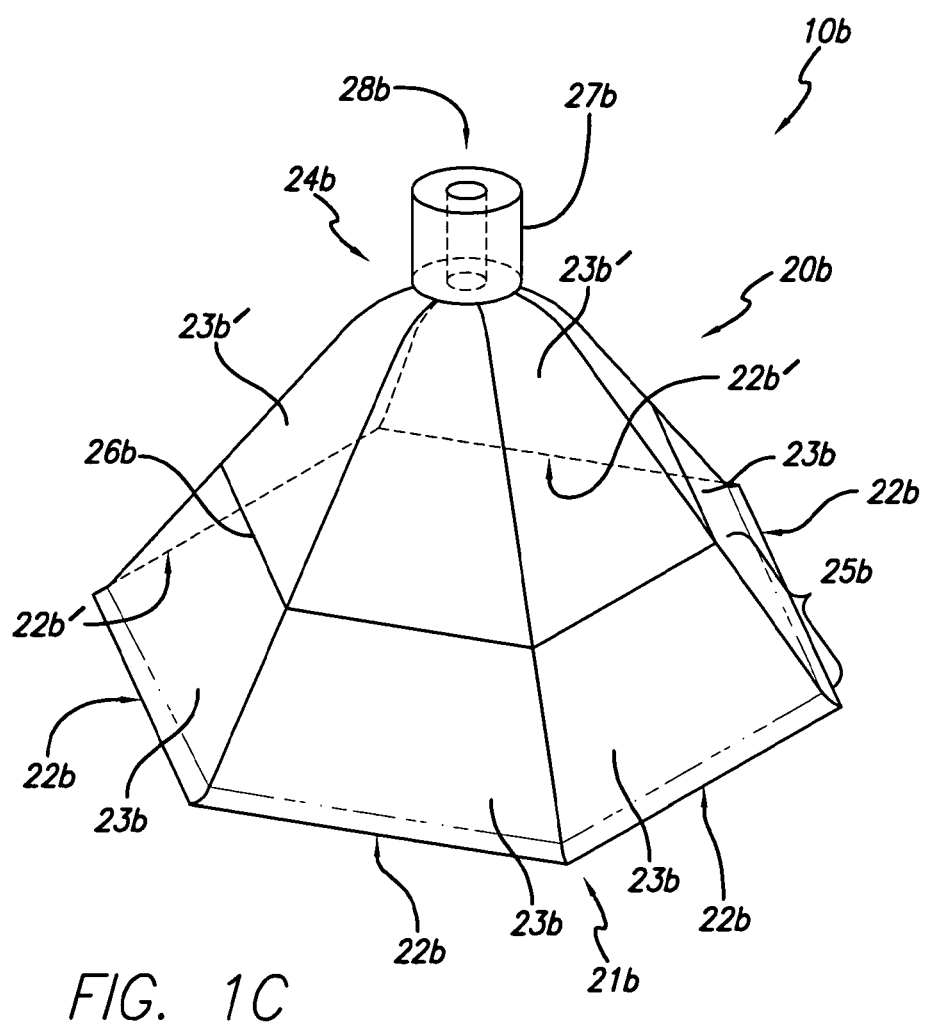
FIG. 1C is a perspective view of another embodiment of an impermeable flexible overlay of a wound treatment appliance of the first version of the present invention, as viewed from the side of and above the flexible overlay comprising the wound treatment appliance (as the flexible overlay would be oriented when placed on the body of a patient)
Figure 1D:
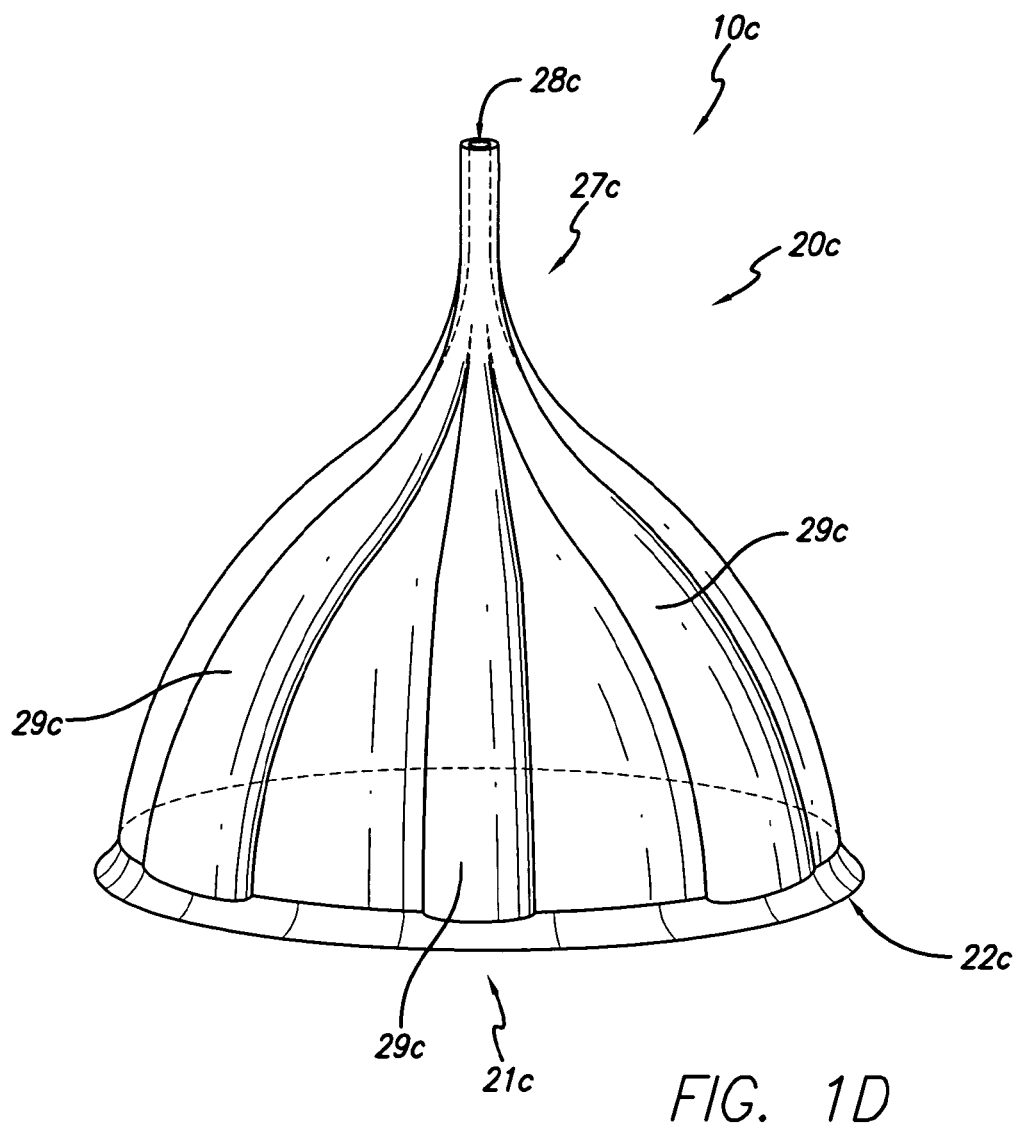
FIG. 1D is a perspective view of another embodiment of an impermeable flexible overlay of a wound treatment appliance of the first version of the present invention, as viewed from the side of and above the flexible overlay comprising the wound treatment appliance (as the flexible overlay would be oriented when placed on the body of a patient)

In accordance with the present invention, a wound treatment appliance is provided for treating all or a portion of a wound by applying reduced pressure (i.e., pressure that is below ambient atmospheric pressure) to the portion of the wound to be treated in a controlled manner for a selected time period in a manner that overcomes the disadvantages of currently existing apparatus. One embodiment of a first aspect of a first version of the invention is a wound treatment appliance 10 that is comprised of the fluid impermeable flexible overlay 20 illustrated in FIG. 1A and reduced pressure supply means, which are described in more detail below. In this embodiment, the flexible overlay 20 has an approximately elongated conical shape, having an opening 21 with an opening perimeter 22 adjacent to the opening 21 (at the base of the elongated conical shape) that is approximately elliptical in shape. The flexible overlay 20 illustrated in FIG. 1A is in its natural shape, as it exists prior to being applied to a patient for treatment of all or a portion of a wound. In other embodiments, the flexible overlay 20 may have other shapes. For example, the flexible overlay 20 may be approximately conical in shape, rather than the approximately elongated conical shape illustrated in FIG. 1A. As another example, as illustrated in FIG. 1B, only the bottom portion 23a of the flexible overlay 20a may have an approximately elongated conical shape. In this embodiment, and in the same manner as illustrated in FIG. 1A, the bottom portion 23a has an opening 21a with an opening perimeter 22a adjacent to the opening 21a (at the base of the elongated conical shape) that is approximately elliptical in shape. In the embodiment of the flexible overlay illustrated in FIG. 1B, the top portion 24a is flatter than the comparable portion of the flexible overlay 20 in the embodiment illustrated in FIG. 1A. In other embodiments, the top portion 24*a* of the flexible overlay 20*a* may have almost any shape that is adaptable to a bottom portion 23*a* having an approximately elongated conical shape. In addition, in yet other embodiments of this first aspect of the first version of the invention, the bottom portion 23*a* of the flexible overlay 20*a* may be in the approximate shape of a cone, rather than the elongated conical shape illustrated in FIG. 1B. In yet another embodiment, as illustrated in FIG. 1C, the flexible overlay 20*b* is comprised of six cover portions 23*b*, 23*b*', where the cover portions 23*b* are viewable in FIG. 1C and the cover portions 23*b*' are illustrated by phantom lines. In this embodiment, each of such cover portions 23*b*, 23*b*' is approximately triangular in shape, and one point of each of the at least three cover portions 23*b*, 23*b*' is joined to form an apex 24*b* of the impermeable flexible overlay 20*b*. One side of each cover portion 23*b*, 23*b*' adjacent to the apex 24*b* is joined to an adjacent side of another of such cover portions 23*b*, 23*b*' so that the bases 22*b*, 22*b*' of the cover portions 23*b*, 23*b*', respectively, form an opening 21*b* sized to be placed over and enclose the area of the wound to be treated. In other embodiments, the flexible overlay 20*b* may have a different number of cover portions 23*b*, 23*b*'. Preferably, in these embodiments, there are at least three cover portions 23*b*, 23*b*'. In addition, in yet other embodiments, the flexible overlay 20*b* may have cover portions 23*b*, 23*b*' having a different shape, such as trapezoidal or parabolic. Another embodiment of the first aspect of the first version of the present invention is illustrated in FIG. 1D. In this embodiment, the overlay 20*c* is approximately cup-shaped with an approximately circular opening 21*c*, which has an opening perimeter 22*c* adjacent to the opening 21*c*. The overlay 20*c* of this embodiment also has a plurality of channels 29*c* disposed in the surface thereof as suction assist means, which are described in more detail below. In still other embodiments, the flexible overlay 20, 20*a*, 20*b*, 20*c* may be of almost any shape that may be adaptable for treating all or a portion of a wound, as long as the flexible overlay 20, 20*a*, 20*b*, 20*c* is flexible, as described in more detail below, and the interior surface of the flexible overlay 20, 20*a*, 20*b*, 20*c* is adapted to make an approximately hermetic seal with the body of the patient at the site of the wound, as described in more detail below. For example, and as clarification, the flexible overlay 20, 20*a*, 20*b*, 20*c* or portions thereof may have an approximately tetrahedral, hexahedral, polyhedral, spherical, spheroidal, arcuate, or other shape or combination of all such shapes. Referring again to FIG. 1A as an example, in some embodiments of this first aspect of the first version of the invention, the interior surface of the flexible overlay 20 is adapted to make an approximately hermetic seal with the body of the patient at the site of the wound by having a surface area larger than the surface area of the portion of the body of the patient covered by the flexible overlay 20, as described in more detail below.

The preferred shape and size of the flexible overlay 20, 20*a*, 20*b*, 20*c* is dependent upon the size of the portion of the wound to be treated, the shape and contour of the portion of the body that is to be covered by the flexible overlay 20, 20*a*, 20*b*, 20*c* at the site of the wound, the magnitude of the reduced pressure to be maintained under the flexible overlay 20, 20*a*, 20*b*, 20*c*. More preferred, as illustrated in FIG. 1B, the flexible overlay 20*a* has an approximately elongated conically shaped bottom portion 23*a*. Most preferred, as illustrated in FIG. 1A, the flexible overlay 20 is shaped approximately as an elongated cone. The preferred thickness of the portion 25, 25*a*, 25*b*, 20*c* of the flexible overlay 20, 20*a*, 20*b*, 20*c* adjacent to the open end 21, 21*a*, 21*b*, 20*c* of the flexible overlay 20, 20*a*, 20*b*, 20*c* is dependent upon the size and shape of the flexible overlay 20, 20*a*, 20*b*, 20*c*, the shape and contour of the portion of the body that is to be covered by the flexible overlay 20, 20*a*, 20*b*, 20*c* at the site of the wound, the magnitude of the reduced pressure to be maintained under the flexible overlay 20, 20*a*, 20*b*, 20*c*, and other factors, such as the depth of the wound and the amount of the desired collapse of the flexible overlay 20, 20*a*, 20*b*, 20*c*. For example, in the embodiment illustrated in FIG. 1A, for a flexible overlay 20 constructed of silicone and having an approximately elongated conical shape with an opening 21 having a major diameter of approximately 7 inches and a minor diameter of approximately 4 inches, the preferred thickness of the portion 25 of the flexible overlay 20 adjacent to the open end 21 of the flexible overlay 20 is in the range from ⅟32 inches to ³⁄32 inches. More preferred in this embodiment, the thickness of the portion 25 of the flexible overlay 20 adjacent to the open end 21 of the flexible overlay 20 is approximately ⅟16 inches. It is to be noted that in other embodiments the thickness of the flexible overlay, 20, including the portion 25 of the flexible overlay 20 adjacent to the open end 21 of the flexible overlay 20, may vary from location to location on the flexible overlay 20.

In the embodiment of the flexible overlay 20 illustrated in FIG. 1A, the flexible overlay 20 has a series of raised beads 26 on the outside surface of the flexible overlay 20. In this embodiment, the raised beads 26 are generally parallel to the perimeter 22 of the opening 21 of the flexible overlay 20. The same is also true of the raised bead 26*b* of the flexible overlay 20*b* of the embodiment illustrated in FIG. 1C. In other embodiments, such as that illustrated in FIG. 1B, the raised beads 26*a* may have a different orientation. In still other embodiments, the raised beads 26, 26*a*, 26*b* may be in almost any orientation desired by the user of the wound treatment appliance 10, 10*a*, 10*b*. In various embodiments of this first aspect of the first version of the invention, as illustrated in FIG. 1A, the raised beads 26 may provide a guide for the user administering the reduced pressure treatment to cut away a portion of the flexible overlay 20, so that the perimeter 22 of the opening 21 of the flexible overlay 20 is smaller than it was originally. For example, by cutting along the parallel raised beads 26 of the flexible overlay 20 of FIG. 1A, the size of the opening 21 of the flexible overlay 20 can be made smaller while the shape of the perimeter 22 remains approximately the same. It is to noted, however, that in various embodiments of this first aspect of the first version of the invention, as described in more detail below, the flexible overlay 20 may be cut into different shapes in order to adapt the flexible overlay 20 for use with different shapes and contours of the surface of the body at the site of the wound.

In other embodiments of this first aspect of the present invention, as illustrated in FIG. 1D, the flexible overlay 20*c* may be further comprised of suction assist means to assist in the application of reduced pressure to the portion of the wound to be treated, as well as removal of exudate from the wound. For example, in the illustrated embodiment, the overlay 20*c* has a plurality of channels 29*c* disposed in the surface thereof. The channels 29*c* may generally provide a conduit for reduced pressure to reach the various portions of the wound to be treated. In addition, exudate aspirated from the various portions of the wound to be treated may flow along the channels 29*c* to the reduced pressure supply means (not illustrated), where the exudate may be removed from the flexible overlay 20*c* by means of the reduced pressure supply means cooperating with the reduced pressure supply source, as described in more detail below. In some of these embodiments, the channels 29c may be operably connected to the reduced pressure supply means through a port 27c, as described in more detail below. In the illustrated embodiment, there are three continuous channels 29c recessed into the surface of the overlay 20c, which are joined together near the apex of the flexible overlay 20c at the port 27c. In other embodiments, there may be more or fewer channels 29c. For example, in other embodiments, there may be fewer channels 29c and the channels 29c may be of the same size or of a different size. In yet other embodiments, there may be many channels 29c, in which case the channels 29c may generally be of a smaller size. In addition, the channels 29c may be disposed in other positions relative to the flexible overlay 20c. For example, the channels 29c may be located at different locations on the flexible overlay 20c and may have a different orientation, such as being curved in a "corkscrew" pattern or crossed in a "checkerboard" pattern, rather than being oriented as illustrated in FIG. 1D. In still other embodiments, the channels 29c, as suction assist means, may have a different structure and form. For example, the channels 29c may be in the form of tubes positioned within the volume of the flexible overlay 20c, wherein the tubes have one or more perforations so that the channels 29c are in fluid communication with the volume under the flexible overlay 20c in the area of the wound to be treated. As another example, the channels 29c may have stiffening members, such as raised beads ("ribs") of material, so that the channels 29c have a greater stiffness than the remaining portions of the flexible overlay 20c. In other embodiments, the channels 29c, as suction assist means, may be in the form of portions that are raised above the surface of the flexible overlay 20c. Such raised portions may appear as "dimples" when viewed from above the flexible overlay 20c. The channels 29c, as suction assist means, may also be of almost any size, shape and pattern to accomplish their intended purpose. The preferred size, shape and pattern are dependent upon the size and shape of the flexible overlay 20c, the type of wound to be treated, the level of reduced pressure to be used in the treatment, the amount of exudate anticipated, the type of reduced pressure supply means utilized, and the individual preference of the user of the appliance 10c. Where utilized, channels 29c may be molded or cut into the surface of the flexible overlay 20c or, if in the shape of tubes, may be molded as a part of the surface of the flexible overlay 20c or may be welded or fused to the surface of the flexible overlay 20c. It is to be noted that the various embodiments of the flexible overlays 20, 20a, 20b illustrated and described above in connection with FIG. 1A, FIG. 1B, and FIG. 1C, respectively, may each also comprise suction assist means, and therefore may also comprise any of the various embodiments of the channels 29c illustrated and described above in connection with FIG. 1D.

In the various embodiments of this first aspect of the first version of the invention, the flexible overlay 20, 20a, 20b, 20c may be comprised of almost any medical grade flexible material that is currently known in the art or that may be developed in the art in the future, as long as such material is fluid-impermeable, suitable for purposes of wound treatment (e.g., can be sterilized and does not absorb significant amounts of wound exudate), and is capable of forming an approximately hermetic seal with the surface of the body at the site of the wound, as described in more detail below. For example, the flexible overlay 20, 20a, 20b, 20c may be comprised of rubber (including neoprene), and flexible polymer materials, such as silicone, silicone blends, silicone substitutes, polyester, vinyl, polyimide, polyethylene napthalate, polycarbonates, polyester-polycarbonate blends, or a similar polymer, or combinations of all such materials. Preferably, the flexible overlay 20, 20a, 20b, 20c is comprised of silicone. Although the raised beads 26, 26a, 26b may be constructed of a material different from the material comprising the remainder of the flexible overlay 20, 20a, 20b in various embodiments of the invention, the raised beads 26, 26a, 26b are preferably constructed from the same material comprising the remainder of the flexible overlay 20, 20a, 20b. In other embodiments, the raised beads 26, 26a, 26b may be placed on the flexible overlay 20, 20a, 20b by means of a mark, such as indelible ink, on the surface of the flexible overlay 20, 20a, 20b. In some embodiments, the channels 29c (and all other suction assist means) may be constructed of a material different from the material comprising the remainder of the flexible overlay 20c. For example, one or more of the channels 29c may be constructed of a slightly more rigid material than the remainder of the flexible overlay 20c so that such channel 29c or channels 29c better retain their shape. In other embodiments, the channels 29c may be constructed of the same material comprising the remainder of the flexible overlay 20c, but the channels 29c may have a different thickness than the remainder of the flexible overlay 29c. For example, one or more of the channels 29c may be slightly thicker than the remainder of the flexible overlay 20c so that such channel 29c or channels 29c better retain their shape. In still other embodiments, the channels 29c may be constructed of the same material comprising, and have the same thickness as, the remainder of the flexible overlay 20c. Preferably, the channels 29c are constructed of the same material as, but have a slightly greater thickness than, the remaining portions of the flexible overlay 20c. It is to be noted that in various embodiments of this first aspect of the first version of the invention, the flexible overlay 20, 20a, 20b, 20c may be constructed in whole or in part of gas-permeable materials, allowing limited amounts of oxygen to penetrate the flexible overlay 20, 20a, 20b, 20c so that the area of the wound under the flexible overlay 20, 20a, 20b, 20c can "breathe." It is also to be noted that all portions of the flexible overlay 20, 20a, 20b, 20c are preferably constructed of one type of polymer material, such as silicone. The flexible overlay 20, 20a, 20b, 20c may be constructed using any suitable means currently known in the art or that may be developed in the art in the future. For example, a flexible overlay 20, 20a, 20b, 20c constructed of silicone may be manufactured by means of injection molding. As another example, where the channels 29c are constructed of a different material from the remainder of the flexible overlay 20c, the channels 29c may be welded or fused to the remaining portions of the flexible overlay 20c.

In the embodiments of the flexible overlay 20, 20a, 20b, 20c illustrated in FIG. 1A, FIG. 1B, FIG. 1C, and FIG. 1D, respectively, each of the flexible overlays 20, 20a, 20b, 20c further comprises a port 27, 27a, 27b, 27c adapted to receive a reduced pressure supply means to supply reduced pressure to the area of the wound under the flexible overlay 20, 20a, 20b, 20c. Although the port 27 is positioned at approximately the apex of the elongated cone-shaped flexible overlay 20 in the embodiment illustrated in FIG. 1A, and the port 27b is positioned at approximately the apex 24b of the triangular-shaped cover portions 23b, 23b' in the embodiment illustrated in FIG. 1C, which is the preferred location, the port may be located at another location on the flexible overlay in other embodiments. In such embodiments, and referring to FIG. 1B as an example, the port 27a (and alternate port 27a') may be located at almost any location on the surface of the flexible overlay 20a as long as the port 27a, 27a' does not adversely affect the ability of the flexible overlay 20a to make an approximately hermetic seal with the surface of the body at the wound site, as described in more detail below. For example, the port 27a, 27a' may not be located too close to the perimeter 22a of the opening 21a of the flexible overlay 20a because the approximately hermetic seal with the surface of the body is typically formed at that location. In the embodiment of the flexible overlay 20a illustrated in FIG. 1B, the alternate port 27a' may preferably be located at any location on the top portion 24a of the flexible overlay 20a, and more preferably, the port 27a is located at the center of the top portion 24a of the flexible overlay 20a. Referring again to FIG. 1A as an example, although the port 27 may be constructed of a material different from the material comprising the remainder of the flexible overlay 20 in various embodiments of the invention, the port 27 is preferably constructed from the same material comprising the remainder of the flexible overlay 20. In the embodiments of the flexible overlay 20, 20a, 20b illustrated in FIG. 1A, FIG. 1B, and FIG. 1C, respectively, the ports 27, 27a, 27b are generally cylindrical in shape and are further comprised of an approximately cylindrical duct 28, 28a, 28b, respectively, that extends from the top of each of the ports 27, 27a, 27b, respectively, to the bottom of the ports 27, 27a, 27b, respectively. The ports 27, 27a, 27b of these embodiments are thus able to receive a vacuum system or reduced pressure supply means, which are described in more detail below, adapted to be connected to this shape of port 27, 27a, 27b, respectively, and channel 28, 28a, 28b, respectively. In other embodiments of this first aspect of the first aspect of the first version of the invention, the ports 27, 27a, 27b, 27c or the port ducts 28, 28a, 28b, respectively, or both may have different shapes and configurations as may be desired to adapt and connect the ports 27, 27a, 27b, respectively, and the port ducts 28, 28a, 28b, respectively, to the vacuum system or reduced pressure supply means, which are described in more detail below. For example, the port 27c of the flexible overlay 20c illustrated in FIG. 1D is formed as a single piece with the remainder of the flexible overlay 20c. In this example, the port 27c has a cylindrical duct 28c that extends through the port 27c and generally follows the contours of the channels 29c at its lower end.

Figure 2A:
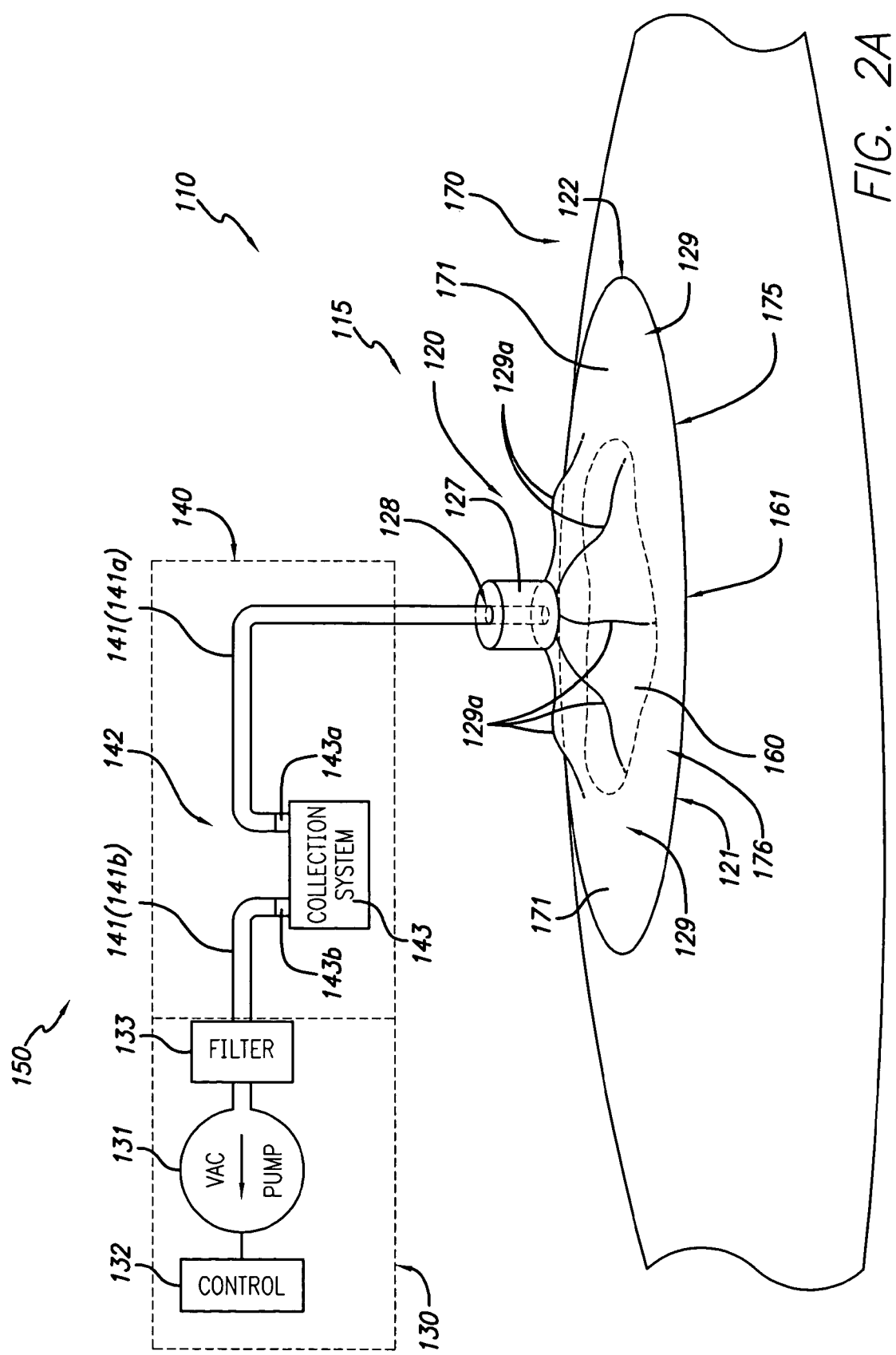
FIG. 2A is a view of an embodiment of a wound treatment appliance of the first version of the present invention, in which an embodiment of an impermeable flexible overlay, shown in perspective view from the side of and above the flexible overlay, covers a wound, and in which an embodiment of a vacuum system, depicted generally and shown in schematic elevation view, provides reduced pressure within the area under the flexible overlay.

An embodiment of a second aspect of the first version of the present invention is the wound treatment appliance 110 illustrated in FIG. 2A. In this embodiment, the wound treatment appliance 110 is comprised of a wound treatment device 115 and a vacuum system, generally designated 150, that is operably connected to, and provides a supply of reduced pressure to, the wound treatment device 115. Also in this embodiment, the wound treatment device 115 is comprised of a flexible overlay 120. In addition, in this embodiment, the vacuum system 150 is further comprised of a reduced pressure supply source, generally designated 130, which is illustrated schematically and described in more detail below, and reduced pressure supply means, generally designated 140, which are illustrated schematically and described in more detail below. Also in this embodiment, the reduced pressure supply means 140 are used to connect the reduced pressure supply source 130 to the flexible overlay 120 in a manner so that reduced pressure is supplied to the volume under the flexible overlay 120 in the area of the wound 160, as described in more detail below. In the embodiment of the second aspect of the first version of the invention illustrated in FIG. 2A, the flexible overlay 120 has substantially the same structure, features, characteristics and operation as the flexible overlay 20 described above and illustrated in connection with FIG. 1A. It is to be noted, however, that in other embodiments of this second aspect of the first version of the invention, the flexible overlay 120 may have substantially the same structure, features and characteristics as any embodiment of all of the flexible overlays 20, 20a, 20b, 20c of the first aspect of the first version of the invention described above and illustrated in connection with FIG. 1A, FIG. 1B, FIG. 1C, and FIG. 1D. FIG. 2A also illustrates an example of how the embodiment of the flexible overlay 20 illustrated in FIG. 1A may be used to provide reduced pressure treatment for a wound 160 on the body 170 of a patient. In this example, the flexible overlay 120 is placed over and encloses the entire wound 160, as described in more detail below. In other embodiments, the flexible overlay 120 need not enclose the entire wound 160.

In the embodiment illustrated in FIG. 2A, the reduced pressure supply source 130 of the vacuum system 150, which produces a source of reduced pressure or suction that is supplied to the flexible overlay 120, is comprised of a vacuum pump 131, a control device 132, and a filter 133. Although the preferred means of producing the reduced pressure or suction is a vacuum pump 131 in this embodiment, in other embodiments of this second aspect of the first version of the invention other means may be used, such as an outlet port of a centralized hospital vacuum system. In the illustrated embodiment, predetermined amounts of suction or reduced pressure are produced by the vacuum pump 131. The vacuum pump 131 is preferably controlled by a control device 132, such as a switch or a timer that may be set to provide cyclic on/off operation of the vacuum pump 131 according to user-selected intervals. Alternatively, the vacuum pump 131 may be operated continuously without the use of a cyclical timer. In addition, in some embodiments the control device 132 may provide for separate control of the level of reduced pressure applied to the wound 160 and the flow rate of fluid aspirated from the wound 160. In these embodiments, relatively low levels of reduced pressure may be maintained in the area of the wound 160 under the wound treatment device 115, while still providing for the removal of a relatively large volume of exudate from the wound 160. A filter 133, such as a micropore filter, is preferably attached to the inlet of the vacuum pump 131 to prevent potentially pathogenic microbes or aerosols from contaminating, and then being vented to atmosphere by, the vacuum pump 131. In other embodiments, the filter 133 may also be a hydrophobic filter that prevents any exudate from the wound from contaminating, and then being vented to atmosphere by, the vacuum pump 131. It is to be noted that in other embodiments of the invention, the reduced pressure supply source 130 may not have a filter 133 or a control 132 or any combination of the same.

In the embodiment of the second aspect of the first version of the invention illustrated in FIG. 2A, the reduced pressure supply means 140 of the vacuum system 150, which are used to connect the reduced pressure supply source 130 to the flexible overlay 120 so that reduced pressure is supplied to the volume under the flexible overlay 120 in the area of the wound 160 is comprised of at least one tubing member 141. In this embodiment, the at least one tubing member 141 is sufficiently flexible to permit movement of the at least one tubing member 141, but is sufficiently rigid to resist constriction when reduced pressure is supplied to the flexible overlay 120 or when the location of the wound 160 is such that the patient must sit or lie upon the at least one tubing member 141 or upon the wound treatment device 115. In the embodiment illustrated in FIG. 2A, the at least one tubing member 141 is connected to the flexible overlay 120 by inserting one end of the at least one tubing member 141 into the opening 128 of the port 127 of the flexible overlay 120. In this embodiment, the at least one tubing member is held in place in the opening 128 by means of an adhesive. It is to be noted that in other embodiments of this second aspect of the first version of the invention, the at least one tubing member 141 may be connected to the port 127 of the flexible overlay 120 using any suitable means currently known in the art or developed in the art in the future. Examples include variable descending diameter adapters (commonly referred to as "Christmas tree" adapters), luer lock fittings and adapters, clamps, and combinations of such means. Alternatively, the port 127 and the at least one tubing member 141 may be fabricated as a single piece, as is the case with the port 27c of the flexible overlay 20c, as illustrated and described above in connection with FIG. 1D. Similar means may be used to connect the other end of the at least one tubing member 141 to the vacuum pump 131 or other reduced pressure supply source 130 providing the reduced pressure.

Figure 2B:
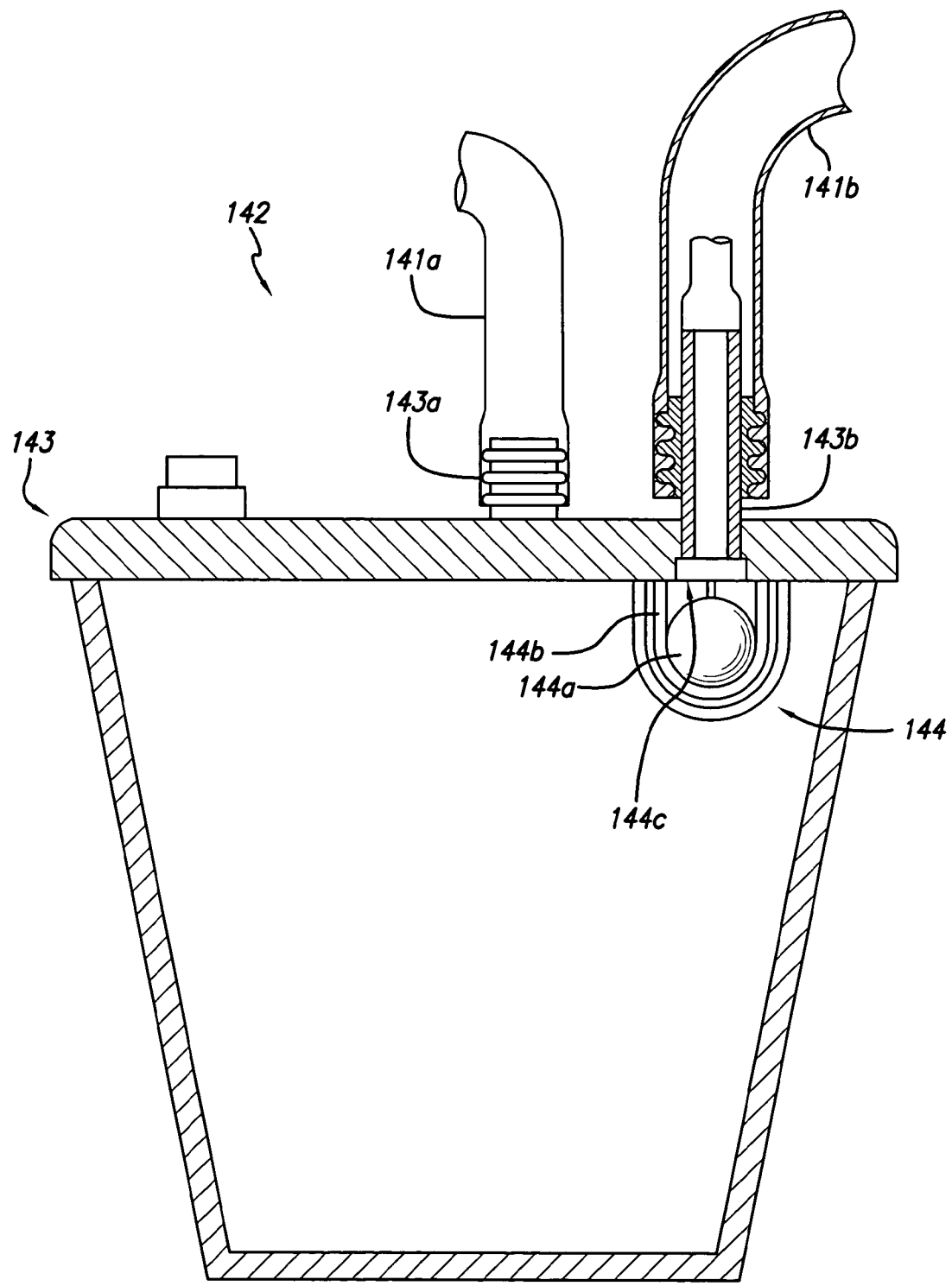
FIG. 2B is a sectional elevational detailed view of an embodiment of a collection container and the shutoff mechanism portion of the collection system of FIG. 2A.

In the embodiment illustrated in FIG. 2A, the reduced pressure supply means 140 further comprises a fluid collection system, generally designated 142, that is interconnected between the suction pump 131 and the flexible overlay 120 to remove and collect any exudate that may be aspirated from the wound 160 and collected by the flexible overlay 120. The flexible overlay 120 functions to actively draw fluid or exudate from the wound 160. Collection of exudate in a fluid collection system 142 intermediate the pump 131 and the flexible overlay 120 is desirable to prevent clogging of the pump 131. The fluid collection system 142 is comprised of a fluid-impermeable collection container 143 and a shutoff mechanism 144, which are described in more detail below in connection with FIG. 2B. The container 143 may be of any size and shape capable of intercepting and retaining a predetermined amount of exudate. Many examples of such containers are available in the relevant art. Referring to FIG. 2B, which is an enlarged elevational cross-sectional view of the preferred embodiment of the container 143, the container 143 includes a first port 143a at the top opening of the container 143 for sealed connection to tubing member 141a, where the other end of the tubing member 141a is connected to the flexible overlay 120. The first port 143a enables suction to be applied to the flexible overlay 120 through the tubing 141a and also enables exudate from the portion of the wound 160 covered by the flexible overlay 120 to be drained into the container 143. The container 143 provides a means for containing and temporarily storing the collected exudate. A second port 143b is also provided on the top of the container 143 to enable the application of suction from the vacuum pump 131. The second port 143b of the collection system 142 is connected to the vacuum pump 131 by tubing member 141b. The collection system 142 is sealed generally gas-tight to enable the suction pump 131 to supply suction to the flexible overlay 120 through the collection system 142.

The embodiment of the collection system 142 illustrated in FIG. 2B also includes a shutoff mechanism for halting or inhibiting the supply of the reduced pressure to the flexible overlay 120 in the event that the exudate aspirated from the wound 160 exceeds a predetermined quantity. Interrupting the application of suction to the flexible overlay 120 is desirable to prevent exsanguination in the unlikely event a blood vessel ruptures under the flexible overlay 120 during treatment. If, for example, a blood vessel ruptures in the vicinity of the wound 160, a shut-off mechanism would be useful to prevent the vacuum system 150 from aspirating any significant quantity of blood from the patient. In the preferred embodiment of the shutoff mechanism 144, as illustrated in FIG. 2B, the shutoff mechanism 144 is a float valve assembly in the form of a ball 144a which is held and suspended within a cage 144b positioned below a valve seat 144c disposed within the opening at the top of the container below the second port 143b that will float upon the exudate and will be lifted against the valve seat 144c as the container 143 fills with exudate. When the ball 144a is firmly seated against the valve seat 144c, the float valve blocks the second port 143b and thereby shuts off the source of suction from the vacuum system 150. In other embodiments of the container 143, other types of mechanisms may also be employed to detect the liquid level within the container 143 in order to arrest operation of the vacuum system 50. In addition, in various embodiments of this second version of the invention, the shutoff mechanism 144 may be comprised of any means that enables the vacuum system 150 to halt the supply of reduced pressure to the flexible overlay 120 at any time that the volume of exudate from the wound 160 exceeds a predetermined amount. Such means may include mechanical switches, electrical switches operably connected to the vacuum system controller 132, optical, thermal or weight sensors operably connected to the vacuum system controller 132, and any other means that are currently known in the relevant art or that may be developed in the art in the future.

In some embodiments of this second version of the invention, the wound treatment appliance 110 further comprises tissue protection means 175 to protect and strengthen the body tissue 171 that is adjacent to the flexible overlay 120 at the wound site 161. The tissue protection means 175 protects the tissue 171 by preventing abrasion and maceration of the tissue. Preferably, the tissue protection means 175 is a hydrocolloid material, such as COLOPAST Hydrocolloid 2655, anhydrous lanoline, or any combination of such hydrocolloid materials. More preferably, the tissue protection means 175 is COLOPAST Hydrocolloid 2655. The tissue protection means 175 may be applied to the body tissue 171 to be protected, or it may be applied to the surface of the flexible overlay 120 that is to be in contact with the body tissue 171, or both, prior to placing the flexible overlay 120 on the surface of the body 170 at the wound site 161. It is to be noted that application of the tissue protection means 175 to the body tissue 171 that is adjacent to the flexible overlay 120 at the wound site 161 may only entail application of the tissue protection means 175 to the portion of the body tissue 171 adjacent to the flexible overlay 120 that requires such protection.

FIG. 2A also illustrates an example of how the embodiment of the flexible overlay 20 illustrated in FIG. 1A (which is flexible overlay 120 in FIG. 2A) may be used to provide reduced pressure treatment for a wound 160 on the body 170 of a patient. In this example, the flexible overlay 120 is removed from an aseptic package in which it is stored. The flexible overlay 120 is then placed over and encloses the portion of the wound 160 to be treated, which is the entire wound 160 in this example. The flexible overlay 120 is also connected to the vacuum system 150 by means of the port 127 on the flexible overlay 120 either before, after or during the placement of the flexible overlay 120 over the wound 160. Where it is deemed necessary by the user of the wound treatment appliance 110, tissue protection means 175, as described above, may be placed on a portion of the flexible overlay 120, on the body tissue 171 to be protected, or both, prior to placing the flexible overlay 120 over the wound 160. In the example illustrated in FIG. 2A, the interior surface portions 129 of the flexible overlay 120 positioned around and adjacent to the perimeter 122 of the opening 121 of the flexible overlay 120 are at (or can be deformed to be at) a relatively acute angle relative to the surrounding surface of the body 170. Such deformation may be caused by the user of the wound treatment appliance 110 exerting mild pressure on the portions 129 of the flexible overlay 120 positioned around and adjacent to the perimeter 122 of the opening 121 of the flexible overlay 120 so that they are in contact with the surface of the body 170 surrounding the wound 160. Reduced pressure is then supplied to the flexible overlay 120 by the vacuum system 150. When reduced pressure is applied to the volume under the flexible overlay 120 in the area of the wound 160, the flexible overlay 120 is drawn downward by the reduced pressure, collapsing the flexible overlay 120 in the approximate direction of the wound 160. As the flexible overlay 120 collapses, the portions 129 of the flexible overlay 120 adjacent to the perimeter 122 of the Opening 121 of the flexible overlay 120 are drawn tightly against the surface of the body 170 surrounding the wound 160, thus forming an approximately hermetic seal between the portions 129 of the flexible overlay 120 adjacent to the perimeter 122 of the opening 121 of the flexible overlay 120 and the portion of the body 170 adjacent to such portions 129. References to an "approximately hermetic seal" herein refer generally to a seal that may be made gas-tight and liquid-tight for purposes of the reduced pressure treatment of the wound 160. It is to be noted that this seal need not be entirely gas-tight and liquid-tight. For example, the approximately hermetic seal may allow for a relatively small degree of leakage, so that outside air may enter the volume under the flexible overlay 120 in the area of the wound 160, as long as the degree of leakage is small enough so that the vacuum system 150 can maintain the desired degree of reduced pressure in the volume under the flexible overlay 120 in the area of the wound 160. As another example, the approximately hermetic seal formed by the collapsing flexible overlay 120 may not be solely capable of maintaining the reduced pressure in the volume under the flexible overlay 120 in the area of the wound 160. This may be the case if the shape of the body 170 at the site of the wound 160 does not allow for such a seal. In other instances, as may be the case with the flexible overlay 20c illustrated and described above in connection with FIG. 1D, the perimeter 22c adjacent to the opening 21c may not have a relatively acute angle relative to the surrounding tissue, so that additional means is required to make an approximately hermetic seal. In these cases, it may be necessary to provide supplemental sealing means, which are used to provide a seal between the portions of the flexible overlay 120 and the body 170 where the approximately hermetic seal is not adequate to permit reduced pressure to be maintained in the volume under the flexible overlay 120 in the area of the wound 160. For example, in the illustrated embodiment, the supplemental sealing means 176 may be an adhesive applied to a portion of the impermeable overlay 120 or a portion of the body 170 in a manner similar to the application of the tissue protection means 175 described above. In other embodiments, the supplemental sealing means 176 may be comprised of almost any suitable means to provide an adequate seal. For example, the supplemental sealing means 176 may be comprised of an adhesive, an adhesive tape, a stretch fabric that covers the wound treatment device 115 and is wrapped around a portion of the body 170 of the patient in the area of the wound 160, lanoline, or any combination of such means. It is also to be noted that in this embodiment at least one fold 129a forms in the surface of the flexible overlay 120 when it collapses, so that exudate aspirated by the wound 160 flows along the at least one fold 129a to the port 127, where the exudate is removed from the flexible overlay 120 by means of the reduced pressure supply means 140 cooperating with the reduced pressure supply source 130. Thus, in the preferred embodiments, the impermeable overlay 120 is constructed of a material, and has a size, shape and thickness, that permits the flexible overlay 120 to collapse in the direction of the wound 160 and form an approximately hermetic seal with the body 170 when reduced pressure is applied to the volume under the flexible overlay 120 in the area of the wound 160, while still being rigid enough to support the approximately hermetic seal with the body 170 and to support the at least one fold 129a. In embodiments of the overlay 120 comprising suction assist means, such as the channels 29c of the flexible overlay 20c illustrated and described above in connection with FIG. 1D, exudate from the wound 160 may also flow along such channels to the port 127. It is also to be noted that the volume under the flexible overlay 120 in the area of the wound 160 may be minimal while the flexible overlay 120 is in its collapsed state over the wound 160. In the preferred embodiments of this second aspect of the first version of the invention, the reduced pressure maintained in the volume under the flexible overlay 120 in the area of the wound 160 is in the range from approximately 20 mm of Hg below atmospheric pressure to approximately 125 mm of Hg below atmospheric pressure. In yet other embodiments, the reduced pressure is applied to the flexible overlay 120 in a cyclic nature, the cyclic nature providing alternating time periods of application of reduced pressure and non-application of reduced pressure. In all of these embodiments, the reduced pressure is maintained in the volume under the flexible overlay 120 in the area of the wound 160 until the wound 160 has progressed toward a selected stage of healing.

Figure 3:
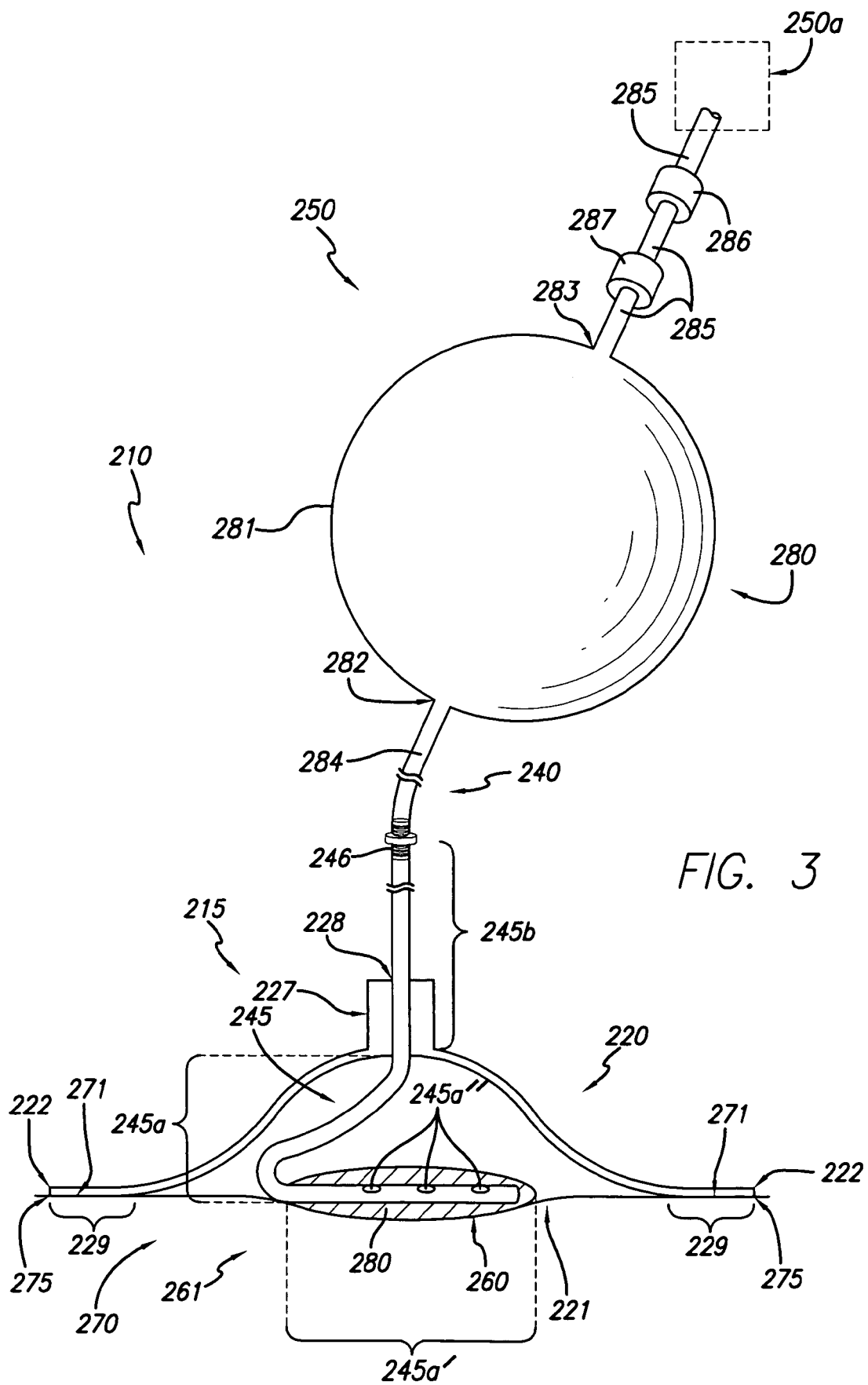
FIG. 3 is a view of a wound treatment appliance of the first version of the present invention, in which an embodiment of an impermeable flexible overlay, shown in cross-sectional elevational view from the side of the flexible overlay, covers a wound and wound packing means, and in which an embodiment of a vacuum system, shown in elevational view, provides reduced pressure within the area under the flexible overlay.

An embodiment of a third aspect of the first version of the invention is the wound treatment appliance 210 illustrated in FIG. 3. In this embodiment, the wound treatment appliance 210 is comprised of a wound treatment device 215 and a vacuum system, generally designated 250, that is operably connected to, and provides a supply of reduced pressure to, the wound treatment device 215. In addition, in this embodiment, the vacuum system 250 is further comprised of a reduced pressure supply source, generally designated 280, which is described in more detail below, and reduced pressure supply means, generally designated 240, which are described in more detail below. Also in this embodiment, the wound treatment device 215 is further comprised of a flexible overlay 220, wound packing means 278, and a suction drain 245. In the embodiment of the third aspect of the first version of the invention illustrated in FIG. 3, the flexible overlay 220 has substantially the same structure, features, characteristics and operation as the flexible overlay 20 described above and illustrated in connection with FIG. 1A. It is to be noted, however, that in other embodiments of this third aspect of the first version of the invention, the flexible overlay 220 may have substantially the same structure, features, characteristics and operation as any embodiment of all of the flexible overlays 20, 20a, 20b, 20c of the first aspect of the first version of the invention described above and illustrated in connection with FIG. 1A, FIG. 1B, FIG. 1C, and FIG. 1D, respectively. In the embodiment illustrated in FIG. 3, the flexible overlay 220 is placed over and encloses the entire wound 260 and is illustrated in a state of partial collapse, with the portion 229 of the flexible overlay 220 adjacent to the opening 221 in the perimeter 222 of the flexible overlay 220 forming an approximately hermetic seal with the adjacent portions 271 of the body 270. It is to be noted that in various embodiments of this third aspect of the first version of the invention, the wound treatment appliance 210 may also be comprised of tissue protection means 275, which may be substantially the same as the tissue protection means 175 of the second aspect of the first version of the invention described above and illustrated in connection with FIG. 2A.

In the embodiment of the third aspect of the first version of the invention illustrated in FIG. 3, the wound treatment device 215 is further comprised of wound packing means 278, which is placed in the area of the wound 260 under the flexible overlay 220. In this embodiment, the flexible overlay 220 is placed over the area of the wound 260 to be treated and the wound packing means 278 when the flexible overlay 220 is positioned on the surface of the body 270 at the site of the wound 260. In some embodiments of this third aspect of the first version of the invention, the wound packing means 278 may be placed within the wound 260 to prevent overgrowth of the tissue in the area of the wound 260. For example, and preferably in these cases, the wound packing means 278 may comprised of absorbent dressings, antiseptic dressings, nonadherent dressings, water dressings, or combinations of such dressings. More preferably, the wound packing means 278 may be comprised of gauze or cotton or any combination of gauze and cotton. In still other embodiments of this third aspect of the first version of the invention, the wound packing means 278 may be comprised of an absorbable matrix adapted to encourage growth of the tissue in the area of the wound 260 into the matrix. In these embodiments, the absorbable matrix (as wound packing means 278) is constructed of an absorbable material that is absorbed into the epithelial and subcutaneous tissue in the wound 260 as the wound 260 heals. The matrix (as wound packing means 278) may vary in thickness and rigidity, and it may be desirable to use a spongy absorbable material for the patient's comfort if the patient must lie upon the wound treatment device 215 during treatment. The matrix (as wound packing means 278) may also be perforated and constructed in a sponge-type or foam-type structure to enhance gas flow and to reduce the weight of the matrix. Because of the absorbable nature of the absorbable matrix (as wound packing means 278), the matrix should require less frequent changing than other dressing types during the treatment process. In other circumstances, the matrix (as wound packing means 278) may not need to be changed at all during the treatment process. In some embodiments of this third aspect of the first version of the invention, the absorbable matrix (as wound packing means 278) may be comprised of collagens or other absorbable materials or combinations of all such materials. U.S. patent application Ser. No. 10/652,100, which was filed by the present inventor with the U.S. Patent and Trademark Office on Aug. 28, 2003, and is hereby incorporated by reference, also discloses various embodiments of an absorbable matrix that may be utilized with various embodiments of the third aspect of the first version of the present invention. It is to be noted, however, that wound packing means 278 may not be utilized in other embodiments of this third aspect of the first version of the invention.

In the embodiment of the third aspect of the first version of the invention illustrated in FIG. 3, the wound treatment device 215 is also comprised of a suction drain 245 and suction drain connection means, which are described in more detail below, to operably connect the reduced pressure supply means 240 to the suction drain 245 so that the suction drain 245 is in fluid communication with the reduced pressure supply means 240 and reduced pressure is supplied to the volume under the flexible overlay 220 in the area of the wound 260 by means of the suction drain 245. In this embodiment, the suction drain 245 is further comprised of a bottom drain portion 245a extending into the area of the wound 260 under the impermeable overlay 220 from a top drain portion 245b positioned within the port 227. In various embodiments, the top drain portion 245b may be permanently or removably attached to the interior surface of the opening 228 of the port 227 using any suitable means, such as an adhesive, or by the top drain portion 245b having a shape adapted so that all or a portion of it fits tightly against all or a portion of the interior surface of the opening 228 in the port 227. It is to be noted that the top drain portion 245b must be sufficiently sealed against the surface of the port 227 in a manner so that reduced pressure can be maintained in the volume under the impermeable overlay 220 in the area of the wound 260. In the embodiment illustrated in FIG. 3, the top drain portion 245b and the bottom drain portion 245a of the suction drain 245 are comprised of polymer tubing that is flexible enough to allow the tubing to easily bend, but rigid enough to prevent the tubing from collapsing during use. In other embodiments, portions of the top drain portion 245b and the bottom drain portion 245a of the suction drain 245 may be comprised of other materials, such as flexible or semi-rigid polymers, plastics, rubber, silicone, or combinations of such materials. In yet other embodiments, the suction drain 245 may have different cross-sectional shapes, such as elliptical, square, rectangular, pentagonal, hexagonal, or other shapes, as long as the suction drain 245 is adapted to provide an approximately hermetic seal with the port 227, as described in more detail above. In still other embodiments, the bottom drain portion 245a of the suction drain 245 may be further comprised of wound suction means that may be used to remove debris, exudate and other matter from the wound 260. In the embodiment illustrated in FIG. 3, the wound suction means is comprised of a distal end portion 245a' of the tubing comprising the bottom drain portion 245a having a plurality of perforations 245a" in the surface of the distal end portion 245a'. In other embodiments, the distal end portion 245a' of the bottom drain portion 245a may have almost any shape or combination of shapes (e.g., circular, elliptical, square, pentagonal, or hexagonal), including a shape different from the remaining portion of the bottom drain portion 245a, may be of almost any size relative to the remaining bottom drain portion 245a (e.g., may be longer or shorter than the remaining bottom drain portion 245a or have a cross-section smaller or larger than the remaining bottom drain portion 245a, or both), may have more or fewer perforations 245a", may have different sizes and shapes of perforations 245a", may extend along different portions of the bottom drain portion 245a, and may be constructed in whole or in part of materials that are not flexible. In embodiments that have a distal end portion 245a', the distal end portion 245a' may be attached to the remaining portion of the bottom drain portion 245a in almost any manner, as long as the remaining bottom drain portion 245a is in fluid communication with the wound suction means 245a'. Examples include an adhesive in some embodiments and a fastening collar in other embodiments. In still other embodiments, the distal end portion 245a' may be fused or welded to the remaining portion of the bottom drain portion 245a. In yet other embodiments, the distal end portion 245a' and the remaining portion of the bottom drain portion 245a may be fabricated as a single piece.

In some embodiments of this first version of the invention, as illustrated in FIG. 3, the top drain portion 245b may extend beyond the top of the port 227 into the area outside the volume of the flexible overlay 220. In some of these embodiments, as is also illustrated in FIG. 3, the suction drain connection means, which may be used to removably connect the reduced pressure supply means 240 to the top drain portion 245b of the suction drain 245 is a variable descending diameter adapter 246 (commonly referred to as a "Christmas tree" adapter) that is placed into the interior volume of the top drain portion 245b at its distal end. In other embodiments, the suction drain connection means may be clamps, fastening collars, or other fasteners or combinations thereof. In yet other embodiments, the top drain portion 245b may be fused or welded to the reduced pressure supply means 240. In still other embodiments, the top drain portion 245b and the portion of the reduced pressure supply means 240 adjacent to the top drain portion 245b may be fabricated as a single piece. In other embodiments, the top drain portion 245b may not extend beyond the top of the port 227 and the reduced pressure supply means 240 may connect directly to the port 227 using any suitable means, such as an adhesive, welding, fusing, clamps, collars or other fasteners, or any combination of such means.

In the embodiment of this third aspect of the first version of the invention illustrated in FIG. 3, the distal end portion 245a' of the suction drain 245 extends into the interior volume of the wound packing means 278. In this embodiment, the wound packing means 278 and the suction drain 245 may be fabricated by snaking the distal end portion 245a' of the suction drain 245 through an internal passageway in the wound packing means 278, such as by pulling the distal end portion 245a' of the suction drain 245 through the passageway using forceps. Alternatively, the wound packing means 278 and the suction drain 245 may be manufactured as a single piece in sterile conditions and then be stored in an aseptic package until ready for use. In other embodiments, the distal end portion 245a' of the suction drain 245 may be placed adjacent or close to the wound packing means 278 in the area of the wound 260. The preferred means of placement of the suction drain 245 relative to the wound packing means 278 is dependent upon the type of wound 260, the wound packing means 278, and the type of treatment desired. Referring to FIG. 3 as an example, it is therefore to be noted that in some embodiments of this third aspect of the first version of the invention, the wound treatment device 215 may utilize a suction drain 245 without utilizing wound packing means 278, while in other embodiments a suction drain 245 may be utilized with wound packing means 278. In addition, in other embodiments of this first version of the invention, the wound treatment device 215 may utilize wound packing means 278 without utilizing a suction drain 245, while in other embodiments wound packing means 278 may be utilized with a suction drain 245.

In the embodiment of the first version of the invention illustrated in FIG. 3, the vacuum system 250, which in conjunction with the wound treatment device 215 also represents a fourth aspect of this first version of the invention, is generally comprised of a suction bulb 281 having an inlet port 282 and an outlet port 283, a bulb connection tubing member 284, an exhaust tubing member 285, an exhaust control valve 286, a filter 287, and a supplemental vacuum system (illustrated schematically and generally designated 250a). In this embodiment, the suction bulb 281 is a hollow sphere that may be used to produce a supply of reduced pressure for use with the wound treatment device 215. In addition, the suction bulb 281 may also be used to receive and store fluid aspirated from the wound 260. The inlet port 282 of the suction bulb 281 is connected to one end of the bulb connection tubing member 284, which is also the reduced pressure supply means 240 in this embodiment. The connection tubing member 284 is connected by suction drain connection means to the top drain portion 245b at its other end in a manner so that the interior volume of the suction bulb 281 is in fluid communication with the suction drain 245. In this embodiment, the bulb connection tubing member 284 is sufficiently flexible to permit movement of the bulb connection tubing member 284, but is sufficiently rigid to resist constriction when reduced pressure is supplied to the suction drain 245 or when the location of the wound 260 is such that the patient must sit or lie upon the bulb connection tubing member 284 or upon the wound treatment device 215. The outlet port 283 of the suction bulb 281 is connected to the exhaust tubing member 285. In this embodiment, the exhaust tubing member 285 is sufficiently flexible to permit movement of the exhaust tubing member 285, but is sufficiently rigid to resist constriction when reduced pressure is supplied to the suction drain 245. The inlet port 282 of the suction bulb 281 may be connected to the bulb connection tubing member 284 and the outlet port 283 of the suction bulb 281 may be connected to the exhaust tubing member 285 using any suitable means, such as by welding, fusing, adhesives, clamps, or any combination of such means. In addition, in some embodiments, which are the preferred embodiments, the suction bulb 281, the bulb connection tubing member 284, and the exhaust tubing member 285 may be fabricated as a single piece. In the illustrated embodiment, the exhaust control valve 286 and the filter 287 are operably connected to the exhaust tubing member 285. In this embodiment, the exhaust control valve 286 is used to regulate the flow of fluids (gases and liquids) to and from the suction bulb 281 and the supplemental vacuum system 250a. In embodiments of the invention that do not have a supplemental vacuum system 250a, the exhaust control valve 286 regulates flow of fluids to and from the suction bulb 281 and the outside atmosphere. Generally, the exhaust control valve 286 allows fluids to flow out of the suction bulb 281 through the outlet port 283, but not to flow in the reverse direction unless permitted by the user of the appliance 210. Any type of flow control valve may be used as the exhaust control valve 286, as long as the valve is capable of operating in the anticipated environment involving reduced pressure and wound 260 exudate. Such valves are well known in the relevant art, such as sprung and unsprung flapper-type valves and disc-type valves. In this embodiment, the filter 287 is operably attached to the exhaust tubing member 285 between the outlet port 283 of the suction bulb 281 and the exhaust control valve 286. The filter 287 prevents potentially pathogenic microbes or aerosols from contaminating the exhaust control valve 286 (and supplemental vacuum system 250a), and then being vented to atmosphere. The filter 287 may be any suitable type of filter, such as a micropore filter. In other embodiments, the filter 287 may also be a hydrophobic filter that prevents any exudate from the wound 260 from contaminating the exhaust control valve 286 (and the supplemental vacuum system 250a) and then being vented to atmosphere. In still other embodiments, the filter 287 may perform both functions. It is to be noted, however, that the outlet port 283, the exhaust control valve 286, the filter 287, or any combination of the exhaust control valve 286 and the filter 287, need not be utilized in connection with the vacuum system 250 in other embodiments of the invention.

In some embodiments of these third and forth aspects of the first version of the invention illustrated in FIG. 3 that do not utilize a supplemental vacuum system 250*a*, the suction bulb 281 may be used to produce a supply of reduced pressure in the following manner. First, the user of the appliance 210 appropriately seals all of the component parts of the appliance 210 in the manner described herein. For example, the impermeable overlay 220 is sealed (or placed adjacent) to the body 170 and the suction drain 245 is sealed to the bulb connection tubing member 284 and the surface of the port 227. The user then opens the exhaust control valve 286 and applies force to the outside surface of the suction bulb 281, deforming it in a manner that causes its interior volume to be reduced. When the suction bulb 281 is deformed, the gas in the interior volume is expelled to atmosphere through the outlet port 283, the exhaust tubing member 285, the filter 287, and the exhaust control valve 286. The user then closes the exhaust control valve 286 and releases the force on the suction bulb 286. The suction bulb 281 then expands, drawing fluid from the area of the wound 260 under the wound treatment device 215 into the suction bulb 281 through the suction drain 245 and causing the pressure in such area to decrease. To release the reduced pressure, the user of the appliance 210 may open the exhaust control valve 286, allowing atmospheric air into the interior volume of the suction bulb 281. The level of reduced pressure may also be regulated by momentarily opening the exhaust control valve 286.

The suction bulb 281 may be constructed of almost any fluid impermeable flexible or semi-rigid material that is suitable for medical use and that can be readily deformed by application of pressure to the outside surface of the suction bulb 281 by users of the appliance 210 and still return to its original shape upon release of the pressure. For example, the suction bulb 281 may be constructed of rubber, neoprene, silicone, or other flexible or semi-rigid polymers, or any combination of all such materials. In addition, the suction bulb 281 may be of almost any shape, such as cubical, ellipsoidal, or polygonal. The suction bulb 281 may also be of varying size depending upon the anticipated use of the suction bulb 281, the size of the wound treatment device 215, use of a supplemental vacuum system 250*a*, the level of reduced pressure desired, and the preference of the user of the appliance 210. In the embodiment of the invention illustrated in FIG. 3, the supplemental vacuum system 250*a* is connected to the exhaust tubing member 285 and is used to provide a supplemental supply of reduced pressure to the suction bulb 281 and wound treatment device 215. In this embodiment, the supplemental vacuum system 250*a* may have substantially the same structure, features, characteristics and operation of the various embodiments of the vacuum system 50 of the first version of the invention described above and illustrated in connection with FIG. 2A and FIG. 2B. It is to be noted, however, that the supplemental vacuum system 250*a* need not be used in connection with the vacuum system 280 in other embodiments of the invention.

Except as described below, the wound treatment appliance 210 described above and illustrated in connection with FIG. 3 may generally be used in a manner similar to the wound treatment appliance 110 described above and illustrated in connection with FIG. 2A and FIG. 2B. As a result, except as described below, the example of how the embodiment of the wound treatment appliance 110 and the flexible overlay 120 described above and illustrated in connection FIG. 2A may be used in treatment of a wound 160 also applies to the embodiment of the appliance 210 of the third aspect of the first version of the invention described above and illustrated in connection with FIG. 3. In the case of the embodiment illustrated in FIG. 3, however, the wound packing means 278 is placed into the wound 260 prior to placement of the flexible overlay 220 over the portion of the wound 260 to be treated. In addition, the flexible overlay 220 is placed over the wound packing means 278. In embodiments where the distal end portion 245*a*' of a suction drain 245 is placed into the interior volume of, or adjacent to, the wound packing means 278, the distal end portion 245*a*' of the suction drain 245 is also placed in the appropriate position before the flexible overlay 220 is placed over the wound 260. In embodiments utilizing a suction drain 245 without wound packing means 278, the suction drain 245 is installed in the flexible overlay 220 before the flexible overlay 220 is placed over the wound 260.

Figure 4:
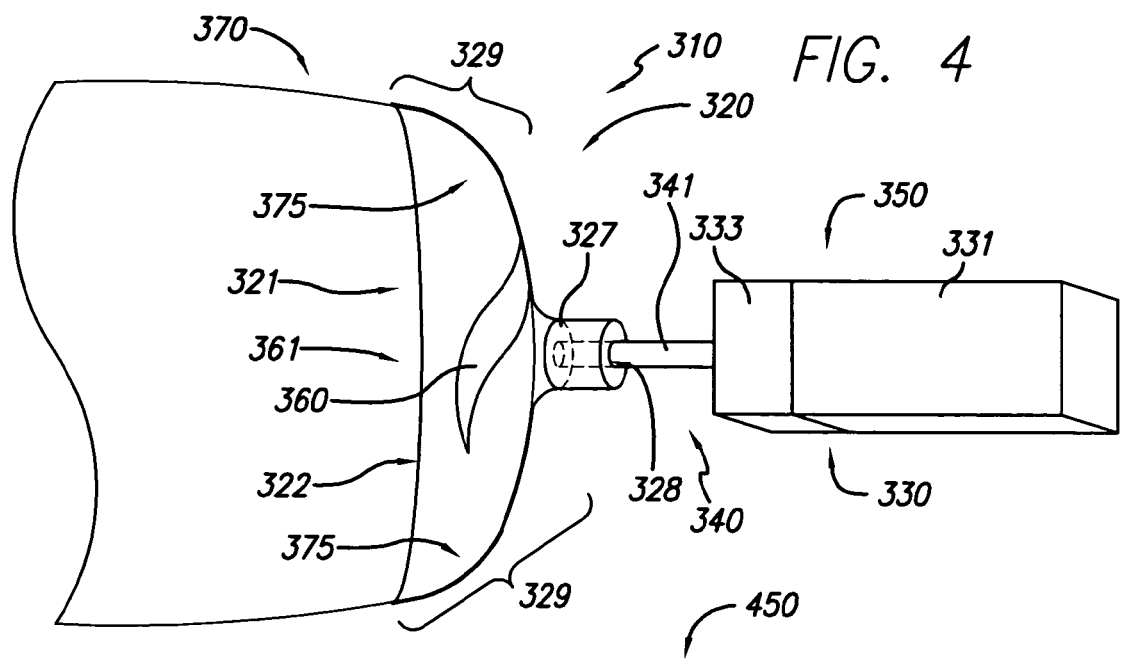
FIG. 4 is a view of an embodiment of a wound treatment appliance of the first version of the present invention, in which an embodiment of an impermeable flexible overlay, shown in cross-sectional elevational view from the side of the flexible overlay, covers a wound, and in which an embodiment of a vacuum system, shown in perspective view from the side of and below the vacuum system, provides reduced pressure within the area under the flexible overlay.

Another embodiment of the first version of the invention is the wound treatment appliance 310 illustrated in FIG. 4. FIG. 4 also illustrates another example of how the embodiment of the flexible overlay 20 described above and illustrated in connection with FIG. 1A may be used to provide reduced pressure treatment for a wound 360 on the body 370 of a patient. In this embodiment, the wound treatment appliance 310 is comprised of a flexible overlay 320 and a vacuum system, generally designated 350, that is operably connected to, and provides a supply of reduced pressure to, the flexible overlay 320. In addition, in this embodiment, the vacuum system 350 is further comprised of a reduced pressure supply source, generally designated 330, which is described in more detail below, and reduced pressure supply means, generally designated 340, which are described in more detail below. In this embodiment, the reduced pressure supply means 340 are used to connect the reduced pressure supply source 330 to the flexible overlay 320 in a manner so that reduced pressure is supplied to the area under the flexible overlay 320, as described in more detail below. In the embodiment of the first version of the invention illustrated in FIG. 4, the flexible overlay 320 has substantially the same structure, features and characteristics as the flexible overlay 20 described above and illustrated in connection with FIG. 1A. It is to be noted, however, that in other embodiments of this first version of the invention, the flexible overlay 320 may have substantially the same structure, features and characteristics as any embodiment of all of the flexible overlays 20, 20*a*, 20*b*, 20*c* of the first version of the invention described above and illustrated in connection with FIG. 1A, FIG. 1B, FIG. 1C, and FIG. 1D, respectively. In this example, the flexible overlay 320 is placed over and encloses the entire wound 360, which is at the distal end of an amputated limb. It is to be noted that in other embodiments, the appliance 310 may also be comprised of tissue protection means 375, which may be substantially the same as the tissue protection means 175 of the first version of the invention described above and illustrated in connection with FIG. 2A. In other embodiments, the appliance 310 may also be comprised of wound packing means (not illustrated), which may be substantially the same as the wound packing means 278 of the first version of the invention described above and illustrated in connection with FIG. 3.

In the embodiment of the first version of the invention illustrated in FIG. 4, the reduced pressure supply source 330 of the vacuum system 350, which produces a source of reduced pressure or suction that is supplied to the flexible overlay 320, includes a small, portable vacuum pump 331, a filter 333, and a power source (not illustrated) that is contained within the housing for the portable vacuum pump 331. In the illustrated embodiment, predetermined amounts of suction or reduced pressure are produced by the portable vacuum pump 331. The portable vacuum pump 331 is preferably controlled by a control device (not illustrated) that is also located within the housing for the portable vacuum pump 331, which may provide substantially the same functions as the control device 132 of the first version of the invention described above and illustrated in connection with FIG. 2A and FIG. 2B. Except for its smaller size, the portable vacuum pump 331 may operate in substantially the same manner as the vacuum pump 131 of the first version of the invention described above and illustrated in connection with FIG. 2A and FIG. 2B. In the embodiment illustrated in FIG. 4, the filter 333 may have the same structure, features, characteristics and operation, and provide substantially the same functions, as the filter 133 of the first version of the invention described above and illustrated in connection with FIG. 2A and FIG. 2B. The power source may be any source of energy currently known in the art or that may be developed in the art in the future that may be used to power the portable vacuum pump 331. For example, in some embodiments, the power source may be a fuel cell, battery or connection to a standard electrical outlet. In the illustrated embodiment, the filter 333 is rigidly connected to the portable vacuum pump 331. It is to be noted that in other embodiments of the first version of the invention, the reduced pressure supply source 330 may not have a filter 333.

In the embodiment of the first version of the invention illustrated in FIG. 4, the reduced pressure supply means 340 of the vacuum system 350, which is used to connect the reduced pressure supply source 330 to a port 327 on the flexible overlay 320 so that reduced pressure is supplied to the area of the wound 360 under the flexible overlay 320, is comprised of at least one tubing member 341. In this embodiment, the at least one tubing member 341 is a rigid tubing member. In other embodiments, the at least one tubing member 341 may be sufficiently flexible to permit movement of the at least one tubing member 341, but is sufficiently rigid to resist constriction when reduced pressure is supplied to the port 327 or when the location of the wound 360 is such that the patient must sit or lie upon the at least one tubing member 341 or upon the flexible overlay 320. In the embodiment illustrated in FIG. 4, the at least one tubing member 341 is connected to the port 327 by inserting one end of the at least one tubing member 341 into an opening 328 in the port 484 and sealing (such as with an adhesive) the at least one tubing member 341 to the port 327. It is to be noted that in other embodiments, the at least one tubing member 341 may be connected to the port 327 using any suitable means currently known in the relevant art or developed in the relevant art in the future. Examples include the suction drain connection means of the first version of the invention discussed above and illustrated in connection with FIG. 3. Similar means may be used to connect the other end of the at least one tubing member 341 to the reduced pressure supply source 330 providing the reduced pressure. In other embodiments of this first version of the invention, the reduced pressure supply means 340 may further comprise a fluid collection system (not illustrated), which may generally have the same structure, features, characteristics and operation, and perform the same functions, as the fluid collection system 142 of the first version of the invention described above and illustrated in connection with FIG. 2A and FIG. 2B.

Figure 5:
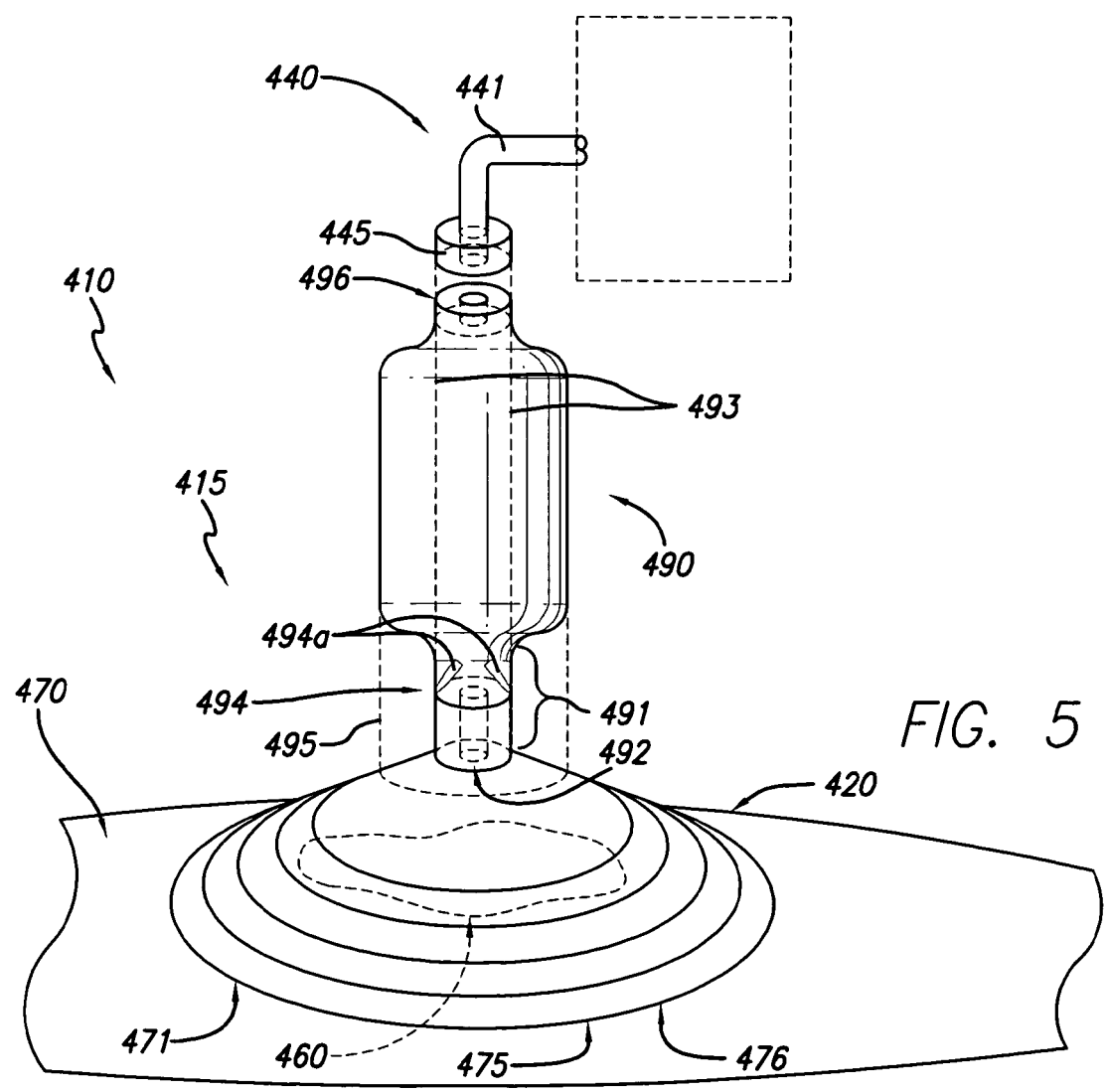
FIG. 5 is a view of an embodiment of a wound treatment appliance of a second version of the present invention, in which an embodiment of an impermeable flexible overlay, shown in perspective view from the side of and above the flexible overlay, covers a wound, and in which an embodiment of a vacuum system, depicted generally and shown in schematic elevation view, provides reduced pressure within the area under the flexible overlay.

An embodiment of a second version of the invention is the wound treatment appliance 410 illustrated in FIG. 5. In this embodiment, the appliance 410 is comprised of a wound treatment device 415, which is further comprised of a flexible overlay 420, a collection chamber 490 to receive and hold fluid aspirated from the wound 460, collection chamber attachment means to operably attach the collection chamber 490 to the overlay 420, as described in more detail below, and reduced pressure supply means, generally designated 440, which are described in more detail below. In this embodiment, the flexible overlay 420 is adapted to be placed over and enclose all or a portion of the wound 460 in the same manner as the flexible overlay 20 described in detail above and illustrated in connection with FIG. 1A. It is to be noted, however, that the flexible overlay 420 illustrated in FIG. 5 is shown in position on the body 470 over the wound 460, but not in its collapsed state. In the illustrated embodiment, and except as described in more detail below, the flexible overlay 420 has substantially the same structure, features and characteristics as the flexible overlay 20 described in detail above and illustrated in connection with FIG. 1A. In the various embodiments of this second version of the invention, except as described in more detail below, the flexible overlay 420 may have substantially the same structure, features, characteristics and operation as the embodiments of the flexible overlays 20, 20*a*, 20*b*, 20*c*, 120, 220 described in more detail above and illustrated in connection with FIG. 1A, FIG. 1B, FIG. 1C, FIG. 1D, FIG. 2A, and FIG. 3, respectively. In the illustrated embodiment, reduced pressure supply means, generally designated 440, which are described in more detail below, are used to operably connect the collection chamber 490 to a reduced pressure supply source, generally designated 430, which is described in more detail below, that provides a supply of reduced pressure to the collection chamber 490, so that the volume within the collection chamber 490 and under the flexible overlay 420 in the area of the wound 460 to be treated are supplied with reduced pressure by the reduced pressure supply source 430. Together, the reduced pressure supply means 440 and the reduced pressure supply source 430 comprise a vacuum system, generally designated 450. In the various embodiments of this second version of the invention, except as described in more detail below, the reduced pressure supply means 440 used to connect the reduced pressure supply source 430 to the collection chamber 490 may have substantially the same structure, features, characteristics and operation as the reduced pressure supply means 140, 240, 340 described above and illustrated in connection with FIG. 2A, FIG. 2B, FIG. 3, and FIG. 4, respectively. In addition, in the various embodiments of this second version of the invention, except as described in more detail below, the reduced pressure supply source 430 used to provide the supply of reduced pressure to the collection chamber 490 may have substantially the same structure, features, characteristics and operation as the reduced pressure supply source 130, 280, 330 described above and illustrated in connection with FIG. 2A, FIG. 2B, FIG. 3, and FIG. 4, respectively.

In the embodiment of the appliance 410 illustrated in FIG. 5, the collection chamber 490 is approximately cylindrical in shape. In other embodiments, the collection chamber 490 may have other shapes. For example, the collection chamber may be shaped approximately as a sphere, ellipsoid, cube, polyhedron, or other shape or combination of such shapes, as long as the collection chamber 490 has an interior volume to receive and hold fluid aspirated from the wound 460. The collection chamber 490 may also be of almost any size. For example, the collection chamber 490 may be relatively small where the wound 460 is expected to aspirate only a small volume of fluid. On the other hand, the collection chamber 490 may be relatively large where it is expected that the wound 460 will aspirate a large volume of fluid. As a result, the preferred size of the collection chamber 490 is dependent upon the size of the wound 460 to be treated, the size of the flexible overlay 420, the type of wound 460 to be treated, and the preference of the user of the appliance 410. In the various embodiments of this second version of the invention, the collection chamber 490 may be comprised of almost any medical grade material that is currently known in the art or that may be developed in the art in the future, as long as such material is fluid-impermeable and suitable for purposes of wound treatment (e.g., can be sterilized and does not absorb significant amounts of wound 460 exudate). For example, the collection chamber 490 may be comprised of rubber (including neoprene) and polymer materials, such as silicone, silicone blends, silicon substitutes, polyvinyl chloride, polycarbonates, polyester-polycarbonate blends, or a similar polymer, or combinations of all such materials. It is to be noted that the collection chamber 490 may have a rigid or semi-rigid structure in some embodiments. In other embodiments, the collection chamber 490 may be more flexible so that it can be squeezed in a manner similar to the suction bulb 281, as described above and illustrated in connection with FIG. 3. Although the collection chamber 490 may be constructed of a material different from the material comprising the flexible overlay 420 in various embodiments of the invention, the collection chamber 490 is preferably constructed from the same material comprising the flexible overlay 420. The collection chamber 490 may be constructed using any suitable means currently known in the art or that may be developed in the art in the future. For example, a collection chamber 490 constructed of silicone may be manufactured by means of injection molding.

In the various embodiments of this second version of the invention, the collection chamber attachment means operably attaches the collection chamber 490 to the flexible overlay 420 in a manner so that exudate and reduced pressure are permitted to flow between the collection chamber 490 and the volume under the flexible overlay 420 in the area of the wound 460. Also, in the various embodiments of the second version of the invention, as illustrated by the appliance 410 in FIG. 5, the collection chamber 490 is positioned approximately adjacent to the flexible overlay 420 on the side of the flexible overlay 420 opposite the wound 460. Although the collection chamber 490 and the collection chamber attachment means are positioned approximately at the apex of the flexible overlay 420 in the illustrated embodiment, in other embodiments the collection chamber 490 and collection chamber attachment means may be positioned at almost any location on the surface of the impermeable overlay 420 opposite the wound 460, as long as the collection chamber 490 and collection chamber attachment means do not materially interfere with the operation of the flexible overlay 420. As illustrated in FIG. 5, the collection chamber attachment means may be a rigid or semi-rigid connecting member 491 between the collection chamber 490 and the flexible overlay 420. In this embodiment, the connecting member 491 is approximately cylindrical in shape and has a port 492 therein, which is also approximately cylindrical in shape and extends between the collection chamber 490 and the flexible overlay 420 so that fluids can flow between the collection chamber 490 and the flexible overlay 420. In other embodiments, the connecting member 491 and the port 492 may be of almost any shape or combination of shapes. For example, the connecting member 491 and the port 492 may be shaped approximately as a sphere, ellipsoid, cube, polygon, paraboloid, or any other shape or combination of shapes, as long as the connecting member 491 provides a rigid or semi-rigid connection between the collection chamber 490 and the flexible overlay 420 that is adequate to support the collection chamber 490 when it is filled with exudate from the wound 460, and the port 492 is of a size and shape adequate to allow the flow of exudate from the wound 460 between the collection chamber 490 and the flexible overlay 420. For example, the collection chamber 490 in some embodiments may have approximately the same outside diameter as the connecting member 491, as illustrated by the phantom lines 493 in FIG. 5. The connecting member 491 may generally be constructed of any material that is suitable for construction of the collection chamber 490 or the flexible overlay 420, and is preferably constructed from the same materials as the collection chamber 490 and the flexible overlay 420. In various embodiments, the collection chamber 490 and the flexible overlay 420 may be connected to the connecting member 491 using any suitable means, such as by adhesives, welding, fusing, clamps, and other fastening means or combinations of such means. In yet other embodiments, the collection chamber 490, the flexible overlay 420, and the connecting member 491 may be fabricated as a single piece. In still other embodiments, one or more of the connections between the collection chamber 490, the flexible overlay 420, and the connecting member 491 may provide for removing one component from another to empty fluid from the collection chamber 490. For example, the collection chamber 490, the flexible overlay 420, and the connecting member 491 may each be threaded at their points of connection so that they can be screwed together and then unscrewed when desired. In still other embodiments, the collection chamber 490 and the flexible overlay 420 may be directly connected together without a connecting member 491, as long as the connection allows fluid to flow between the collection chamber 490 and the flexible overlay 420. Such connection may be made using any of the means described above in this paragraph.

In some embodiments of this second version of the invention, as illustrated in FIG. 5, the connecting member 491, as the collection chamber attachment means, may be further comprised of a flow control means, which is described in more detail below, operably positioned between the collection chamber 490 and the flexible overlay 420. In these embodiments, the flow control means permits fluid aspirated from the wound 460 to flow from the volume under the flexible overlay 420 in the area of the wound 460 through the port 492 into the collection chamber 490, but not in the opposite direction. In the illustrated embodiment, the flow control means is comprised of a flapper-type valve 494. In this embodiment, the valve 494 has two flapper members 494*a* that are hinged at their distal end to a portion of the connecting member 491, and the flapper members 494*a* are of a shape and size adapted to substantially close the port 492 when they are positioned in the closed position. In other embodiments, the flow control means may be comprised of a disc-type valve, wherein the disc of the valve moves with the flow of fluids and contacts a seat disposed around the perimeter of the port when the flow of fluids is misdirected, so that the port is sealed closed and prevents fluid flow in the wrong direction. In some embodiments, as illustrated in FIG. 5, the collection chamber 490 may be further comprised of a shroud 495 (illustrated by the phantom lines) that extends from a portion of the collection chamber 490 to the flexible overlay 420. In these embodiments, the shroud 495 is approximately tubular in shape. In other embodiments, the shroud 495 may have other shapes. The shroud 495 generally provides additional support for the collection chamber 490 and may also provide for a more aesthetically pleasing appearance for the appliance 410. In addition, in the embodiment of the appliance 410 illustrated in FIG. 5, the reduced pressure supply means 440 is connected to the collection chamber 490 by means of a stopper 445 adapted to fit into an opening 496 in the collection chamber 490. The stopper 445 forms a seal with the portion of the collection chamber 490 adjacent to the opening 496 so that reduced pressure can be maintained within the interior volume of the collection chamber 490. In this embodiment, the reduced pressure supply means is comprised of a tubular member 441 that is positioned in a port 446 in the stopper 445 at one end and is connected to the reduced pressure supply source 430 at the other end.

The embodiment of the appliance 410 illustrated in FIG. 5 may be used to treat a wound 460 on a body 470 using a method comprising the following steps. First, the wound treatment device 415 is positioned on the body 470 over the area of the wound 460 to be treated. Next, the vacuum system 450 is operably connected to the collection chamber 490. The flexible overlay 420 may then be collapsed in the approximate direction of the wound 460 when reduced pressure is supplied to the volume under the flexible overlay 420 in the area of the wound 460 so that an approximately hermetic seal (as illustrated and described in more detail above in connection with FIG. 2A) is formed between the flexible overlay 420 and the body 470 in the area of the wound 460. Next, reduced pressure is maintained in the volume of the flexible overlay 420 in the area of the wound 460 until the area of the wound 460 being treated has progressed toward a selected stage of healing. In other embodiments, the method may further comprise the step of placing tissue protection means 475, which may be substantially the same as the tissue protection means 175, as described above and illustrated in connection with FIG. 2A, on the tissue 471 of the body 470 that is to be approximately adjacent to the flexible overlay 420, such step being performed prior to positioning the flexible overlay 420 over the area of the wound 460 to be treated. In yet other embodiments, the method further comprises the step of placing wound packing means (not illustrated), which may be substantially the same as the wound packing means 278, as described above and illustrated in connection with FIG. 3, between the wound 460 and the impermeable overlay 420 in the area of the wound 460 to be treated, such step being performed prior to positioning the impermeable overlay 420 over the area of the wound 460 to be treated. In still other embodiments, the reduced pressure under the flexible overlay 420 in the area of the wound 460 is in the range from approximately 20 mm of Hg below atmospheric pressure to approximately 125 mm of Hg below atmospheric pressure. In other embodiments, the reduced pressure is applied in a cyclic nature, the cyclic nature providing alternating time periods of application of reduced pressure and without application of reduced pressure. In yet other embodiments, the method is further comprised of the step of emptying any fluid collected in the collection chamber 490. This step may be performed after the flexible overlay 420 is collapsed in the approximate direction of the wound 460 and may also be performed before or after the area of the wound 460 being treated has progressed toward a selected stage of healing.

Figure 6:
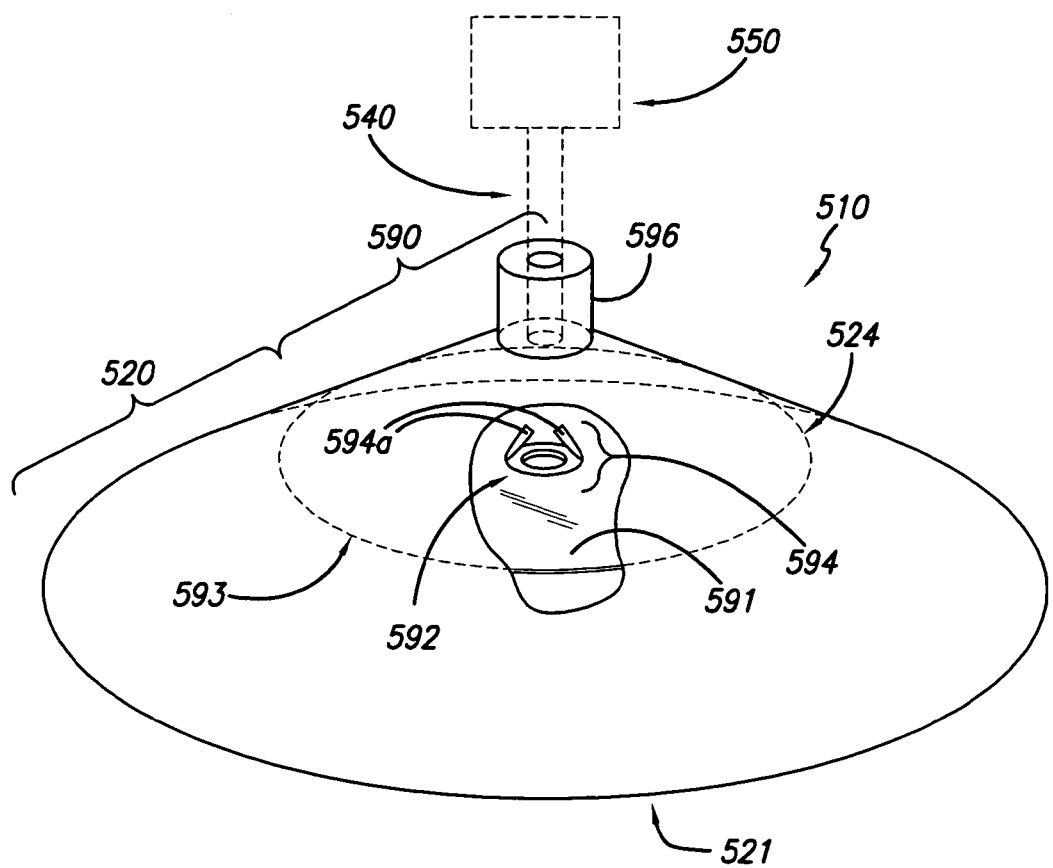
FIG. 6 is a view of another embodiment of a wound treatment appliance of a second version of the present invention, in which an embodiment of an impermeable flexible overlay is shown in partially broken away perspective view from the side of and above the flexible overlay (as the flexible overlay would be oriented when placed on the body of a patient), and in which an embodiment of a vacuum system, depicted generally and shown in schematic elevation view, provides reduced pressure within the area under the flexible overlay.

Another embodiment of the second version of the invention is the wound treatment appliance 510 illustrated in FIG. 6. In this embodiment, the appliance 510 is comprised of a flexible overlay 520, a collection chamber 590 to receive and hold fluid aspirated from a wound (not shown), collection chamber attachment means to operably attach the collection chamber 590 to the flexible overlay 520, as described in more detail below, and reduced pressure supply means, generally designated 540, which are described in more detail below. In this embodiment, the flexible overlay 520 is adapted to be placed over and enclose all or a portion of a wound in the same manner as the flexible overlay 20a described in detail above and illustrated in connection with FIG. 1B. It is to be noted that the flexible overlay 520 illustrated in FIG. 6 is not shown in its collapsed state. In the illustrated embodiment, and except as described in more detail below, the flexible overlay 520 has substantially the same structure, features and characteristics as the flexible overlay 20a described in detail above and illustrated in connection with FIG. 1B. In other embodiments, the flexible overlay 520 may be of other shapes and have other features. For example, the flexible overlay 520 may be of the shape and have the features illustrated and described above in connection with the appliance 10b and 10c of FIG. 1C and FIG. 1D, respectively. In the embodiment illustrated in FIG. 6, the reduced pressure supply means 540, which are described in more detail below, may be used to operably connect the collection chamber 590 to a reduced pressure supply source (not shown), which is described in more detail below, that provides a supply of reduced pressure to the collection chamber 590, so that the volume within the collection chamber 590 and under the flexible overlay 520 in the area of the wound to be treated are supplied with reduced pressure by the reduced pressure supply source. Together, the reduced pressure supply means 540 and the reduced pressure supply source comprise a vacuum system, generally designated 550. In this embodiment of the second version of the invention, except as described in more detail below, the reduced pressure supply means 540 used to connect the reduced pressure supply source to the collection chamber 590 may have substantially the same structure, features, characteristics and operation as the reduced pressure supply means 140, 240, 340 described above and illustrated in connection with FIG. 2A, FIG. 2B, FIG. 3, and FIG. 4, respectively. In addition, in this embodiment of the second version of the invention, except as described in more detail below, the reduced pressure supply source used to provide the supply of reduced pressure to the collection chamber 590 may have substantially the same structure, features, characteristics and operation as the reduced pressure supply source 130, 280, 330 described above and illustrated in connection with FIG. 2A, FIG. 2B, FIG. 3, and FIG. 4, respectively. The embodiment of the appliance 510 illustrated in FIG. 6 may be used to treat a wound on a body using substantially the same method described above in connection with the appliance 410 illustrated in FIG. 5.

In the embodiment illustrated in FIG. 6, the collection chamber 590 is positioned approximately adjacent to the flexible overlay 520 on the side of the flexible overlay 520 opposite the wound. In this embodiment, the collection chamber attachment means, as described in more detail below, is comprised of a membrane 591. In this embodiment, the membrane 591 acts as a barrier separating the collection chamber 590 and the flexible overlay 520, so that the membrane 591 acts as a portion of the surface of the collection chamber 590 and a portion of the surface of the flexible overlay 520. In addition, the membrane 591 has at least one port 592 therein so that the volume within the collection chamber 590 is in fluid communication with the volume under the flexible overlay 520 in the area of the wound. It is to be noted that there may be more than one port 592 in other embodiments. The number of ports 492 is generally dependent upon the size and shape of the collection chamber 590, the size and shape of the impermeable flexible overlay 520, the anticipated amount of exudate to be aspirated from the wound, the level of reduced pressure to be utilized, and the individual preference of the user of the appliance 510. In embodiments where the flexible overlay 520 has an approximately elongated conical shape, as illustrated in FIG. 6, the flexible overlay 520 may have a base end opening 521 and a top end opening 524 opposite the base end opening 521. In these embodiments, the base end opening 521 may have an either approximately circular shape or approximately elliptical shape sized to be placed over and enclose the area of the wound to be treated. The top end opening 524 may have either an approximately circular shape or approximately elliptical shape. In the illustrated embodiments, the membrane 591 is adapted to be of the same shape and size as the top end opening 524 and the membrane 591 is positioned so that it is attached to the entire perimeter of the top end opening 524 and covers the entire top end opening 524. The membrane 591 may be attached to the perimeter of the top end opening 524 by any suitable means currently known in the relevant art or developed in the art in the future. Examples of such means include welding or fusing the membrane 591 to the perimeter of the top end opening 524. Alternatively, the membrane 591 may be fabricated as a single piece with the flexible overlay 520.

In the embodiment of the appliance 510 illustrated in FIG. 6, the collection chamber 590 has an approximately elongated conical shape, a chamber bottom end opening 593, and a reduced pressure supply port 596 positioned at the apex of the collection chamber 590 opposite the chamber bottom end opening 593. The reduced pressure supply port 596 may be used to operably connect the reduced pressure supply means 540 to the collection chamber 590. In some embodiments, a micropore or hydrophobic filter or both (not shown) may be operably positioned within the reduced pressure supply port 596 or the connection with the reduced pressure supply means 540 to retain the exudate from the wound within the collection container 590 or to prevent exudate from contaminating portions of the vacuum system 550, or both. In the illustrated embodiment, the chamber bottom end opening 593 is adapted to be of approximately the same size and shape as the top end opening 524 of the impermeable flexible overlay 520. In other embodiments, the collection chamber 590 may be of other shapes and sizes and its bottom end opening 593 may not necessarily be of the same size and shape as the top end opening 524 of the flexible overlay 520. In all embodiments, however, the collection chamber 590 is attached to the membrane 591 in a manner so that the membrane 591 acts as a portion of the surface of the collection chamber 590 and so that the volume within the collection chamber 590 is airtight, except for the at least one port 592 and the reduced pressure supply port 596. In the preferred embodiment, the collection chamber 590 and the flexible overlay 520 have the shapes illustrated in FIG. 6. The membrane 591 may be attached to the perimeter of the chamber bottom end opening 593 by any suitable means currently known in the relevant art or developed in the art in the future. Examples of such means include welding or fusing the membrane 591 to the perimeter of the chamber bottom end opening 593. Alternatively, the membrane 591 or the flexible overlay 520, or both, may be fabricated as a single piece with the collection chamber 590. The preferred shapes and sizes of the collection chamber 590 and the flexible overlay 520 are dependent upon the size and type of wound to be treated, the area of the body on which the wound is positioned, the level of reduced pressure to be utilized, the amount of collapse of the flexible overlay 520 desired, and the preference of the user of the appliance 510.

In this embodiment of the second version of the invention, the collection chamber 590 may be comprised of almost any medical grade material that is currently known in the art or that may be developed in the art in the future, as long as such material is fluid-impermeable and suitable for purposes of wound treatment (e.g., can be sterilized and does not absorb significant amounts of wound exudate). For example, the collection chamber 590 may be comprised of rubber (including neoprene) and flexible polymer materials, such as silicone, silicone blends, silicone substitutes, polyvinyl chloride, polycarbonates, polyester-polycarbonate blends, or a similar polymer, or combinations of all such materials. It is to be noted that the collection chamber 590 may have a rigid or semi-rigid structure in some embodiments. In other embodiments, the collection chamber 590 may be more flexible so that it can be squeezed in a manner similar to the suction bulb 281, as described above and illustrated in connection with FIG. 3. Although the collection chamber 590 may be constructed of a material different from the material comprising the flexible overlay 520 in various embodiments of the invention, the collection chamber 590 is preferably constructed from the same material comprising the flexible overlay 520. The collection chamber 590 may be constructed using any suitable means currently known in the art or that may be developed in the art in the future. For example, a collection chamber 590 constructed of silicone may be manufactured by means of injection molding.

In the embodiment of the second version of the invention illustrated in FIG. 6, the membrane 591 and its means of being sealed to the perimeters of the top end opening 524 and the chamber bottom end opening 593, together as collection chamber attachment means, operably attach the collection chamber 590 to the impermeable overlay 520 in a manner so that exudate and reduced pressure are permitted to flow between the collection chamber 590 and the volume under the impermeable overlay 520 in the area of the wound. In the embodiment illustrated in FIG. 6, the at least one port 592 is approximately cylindrical in shape and extends between the collection chamber 590 and the flexible overlay 520 so that fluids can flow between the collection chamber 590 and the flexible overlay 520. In other embodiments, the at least one port 592 may be of almost any shape or combination of shapes. In some embodiments of this second version of the invention, as illustrated in FIG. 6, the membrane 591 comprising the collection chamber attachment means may be further comprised of a flow control means, which is described in more detail below, operably connected with the at least one port 592 and positioned between the collection chamber 590 and the flexible overlay 520. In these embodiments, the flow control means permits fluid aspirated from the wound to flow from the volume under the flexible overlay 520 in the area of the wound 560 through the at least one port 592 into the collection chamber 590, but not in the opposite direction. In the illustrated embodiment, the flow control means is comprised of a flapper-type valve 594. In this embodiment, the valve 594 has two flapper members 594a that are hinged at their distal end to a portion of the membrane 491 or supporting structure surrounding the at least one port 492 and the flapper members 594a are of a shape and size adapted to substantially close the at least one port 592 when they are positioned in the closed position. In other embodiments, the flow control means may be comprised of a disc-type of valve.

What is claimed is:

1. A wound treatment apparatus comprising:
   a liquid impermeable overlay configured to be placed over all or a portion of a wound and maintain reduced pressure in the volume under the liquid impermeable overlay in an area of the wound, wherein the liquid impermeable overlay comprises a cup-shaped portion; and a reduced pressure supply conduit that is configured to provide a supply of reduced pressure to the liquid impermeable overlay;

wherein the liquid impermeable overlay comprises a plurality of raised portions or ribs disposed on a surface of the liquid impermeable overlay extending radially outward from a central portion of the cup-shaped portion; and wherein the plurality of raised portions or ribs are configured to face the wound when the overlay is placed over all or a portion of the wound.

2. The apparatus of claim 1, wherein the liquid impermeable overlay maintains shape upon application of reduced pressure.

3. The apparatus of claim 1, wherein the liquid impermeable overlay comprises an opening sized to be placed over the wound.

4. The apparatus of claim 1, further comprising a reduced pressure source configured to supply reduced pressure to the volume under the liquid impermeable overlay in the area of the wound.

5. The apparatus of claim 1, wherein the plurality of raised portions or ribs are disposed on a side surface of the cup-shaped portion.

6. The apparatus of claim 1, wherein the liquid impermeable overlay comprises stiffening members.

7. The apparatus of claim 1, wherein at least some of the plurality of raised portions or ribs extend from a center portion of the liquid impermeable overlay.

8. The apparatus of claim 1, wherein at least some of the plurality of raised portions or ribs extend radially from an upper portion of the liquid impermeable overlay.

9. The apparatus of claim 1, wherein the plurality of raised portions or ribs are evenly spaced around at least a portion of a circumference of the liquid impermeable overlay.

10. The apparatus of claim 1, wherein the plurality of raised portions or ribs are recessed into a surface of the liquid impermeable overlay.

11. The apparatus of claim 1, wherein the liquid impermeable overlay has a circular perimeter.

12. The apparatus of claim 1, further comprising a port extending above at least a portion of the liquid impermeable overlay, wherein the port is configured to supply reduced pressure to an area of the wound underneath the liquid impermeable overlay.

13. A wound treatment apparatus comprising:
a liquid impermeable overlay configured to be placed over all or a portion of the wound to be treated, wherein the overlay comprises a pre-formed cup-shaped portion having a concave side configured to face the wound, with a plurality of raised portions or ribs disposed on concave side surfaces of the cup-shaped portion;

a port extending above at least a portion of the liquid impermeable overlay when in use configured to supply reduced pressure to an area of the wound underneath the liquid impermeable overlay, wherein the port extends from the cup-shaped portion; and at least one tubing member configured to be connected to the port and configured to supply reduced pressure to the liquid impermeable overlay from a source of negative pressure;

wherein the plurality of raised portions or ribs extend radially outwardly and downwardly from a central portion of the cup-shaped portion to a lower portion of the cup-shaped portion.

14. The apparatus of claim 13, wherein the liquid impermeable overlay is constructed from silicone.

15. The apparatus of claim 13, wherein the liquid impermeable overlay maintains its shape upon application of reduced pressure.

16. The apparatus of claim 13, wherein the liquid impermeable overlay is configured to collapse in the approximate direction of the area of the wound to be treated when reduced pressure is supplied to the volume under the liquid impermeable overlay in the area of the wound.

17. The apparatus of claim 13, further comprising a reduced pressure supply source, wherein the reduced pressure supply source is configured to be fluidically connected with the reduced pressure supply conduit.

18. The apparatus of claim 17, further comprising a container for collecting wound exudate, the container configured to be positioned in a fluid flow path between the liquid impermeable overlay and the reduced pressure supply source.

19. The apparatus of claim 13, wherein the plurality of raised portions or ribs have a greater stiffness than remaining portions of the cup-shaped portion.

20. The apparatus of claim 13, wherein the plurality of raised portions or ribs are evenly spaced around at least a portion of a circumference of the cup-shaped portion of the overlay.

21. The apparatus of claim 13, wherein the plurality of raised portions or ribs are molded into the side surfaces of the cup-shaped portion.

22. The apparatus of claim 13, wherein the liquid impermeable overlay has a circular perimeter.

* * * * *